(12) United States Patent
Pasternak et al.

(10) Patent No.: US 10,208,064 B2
(45) Date of Patent: Feb. 19, 2019

(54) INHIBITORS OF THE RENAL OUTER MEDULLARY POTASSIUM CHANNEL

(71) Applicants: MERCK SHARP & DOHME CORP., Rahway, NJ (US); Alexander Pasternak, Kenilworth, NJ (US); Ian Davies, Rahway, NJ (US); Fa-Xiang Ding, Kenilworth, NJ (US); Jinlong Jiang, Kenilworth, NJ (US); Shuzhi Dong, Kenilworth, NJ (US); Xin Gu, Kenilworth, NJ (US); Takao Suzuki, Shanghai (CN); Joseph P. Vacca, Lansdale, PA (US); Zhifa Pu, Shanghai (CN); Shouning Xu, Shanghai (CN)

(72) Inventors: Alexander Pasternak, Princeton, NJ (US); Ian Davies, Princeton, NJ (US); Fa-Xiang Ding, Staten Island, NY (US); Jinlong Jiang, Scotch Plains, NJ (US); Shuzhi Dong, Plainsboro, NJ (US); Xin Gu, Scotch Plains, NJ (US); Takao Suzuki, Shanghai (CN); Joseph P. Vacca, Telford, PA (US); Zhifa Pu, Shanghai (CN); Shouning Xu, Shanghai (CN)

(73) Assignee: Merck Sharp & Dohme Corp.

( * ) Notice: Subject to any disclaimer, the term of this patent is extended or adjusted under 35 U.S.C. 154(b) by 0 days.

(21) Appl. No.: 15/323,989

(22) PCT Filed: Jul. 9, 2015

(86) PCT No.: PCT/US2015/039635
§ 371 (c)(1),
(2) Date: Jan. 5, 2017

(87) PCT Pub. No.: WO2016/010802
PCT Pub. Date: Jan. 21, 2016

(65) Prior Publication Data
US 2017/0197989 A1    Jul. 13, 2017

(30) Foreign Application Priority Data

Jul. 14, 2014 (WO) ................ PCT/CN2014/082119

(51) Int. Cl.
*C07D 513/10* (2006.01)
*C07D 519/00* (2006.01)
*A61K 45/06* (2006.01)
*A61K 31/435* (2006.01)
*A61K 31/4745* (2006.01)
*A61K 31/4375* (2006.01)

(52) U.S. Cl.
CPC .......... *C07D 519/00* (2013.01); *A61K 31/435* (2013.01); *A61K 31/4375* (2013.01); *A61K 31/4745* (2013.01); *A61K 45/06* (2013.01)

(58) Field of Classification Search
CPC .................................................... C07D 513/10
USPC ............................................ 546/15; 514/278
See application file for complete search history.

(56) References Cited

U.S. PATENT DOCUMENTS

| | | | |
|---|---|---|---|
| 1,000,484 | A | 8/1911 | Auchu |
| 8,673,920 | B2 | 3/2014 | Pasternak et al. |
| 8,952,166 | B2 | 2/2015 | Ding et al. |
| 8,999,990 | B2 | 4/2015 | Tang et al. |
| 9,018,211 | B2 | 4/2015 | Pasternak et al. |
| 9,056,859 | B2 | 6/2015 | Pasternak et al. |
| 9,062,070 | B2 | 6/2015 | Pasternak et al. |
| 9,073,882 | B2 | 7/2015 | Tang et al. |
| 9,108,947 | B2 | 8/2015 | Walsh et al. |
| 9,139,585 | B2 | 9/2015 | Walsh et al. |
| 9,206,198 | B2 | 12/2015 | Ding et al. |
| 9,206,199 | B2 | 12/2015 | Pio et al. |
| 9,527,830 | B2 | 12/2016 | Walsh et al. |
| 9,573,961 | B2 | 2/2017 | Pasternak et al. |
| 9,604,998 | B2 | 3/2017 | Pasternak et al. |
| 9,718,808 | B2 | 8/2017 | Biswas et al. |

(Continued)

FOREIGN PATENT DOCUMENTS

| | | |
|---|---|---|
| WO | 2013062900 A1 | 5/2013 |
| WO | 2013066718 A2 | 5/2013 |

(Continued)

OTHER PUBLICATIONS

Bhave,G., Development of a selective small-molecule inhibitor Kir1.1, the renal outer medullary potassium channel, Mol. Pharmacol., 2011, 42-50, 79.

(Continued)

*Primary Examiner* — Patricia L Morris
(74) *Attorney, Agent, or Firm* — Sarah Hooson; Catherine D. Fitch

(57) ABSTRACT

The present invention provides compounds of Formula (I) and the pharmaceutically acceptable salts thereof, which are inhibitors of the ROMK (Kir1.1) channel. The compounds may be used as diuretic and/or natriuretic agents and for the therapy and prophylaxis of medical conditions including cardiovascular diseases such as hypertension, heart failure and chronic kidney disease and conditions associated with excessive salt and water retention.

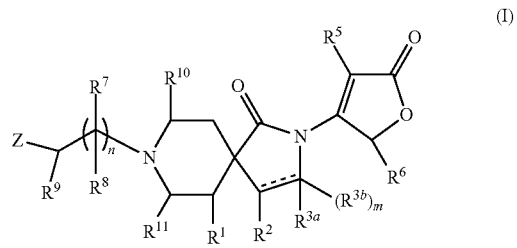

9 Claims, No Drawings

(56) References Cited

U.S. PATENT DOCUMENTS

| | | | |
|---|---|---|---|
| 9,751,881 B2 | 9/2017 | Tang et al. | |
| 9,777,002 B2 | 10/2017 | Walsh et al. | |
| 9,839,629 B2 | 12/2017 | Dong et al. | |
| 9,850,245 B2 | 12/2017 | Pasternak et al. | |
| 9,862,720 B2 | 1/2018 | Ding et al. | |
| 9,951,052 B2 | 4/2018 | Pasternak et al. | |
| 2007/0275990 A1 | 11/2007 | Ohmoto et al. | |
| 2011/0224231 A1* | 9/2011 | Brodney | C07D 471/10 514/255.05 |
| 2014/0031349 A1* | 1/2014 | Ding | A61K 31/435 514/230.5 |

FOREIGN PATENT DOCUMENTS

| | | |
|---|---|---|
| WO | 2014150132 A1 | 9/2014 |
| WO | WO2016008064 A1 | 1/2016 |
| WO | WO2016010801 A1 | 1/2016 |
| WO | WO2016010802 A1 | 1/2016 |
| WO | 2016060941 A1 | 4/2016 |
| WO | 2016069428 A1 | 5/2016 |
| WO | 2016069430 A1 | 5/2016 |
| WO | 2016122994 A1 | 8/2016 |
| WO | 2016130444 A1 | 8/2016 |

OTHER PUBLICATIONS

Hebert, S. C. et al., Molecular Diversity and Regulation of Renal Potassium Channels, Physiol Rev., 2005, p. 319-371, vol. 85.

Ho, K. et al., Cloning and expression of an inwardly rectifying ATP-regulated potassium channel, Nature, 1993, p. 31-38, vol. 362.

Ji, W. et al., Rare independent mutations in renal salt handling genes contribute to blood pressure variation, Nature Genetics, 2008, p. 592-599, vol. 40, No. 5.

Lewis, L M., High-throughput screening reveals a small-molecule inhibitor of the Renal Outer Medullary Potassium Channel and Kir7.1, Mol. Phamcol., 2009, 1094-1103, 76.

Lifton, R. P. et al., Molecular Mechanisms of Human Hypertension, Cell, 2001, p. 545-556, vol. 104.

Lorenz, J. N. et al., Impaired Renal NaCl Absorption inMic Lacking the ROMK Potassium Cannel, a Model for Type II Bartters Syndrome, The Journal of Biological Chemistry, 2002, p. 37871-37880, vol. 277, No. 40.

Lu, M. et al., Absence of Small Conductance K+ Channel (SK) Activity in Apical Membranes of Thick Ascending Limb and Cortical Collectiong Duct in ROMK (Bartter's) Knockout Mice, The Journal of Biological Chemistry, 2002, p. 37881-37887, vol. 277, No. 40.

Molander, G. A. et al., Stereoselective Suzuki-Miyaura Cross-Coupling Reactions of Potassium Alkenyltrifluoroborates with Alkenyl Bromides, J. Org. Chem, 2005, p. 3950-3956, vol. 70.

Nomura, Y. et al., Synthesis and Structure-Activity Relationships of 2-(4-Benzhydry1-1-piperaziny1)-1-phenylethanols as New Calcium Blockers, Chem. Phar. Bull, 1995, p. 241-246, vol. 43, No. 2.

Reinalter, S. C. et al., Pharmacotyping of hypokalaemic salt-losing tubular disorders, Acta Physiol Scand, 2004, p. 513-521, vol. 181.

Shuck, M. E. et al., Cloning and Characterization of Multiple Forms of the Human Kidney ROM-K Potassium channel, The Journal of Biological Chemistry, 1994, p. 24261-24270, Vo. 269, No. 39.

Tobin, M. D. et al., Common Variants in Genes Underlying Monogenic Hypertension and Hypotension and Blood Pressure in the General Population, Hypertension, 2008, p. 1658-1664, vol. 51. No. 6.

Wang, W. et al., Renal potassium channesl: recent developments, Current Opinion in Nephrology and Hypertension, 2004, p. 549-555, vol. 13, No. 5.

Deng, Guanghui et al., Novel complex crystal structure of prolyl hydroxylase domain-containing protein 2 (PHD2): 2,8-Diazaspiro;4. 5]decan-1-ones as potent, orally bioavailable PHD2 inhibitors, Biooorganic & Medicinal Chemistry Letters, 2013, 6349-6358, 21.

Fritch et al., Design, syntheses, and SAR of 2,8-diazaspiro[4. 5]decanones at T-type calcium channel antagonists, Bioorganic & Medicinal Chemistry Letters, 2010, 6375-6378, 20.

International Search Report for PCT/CN2014/082119 dated Apr. 15, 2015; 17 pages.

International Search Report of PCT/US2015/039636 dated Oct. 7, 2015; 8 pages.

* cited by examiner

INHIBITORS OF THE RENAL OUTER MEDULLARY POTASSIUM CHANNEL

CROSS-REFERENCE TO RELATED APPLICATIONS

This application is a U.S. National Phase application under 35 U.S.C. § 371 of PCT Application No. PCT/US15/039635, filed on Jul. 9, 2015, which claims priority from and the benefit of Chinese PCT Patent Application PCT/CN14/082119, filed Jul. 14, 2014.

FIELD OF THE INVENTION

The present invention relates to novel spirocyclic compounds and salts thereof useful as renal outer medullary potassium channel inhibitors. The present invention further relates to compositions containing such compounds, and methods of use thereof.

BACKGROUND OF THE INVENTION

The Renal Outer Medullary Potassium (ROMK) channel (Kir1.1) (see e.g., Ho, K., et al., *Cloning and expression of an inwardly rectifying ATP-regulated potassium channel*, Nature, 1993, 362(6415): p. 31-8.1, 2; and Shuck, M. E., et al., *Cloning and characterization of multiple forms of the human kidney ROM-K potassium channel*, J Biol Chem, 1994, 269(39): p. 24261-70) is a member of the inward rectifier family of potassium channels expressed in two regions of the kidney: thick ascending loop of Henle (TALH) and cortical collecting duct (CCD) (see Hebert, S. C., et al., *Molecular diversity and regulation of renal potassium channels*, Physiol Rev, 2005, 85(1): p. 319-713). At the TALH, ROMK participates in potassium recycling across the luminal membrane which is critical for the function of the $Na^+/K^+/2Cl^-$ co-transporter, the rate-determining step for salt reuptake in this part of the nephron. At the CCD, ROMK provides a pathway for potassium secretion that is tightly coupled to sodium uptake through the amiloride-sensitive sodium channel (see Reinalter, S. C., et al., *Pharmacotyping of hypokalaemic salt-losing tubular disorders*, Acta Physiol Scand, 2004, 181(4): p. 513-21; and Wang, W., *Renal potassium channels: recent developments*, Curr Opin Nephrol Hypertens, 2004, 13(5): p. 549-55). Selective inhibitors of the ROMK channel (also referred to herein as inhibitors of ROMK or ROMK inhibitors) are expected to represent novel diuretics for the treatment of hypertension and other conditions where treatment with a diuretic would be beneficial with potentially reduced liabilities (i.e., hypo- or hyperkalemia, new onset of diabetes, dyslipidemia) over the currently used clinical agents (see Lifton, R. P., A. G. Gharavi, and D. S. Geller, *Molecular mechanisms of human hypertension*, Cell, 2001, 104(4): p. 545-56). Human genetics (Ji, W., et al., *Rare independent mutations in renal salt handling genes contribute to blood pressure variation*, Nat Genet, 2008, 40(5): p. 592-9; and Tobin, M. D., et al., *Common variants in genes underlying monogenic hypertension and hypotension and blood pressure in the general population*, Hypertension, 2008, 51(6): p. 1658-64) and genetic ablation of ROMK in rodents (see Lorenz, J. N., et al., *Impaired renal NaCl absorption in mice lacking the ROMK potassium channel, a model for type II Bartter's syndrome*, J Biol Chem, 2002, 277(40): p. 37871-80 and Lu, M., et al., *Absence of small conductance K+ channel (SK) activity in apical membranes of thick ascending limb and cortical collecting duct in ROMK (Bartter's) knockout mice*, J Biol Chem, 2002, 277(40): p. 37881-7) support these expectations. To our knowledge, the first publicly disclosed small molecule selective inhibitors of ROMK, including VU590, were reported from work done at Vanderbilt University as described in Lewis, L. M., et al., *High-Throughput Screening Reveals a Small-Molecule Inhibitor of the Renal Outer Medullary Potassium Channel and Kir7.1*, Mol Pharmacol, 2009, 76(5): p. 1094-1103. The compound VU591 was later reported in Bhave, G. et al., *Development of a Selective Small-Molecule Inhibitor of Kir1.1, the Renal Outer Medullary Potassium Channel*, Mol Pharmacol, 2011, 79(1), p. 42-50, the text of which states that "ROMK (Kir1.1), is a putative drug target for a novel class of loop diuretics that would lower blood pressure without causing hypokalemia."

Since then, numerous ROMK inhibitors have been described.

The continued discovery of selective small molecule inhibitors of ROMK is needed for the development of new treatments for hypertension, heart failure, edematous states and related disorders. The compounds of Formula I and salts thereof of this invention are selective inhibitors of the ROMK channel and could be used for the treatment of hypertension, heart failure and other conditions where treatment with a diuretic or natriuretic would be beneficial.

SUMMARY OF THE INVENTION

The present invention provides compounds of Formula I

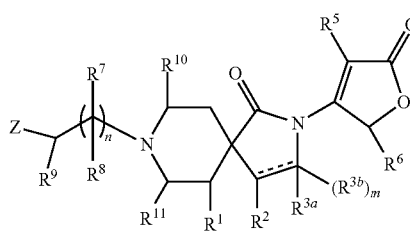

and pharmaceutically acceptable salts thereof. The compounds of Formula I are inhibitors of the ROMK (Kir1.1) channel. As a result, the compounds of Formula I could be used in methods of treatment, inhibition or amelioration of one or more disease states that could benefit from inhibition of ROMK. The compounds of this invention could be used in methods of treatment which comprise administering a therapeutically or prophylactically effective amount of a compound of Formula I to a patient in need of a diuretic and/or natriuretic agent. Therefore, the compounds of Formula I could be valuable pharmaceutically active compounds for the therapy, prophylaxis or both of medical conditions, including, but not limited to, cardiovascular diseases such as hypertension and heart failure as well as chronic kidney disease, and conditions associated with excessive salt and water retention. The compounds of this invention could further be used in combination with other therapeutically effective agents, including but not limited to, other drugs which are useful for the treatment of hypertension, heart failure and conditions associated with excessive salt and water retention. The invention furthermore relates to processes for preparing compounds of Formula I, and pharmaceutical compositions which comprise compounds of Formula I. These and other aspects of the invention will be evident from the description contained herein.

DETAILED DESCRIPTION OF THE INVENTION

The present invention addresses the following compounds, compounds of (1)-(34):

(1) A compound of formula I:

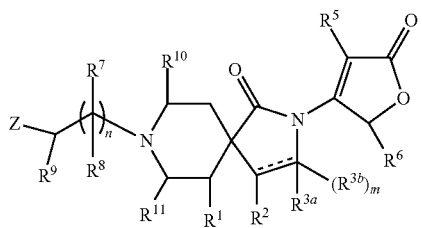

I or a pharmaceutically acceptable salt thereof wherein:
Z is:

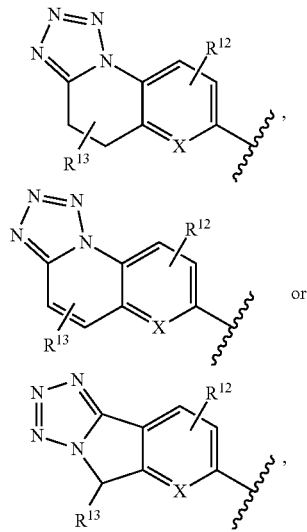

X is C(R⁴) or N;
R¹ is —H, halo, —OH, $C_{1-3}$alkyl or —O$C_{1-3}$alkyl;
R² is —H, =O (oxo), —OH, —$C_{1-3}$alkyl or —O$C_{1-3}$alkyl;
R$^{3a}$ is —H, —$C_{3-4}$cycloalkyl or —$C_{1-3}$alkyl optionally substituted with —OCH₃ or 1 to 3 of —F;
R$^{3b}$ is —H or —$C_{1-3}$ alkyl, or R$^{3b}$ is absent when the dashed bond is a double bond;
or R$^{3a}$ and R$^{3b}$ are joined together with the carbon to which they are both attached to form cyclopropyl or cyclobutyl;
R⁴ is —H, halo, —CN, —$C_{3-6}$cycloalkyl, —C(O)O$C_{1-4}$alkyl, —O$C_{1-4}$alkyl, or —$C_{1-4}$alkyl optionally substituted with OH or 1-3 of —F;
R⁵ is —H, halo, or —$C_{1-3}$alkyl optionally substituted with —O—$C_{1-3}$alkyl;
R⁶ is —H or —$C_{1-3}$alkyl;
R⁷ is —H or —$C_{1-3}$alkyl optionally substituted with —OH, —OCH₃ or 1 to 3 of —F, or R⁷ is absent when n is zero;
R⁸ is —H or —$C_{1-3}$alkyl, or R⁸ is absent when n is zero;
or R⁷ and R⁸ are joined together with the carbon to which they are both attached to form cyclopropyl or cyclobutyl;
R⁹ is —H, halo, —OH, —$C_{1-3}$ alkyl, —O$C_{1-3}$ alkyl or —CH₂OH;
R¹⁰ is —H, or —$C_{1-3}$alkyl optionally substituted with —OH, —OCH₃, or 1 to 3 of —F;
R¹¹ is —H, or —$C_{1-3}$alkyl optionally substituted with —OH, —OCH₃, or 1 to 3 of —F;
or R¹⁰ and R¹¹ are joined together to represent —CH₂—CH₂—, —CH₂—N(CH₃)—CH₂— or —CH₂OCH₂—;
R¹² and R¹³ are each independently —H, halo, —CN, —$C_{3-6}$cycloalkyl, —C(O)O$C_{1-4}$alkyl, —O$C_{1-4}$alkyl, or —$C_{1-4}$alkyl optionally substituted with —OH or 1-3 of —F;
m is zero where R$^{3b}$ is absent, or one where R$^{3b}$ is present;
the partially dashed double bond ("---") represents a single or double bond wherein:
(i) when m is one, then the dashed bond is a single bond; and
(ii) when m is zero and R² is not =O, then the dashed bond is a double bond; and
n is zero or one.

(2) A compound of formula I having structural Formula Ia or a pharmaceutically acceptable salt thereof:

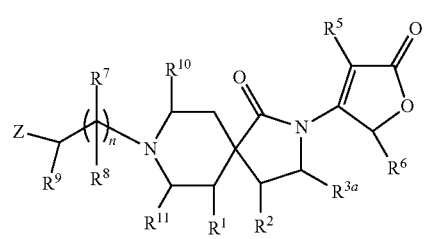

Ia wherein each of the variables n, Z, R¹, R², R$^{3a}$, R⁵, R⁶, R⁷, R⁸, R⁹, R¹⁰, R¹¹, and all other variables therein are as defined above in Formula I.

(3) A compound of formula I having structural Formula Ia or a pharmaceutically acceptable salt thereof wherein:
Z is:

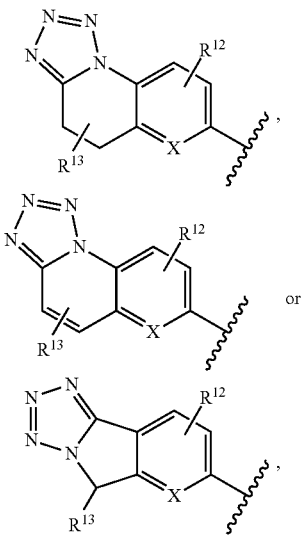

X is C(R$^4$) or N;
R$^1$ is —H, halo, —OH, C$_{1-3}$alkyl or —OC$_{1-3}$alkyl;
R$^2$ is —H, =O (oxo), —OH, —C$_{1-3}$alkyl or —OC$_{1-3}$alkyl;
R$^{3a}$ is —H, —C$_{3-4}$cycloalkyl or —C$_{1-3}$ alkyl optionally substituted with —OCH$_3$ or 1 to 3 of —F;
R$^4$ is —H, halo, —CN, —C$_{3-6}$ cycloalkyl, —C(O)OC$_{1-4}$ alkyl, —OC$_{1-4}$ alkyl, or —C$_{1-4}$ alkyl optionally substituted with OH or 1-3 of —F;
R$^5$ is —H, halo, or —C$_{1-3}$alkyl optionally substituted with —O—C$_{1-3}$alkyl;
R$^6$ is —H or —C$_{1-3}$alkyl;
R$^7$ is —H or —C$_{1-3}$alkyl optionally substituted with —OH, —OCH$_3$ or 1 to 3 of —F, or R$^7$ is absent when n is zero;
R$^8$ is —H or —C$_{1-3}$alkyl, or R$^8$ is absent when n is zero;
R$^9$ is —H, halo, —OH, —C$_{1-3}$alkyl, —OC$_{1-3}$ alkyl or —CH$_2$OH;
R$^{10}$ is —H, or —C$_{1-3}$alkyl optionally substituted with —OH, —OCH$_3$, or 1 to 3 of —F;
R$^{11}$ is —H, or —C$_{1-3}$alkyl optionally substituted with —OH, —OCH$_3$, or 1 to 3 of —F;
R$^{12}$ and R$^{13}$ are each independently —H, halo, —CN, —C$_{3-6}$cycloalkyl, —C(O))OC$_{1-4}$alkyl, —OC$_{1-4}$alkyl, or —C$_{1-4}$alkyl optionally substituted with —OH or 1-3 of —F; and
n is zero or one.

(4) The compound of any of (1)-(3), or a pharmaceutically acceptable salt thereof, wherein:
Z is:

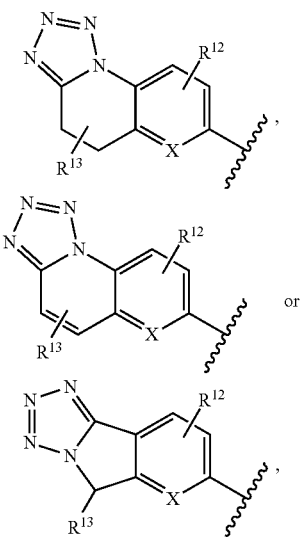

X is C(R$^4$) or N;
R$^1$ is —H, halo, —OH, C$_{1-3}$alkyl or —OC$_{1-3}$alkyl;
R$^2$ is —H, =O (oxo), —OH, —C$_{1-3}$alkyl or —OC$_{1-3}$alkyl;
R$^{3a}$ is —H, —C$_{3-4}$cycloalkyl or —C$_{1-3}$alkyl optionally substituted with —OCH$_3$ or 1 to 3 of —F;
R$^4$ is —H, halo or —C$_{1-4}$alkyl optionally substituted with OH or 1-3 of —F;
R$^5$ is —H, halo, or —C$_{1-3}$alkyl optionally substituted with —O—C$_{1-3}$alkyl;
R$^6$ is —H or —C$_{1-3}$alkyl;
R$^7$ is —H or —C$_{1-3}$alkyl, or R$^7$ is absent when n is zero;
R$^8$ is —H, or R$^8$ is absent when n is zero;
R$^9$ is —H, —F, —OH, —C$_{1-3}$alkyl, —OC$_{1-3}$alkyl or —CH$_2$OH;
R$^{10}$ is —H or —C$_{1-3}$alkyl;
R$^{11}$ is —H or —C$_{1-3}$alkyl;
R$^{12}$ and R$^{13}$ are each independently —H, halo, —C$_{3-6}$cycloalkyl, or —C$_{1-4}$alkyl optionally substituted with —OH or 1-3 of —F; and
n is zero or one.

(5) The compound of any of (1)-(4), or a pharmaceutically acceptable salt thereof, wherein:
R$^1$ is —H or halo;
R$^2$ is —H;
R$^{3a}$ is —H or —C$_{1-3}$alkyl optionally substituted with —OCH$_3$ or 1 to 3 of —F;
R$^4$ is —H, halo, or —C$_{1-4}$alkyl;
R$^5$ is —H or —C$_{1-3}$alkyl;
R$^6$ is —H;
R$^7$ is —H, or R$^7$ is absent when n is zero;
R$^8$ is —H, or R$^8$ is absent when n is zero;
R$^9$ is —H, —F, —OH, —C$_{1-3}$ alkyl, —OC$_{1-3}$ alkyl or —CH$_2$OH;
R$^{10}$ is —H;
R$^{11}$ is H;
R$^{12}$ is —H, cyclopropyl, or —C$_{1-4}$alkyl optionally substituted with 1-3 of —F;
R$^{13}$ is —H, or —C$_{1-4}$alkyl optionally substituted with 1-3 of —F; and
n is zero or one.

(6) The compound of any of (1)-(5), or a pharmaceutically acceptable salt thereof, wherein Z is:

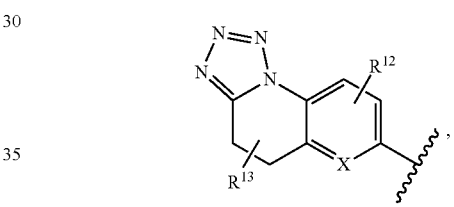

wherein R$^{12}$ and R$^{13}$ are are as defined therein.

(7) The compound of any of (1)-(5), or a pharmaceutically acceptable salt thereof, wherein Z is:

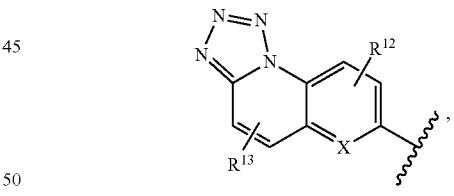

wherein R$^{12}$ and R$^{13}$ are are as defined therein.

(8) The compound of any of (1)-(5), or a pharmaceutically acceptable salt thereof, wherein Z is:

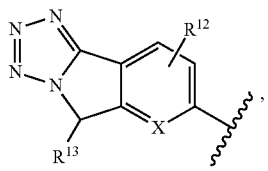

wherein R$^{12}$ and R$^{13}$ are are as defined therein.

(9) The compound of any of (1)-(5), or a pharmaceutically acceptable salt thereof, wherein Z is:

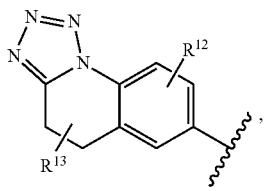

wherein R$^{12}$ and R$^{13}$ are are as defined therein.

(10) The compound of any of (1)-(5), or a pharmaceutically acceptable salt thereof, wherein Z is:

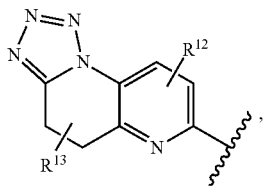

wherein R$^{12}$ and R$^{13}$ are are as defined therein.

(11) The compound of any of (1)-(5), or a pharmaceutically acceptable salt thereof, wherein Z is:

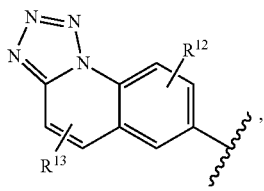

wherein R$^{12}$ and R$^{13}$ are are as defined therein.

(12) The compound of any of (1)-(5), or a pharmaceutically acceptable salt thereof, wherein Z is:

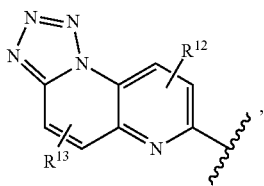

wherein R$^{12}$ and R$^{13}$ are are as defined therein.

(13) The compound of any of (1)-(5), or a pharmaceutically acceptable salt thereof, wherein Z is:

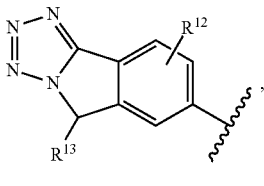

wherein R$^{12}$ and R$^{13}$ are are as defined therein.

(14) The compound of any of (1)-(4) and (6)-(13), or a pharmaceutically acceptable salt thereof, wherein R$^1$ is H, —CH$_3$ or F, and more particularly it is —H or —F.

(15) The compound of any of (1)-(14), or a pharmaceutically acceptable salt thereof, wherein R$^1$ is —H.

(16) The compound of any of (1)-(4) and (6)-(15), or a pharmaceutically acceptable salt thereof, wherein R$^2$ is —H, —OH, =O, —CH$_3$ or —OCH$_3$.

(17) The compound of any of (1)-(16), or a pharmaceutically acceptable salt thereof, wherein R$^2$ is —H.

(18) The compound of any of (1)-(4) and (6)-(17), or a pharmaceutically acceptable salt thereof, wherein R$^{3a}$ is —H, —C$_{1-3}$alkyl, or cyclopropyl.

(19) The compound of any of (1)-(18), or a pharmaceutically acceptable salt thereof, wherein R$^{3a}$ is —H or —CH$_3$.

(20) The compound of (1), or a pharmaceutically acceptable salt thereof, wherein R$^{3b}$ is —H or —C$_{1-3}$alkyl.

(21) The compound of (1), or a pharmaceutically acceptable salt thereof, wherein R$^{3b}$ is —H or absent when the dashed double bond is a double bond.

(22) The compound of any of (1)-(21), or a pharmaceutically acceptable salt thereof, wherein R$^4$ is —H, —F, —Cl or —C$_{1-3}$alkyl optionally substituted with —OH or 1-3 of —F, and particularly each R$^4$ is —H, —Cl or —CH$_3$. In particular embodiments, R$^4$ is —H.

(23) The compound of any of (1)-(4) and (6)-(22), or a pharmaceutically acceptable salt thereof, wherein R$^5$ is —H, halo particularly —F or —Cl, or —C$_{1-3}$alkyl, and more particularly it is —H or —CH$_3$.

(24) The compound of any of (1)-(4) and (6)-(23), or a pharmaceutically acceptable salt thereof, wherein R$^6$ is —H or —CH$_3$, and more particularly it is —H.

(25) The compound of any of (1)-(3) and (6)-(24), or a pharmaceutically acceptable salt thereof, wherein R$^7$, when present, is —H or —CH$_3$, and more particularly it is —H or —CH$_3$.

(26) The compound of any of (1)-(3) and (6)-(25), or a pharmaceutically acceptable salt thereof, wherein R$^8$, when present, is —H or —CH$_3$, more particularly it is —H.

(27) The compound of any of (1)-(26), or a pharmaceutically acceptable salt thereof, wherein R$^9$ is —H, —OH, —OCH$_3$ or —CH$_2$OH, or particularly —H or —OH, or more particularly —OH.

(28) The compound of any of (1)-(3) and (6)-(27), or a pharmaceutically acceptable salt thereof, wherein R$^{10}$ is —H, —CH$_2$OH, —CH$_2$OCH$_3$, or —C$_{1-3}$alkyl optionally substituted with 1 to 3 of —F, or particularly —H or —CH$_3$, or more particularly, —H.

(29) The compound of any of (1)-(3) and (6)-(28), or a pharmaceutically acceptable salt thereof, wherein R$^{11}$ is —H, —CH$_2$OH, —CH$_2$OCH$_3$, or —C$_{1-3}$alkyl optionally substituted with 1 to 3 of —F, or more particularly, —H.

(30) The compound of any of (1)-(29), or a pharmaceutically acceptable salt thereof, wherein R$^{12}$ is —H or cyclopropyl, and R$^{13}$ is —H or —CH$_3$.

(31) The compound of any of (1)-(30), or a pharmaceutically acceptable salt thereof, wherein n is one.

(32) The compound of any of (1)-(24) and (27)-(30), or a pharmaceutically acceptable salt thereof, wherein n is zero.

(33) A compound of formula I which is elsewhere disclosed herein or is:
8-(2-(6-chloro-5H-tetrazolo[5,1-a]isoindol-7-yl)-2-hydroxyethyl)-2-(4-methyl-5-oxo-2,5-dihydrofuran-3-yl)-2,8-diazaspiro[4.5]decan-1-one;
6-fluoro-8-(2-hydroxy-2-(5H-tetrazolo[5,1-a]isoindol-7-yl)ethyl)-2-(4-methyl-5-oxo-2,5-dihydrofuran-3-yl)-2,8-diazaspiro[4.5]decan-1-one;
8-(2-(4,5-dihydrotetrazolo[1,5-a]quinolin-7-yl)-2-hydroxyethyl)-2-(4-methyl-5-oxo-2,5-dihydrofuran-3-yl)-2,8-diazaspiro[4.5]decan-1-one;

8-(2-hydroxy-2-(5H-tetrazolo[5,1-a]isoindol-7-yl)ethyl)-2-(4-methyl-5-oxo-2,5-dihydrofuran-3-yl)-2,8-diazaspiro[4.5]decan-1-one;
8-(2-hydroxy-2-(6-methyl-4,5-dihydrotetrazolo[1,5-a]quinolin-7-yl)ethyl)-2-(4-methyl-5-oxo-2,5-dihydrofuran-3-yl)-2,8-diazaspiro[4.5]decan-1-one;
8-(2-(4,5-dihydrotetrazolo[1,5-a]quinolin-7-yl)-2-hydroxyethyl)-3-methyl-2-(5-oxo-2,5-dihydrofuran-3-yl)-2,8-diazaspiro[4.5]decan-1-one;
8-(2-hydroxy-2-(tetrazolo[1,5-a]quinolin-7-yl)ethyl)-3-methyl-2-(5-oxo-2,5-dihydrofuran-3-yl)-2,8-diazaspiro[4.5]decan-1-one;
8-(2-hydroxy-2-(tetrazolo[1,5-a]quinolin-7-yl)ethyl)-2-(4-methyl-5-oxo-2,5-dihydrofuran-3-yl)-2,8-diazaspiro[4.5]decan-1-one;
8-(2-hydroxy-2-(tetrazolo[1,5-a][1,5]naphthyridin-7-yl)ethyl)-2-(4-methyl-5-oxo-2,5-dihydrofuran-3-yl)-2,8-diazaspiro[4.5]decan-1-one;
8-(2-hydroxy-2-(6-methyl-5H-tetrazolo[5,1-a]isoindol-7-yl)ethyl)-2-(4-methyl-5-oxo-2,5-dihydrofuran-3-yl)-2,8-diazaspiro[4.5]decan-1-one;
8-(2-(8-cyclopropyl-5H-tetrazolo[5,1-a]isoindol-7-yl)-2-hydroxyethyl)-2-(4-methyl-5-oxo-2,5-dihydrofuran-3-yl)-2,8-diazaspiro[4.5]decan-1-one;
8-(2-hydroxy-2-(5-methyl-5H-tetrazolo[5,1-a]isoindol-7-yl)ethyl)-2-(4-methyl-5-oxo-2,5-dihydrofuran-3-yl)-2,8-diazaspiro[4.5]decan-1-one;
8-(2-hydroxy-1-(tetrazolo[1,5-a]quinolin-7-yl)ethyl)-2-(4-methyl-5-oxo-2,5-dihydrofuran-3-yl)-2,8-diazaspiro[4.5]decan-1-one;
8-(1-(4,5-dihydrotetrazolo[1,5-a]quinolin-7-yl)-2-hydroxyethyl)-2-(4-methyl-5-oxo-2,5-dihydrofuran-3-yl)-2,8-diazaspiro[4.5]decan-1-one;
8-(2-(5H-tetrazolo[5,1-a]isoindol-7-yl)ethyl)-2-(4-methyl-5-oxo-2,5-dihydrofuran-3-yl)-2,8-diazaspiro[4.5]decan-1-one;
8-(2-methoxy-2-(5H-tetrazolo[5,1-a]isoindol-7-yl)ethyl)-2-(4-methyl-5-oxo-2,5-dihydrofuran-3-yl)-2,8-diazaspiro[4.5]decan-1-one;
or a pharmaceutically acceptable salt thereof.

(34) A compound of formula I which is elsewhere disclosed herein or is:
(R)-8-(2-(6-chloro-5H-tetrazolo[5,1-a] isoindol-7-yl)-2-hydroxyethyl)-2-(4-methyl-5 -oxo-2,5 -dihydrofuran-3 -yl)-2,8-diazaspiro[4.5]decan-1-one;
(S)-8-(2-(6-chloro-5H-tetrazolo[5,1-a]isoindol-7-yl)-2-hydroxyethyl)-2-(4-methyl-5-oxo-2,5-dihydrofuran-3-yl)-2,8-diazaspiro[4.5]decan-1-one;
(5S,6R)-6-fluoro-8-((R)-2-hydroxy-2-(5H-tetrazolo[5,1-a]isoindol-7-yl)ethyl)-2-(4-methyl-5-oxo-2,5-dihydrofuran-3-yl)-2,8-diazaspiro[4.5]decan-1-one;
(5R,6S)-6-fluoro-8-((R)-2-hydroxy-2-(5H-tetrazolo[5,1-a]isoindol-7-yl)ethyl)-2-(4-methyl-5-oxo-2,5-dihydrofuran-3-yl)-2,8-diazaspiro[4.5]decan-1-one;
(5R,6S)-6-fluoro-8-((R)-2-hydroxy-2-(5H-tetrazolo[5,1-a]isoindol-7-yl)ethyl)-2-(4-methyl-5-oxo-2,5-dihydrofuran-3-yl)-2,8-diazaspiro[4.5]decan-1-one;
(5S,6R)-6-fluoro-8-((S)-2-hydroxy-2-(5H-tetrazolo[5,1-a]isoindol-7-yl)ethyl)-2-(4-methyl-5-oxo-2,5-dihydrofuran-3-yl)-2,8-diazaspiro[4.5]decan-1-one;
(R)-8-(2-(4,5-dihydrotetrazolo[1,5 -a]quinolin-7-yl)-2-hydroxyethyl)-2-(4-methyl-5-oxo-2,5-dihydrofuran-3-yl)-2,8-diazaspiro[4.5]decan-1-one;
(R)-8-(2-(4,5-dihydrotetrazolo[1,5-a]quinolin-7-yl)-2-hydroxyethyl)-2-(4-methyl-5 -oxo-2,5 -dihydrofuran-3 -yl)-2,8-diazaspiro[4.5]decan-1-one;
(S)-8-(2-hydroxy-2-(5H-tetrazolo[5,1-a]isoindol-7-yl)ethyl)-2-(4-methyl-5-oxo-2,5-dihydrofuran-3-yl)-2,8-diazaspiro[4.5]decan-1-one;
(R)-8-(2-hydroxy-2-(5H-tetrazolo[5,1-a]isoindol-7-yl)ethyl)-2-(4-methyl-5 -oxo-2,5 -dihydrofuran-3 -yl)-2,8-diazaspiro[4.5]decan-1-one;
(S)-8-(2-hydroxy-2-(6-methyl-4,5-dihydrotetrazolo[1,5-a]quinolin-7-yl)ethyl)-2-(4-methyl-5-oxo-2,5-dihydrofuran-3-yl)-2,8-diazaspiro[4.5]decan-1-one;
(S)-8-(2-hydroxy-2-(6-methyl-4,5-dihydrotetrazolo[1,5-a]quinolin-7-yl) ethyl)-2-(4-methyl-5-oxo-2,5-dihydrofuran-3-yl)-2,8-diazaspiro[4.5]decan-1-one;
(R)-8-((R)-2-(4,5-dihydrotetrazolo[1,5-a]quinolin-7-yl)-2-hydroxyethyl)-3-methyl-2-(5-oxo-2,5-dihydrofuran-3-yl)-2,8-diazaspiro[4.5]decan-1-one;
(S)-8-((R)-2-(4,5-dihydrotetrazolo[1,5-a]quinolin-7-yl)-2-hydroxyethyl)-3-methyl-2-(5-oxo-2,5-dihydrofuran-3-yl)-2,8-diazaspiro[4.5]decan-1-one;
(R)-8-((S)-2-(4,5-dihydrotetrazolo[1,5-a]quinolin-7-yl)-2-hydroxyethyl)-3-methyl-2-(5-oxo-2,5-dihydrofuran-3-yl)-2,8-diazaspiro[4.5]decan-1-one;
(S)-8-((S)-2-(4,5-dihydrotetrazolo[1,5-a]quinolin-7-yl)-2-hydroxyethyl)-3-methyl-2-(5-oxo-2,5-dihydrofuran-3-yl)-2,8-diazaspiro[4.5]decan-1-one;
(R)-8-((R)-2-hydroxy-2-(tetrazolo[1,5-a]quinolin-7-yl)ethyl)-3-methyl-2-(5-oxo-2,5-dihydrofuran-3-yl)-2,8-diazaspiro[4.5]decan-1-one;
(S)-8-((R)-2-hydroxy-2-(tetrazolo[1,5-a]quinolin-7-yl)ethyl)-3-methyl-2-(5-oxo-2,5-dihydrofuran-3-yl)-2,8-diazaspiro[4.5]decan-1-one;
(R)-8-((S)-2-hydroxy-2-(tetrazolo[1,5-a]quinolin-7-yl)ethyl)-3-methyl-2-(5-oxo-2,5-dihydrofuran-3-yl)-2,8-diazaspiro[4.5]decan-1-one;
(S)-8-((S)-2-hydroxy-2-(tetrazolo[1,5-a]quinolin-7-yl)ethyl)-3-methyl-2-(5-oxo-2,5-dihydrofuran-3-yl)-2,8-diazaspiro[4.5]decan-1-one;
(R)-8-(2-hydroxy-2-(tetrazolo[1,5-a]quinolin-7-yl)ethyl)-2-(4-methyl-5-oxo-2,5-dihydrofuran-3-yl)-2,8-diazaspiro[4.5]decan-1-one;
(S)-8-(2-hydroxy-2-(tetrazolo[1,5-a]quinolin-7-yl)ethyl)-2-(4-methyl-5-oxo-2,5-dihydrofuran-3-yl)-2,8-diazaspiro[4.5]decan-1-one;
(R)-8-(2-hydroxy-2-(tetrazolo[1,5-a][1,5]naphthyridin-7-yl)ethyl)-2-(4-methyl-5-oxo-2,5-dihydrofuran-3-yl)-2,8-diazaspiro[4.5]decan-1-one;
(R)-8-(2-hydroxy-2-(6-methyl-5H-tetrazolo[5,1-a]isoindol-7-yl)ethyl)-2-(4-methyl-5-oxo-2,5-dihydrofuran-3-yl)-2,8-diazaspiro[4.5]decan-1-one;
(S)-8-((S)-2-hydroxy-2-(tetrazolo[1,5-a]quinolin-7-yl)ethyl)-3-methyl-2-(5-oxo-2,5-dihydrofuran-3-yl)-2,8-diazaspiro[4.5]decan-1-one;
(R)-8-(2-hydroxy-2-(tetrazolo[1,5-a]quinolin-7-yl)ethyl)-2-(4-methyl-5-oxo-2,5-dihydrofuran-3-yl)-2,8-diazaspiro[4.5]decan-1-one;
(S)-8-(2-hydroxy-2-(tetrazolo[1,5-a]quinolin-7-yl)ethyl)-2-(4-methyl-5-oxo-2,5-dihydrofuran-3-yl)-2,8-diazaspiro[4.5]decan-1-one;
(R)-8-(2-hydroxy-2-(tetrazolo[1,5-a][1,5]naphthyridin-7-yl)ethyl)-2-(4-methyl-5-oxo-2,5-dihydrofuran-3-yl)-2,8-diazaspiro[4.5]decan-1-one;
(R)-8-(2-hydroxy-2-(6-methyl-5H-tetrazolo[5,1-a]isoindol-7-yl)ethyl)-2-(4-methyl-5-oxo-2,5-dihydrofuran-3-yl)-2,8-diazaspiro[4.5]decan-1-one;
(S)-8-(2-hydroxy-2-(6-methyl-5H-tetrazolo[5,1-a]isoindol-7-yl)ethyl)-2-(4-methyl-5-oxo-2,5-dihydrofuran-3-yl)-2,8-diazaspiro[4.5]decan-1-one;

(R)-8-(2-(8-cyclopropyl-5H-tetrazolo[5,1-a]isoindol-7-yl)-2-hydroxyethyl)-2-(4-methyl-5-oxo-2,5-dihydrofuran-3-yl)-2,8-diazaspiro[4.5]decan-1-one;
(S)-8-(2-(8-cyclopropyl-5H-tetrazolo[5,1-a]isoindol-7-yl)-2-hydroxyethyl)-2-(4-methyl-5-oxo-2,5-dihydrofuran-3-yl)-2,8-diazaspiro[4.5]decan-1-one;
8-(2-hydroxy-2-((S)-5-methyl-5H-tetrazolo[5,1-a]isoindol-7-yl)ethyl)-2-(4-methyl-5-oxo-2,5-dihydrofuran-3-yl)-2,8-diazaspiro[4.5]decan-1-one;
8-(2-hydroxy-2-((R)-5-methyl-5H-tetrazolo[5,1-a]isoindol-7-yl)ethyl)-2-(4-methyl-5-oxo-2,5-dihydrofuran-3-yl)-2,8-diazaspiro[4.5]decan-1-one;
8-((R)-2-hydroxy-2-((R)-5-methyl-5H-tetrazolo[5,1-a]isoindol-7-yl)ethyl)-2-(4-methyl-5-oxo-2,5-dihydrofuran-3-yl)-2,8-diazaspiro[4.5]decan-1-one;
8-((S)-2-hydroxy-2-((R)-5-methyl-5H-tetrazolo[5,1-a]isoindol-7-yl)ethyl)-2-(4-methyl-5-oxo-2,5-dihydrofuran-3-yl)-2,8-diazaspiro[4.5]decan-1-one;
8-(2-hydroxy-1-(tetrazolo[1,5-a]quinolin-7-yl)ethyl)-2-(4-methyl-5-oxo-2,5-dihydrofuran-3-yl)-2,8-diazaspiro[4.5]decan-1-one;
(S)-8-(2-hydroxy-1-(tetrazolo[1,5-a]quinolin-7-yl)ethyl)-2-(4-methyl-5-oxo-2,5-dihydrofuran-3-yl)-2,8-diazaspiro[4.5]decan-1-one;
8-(1-(4,5-dihydrotetrazolo[1,5-a]quinolin-7-yl)-2-hydroxyethyl)-2-(4-methyl-5-oxo-2,5-dihydrofuran-3-yl)-2,8-diazaspiro[4.5]decan-1-one;
8-(2-(5H-tetrazolo[5,1-a]isoindol-7-yl)ethyl)-2-(4-methyl-5-oxo-2,5-dihydrofuran-3-yl)-2,8-diazaspiro[4.5]decan-1-one;
(R)-8-(2-methoxy-2-(5H-tetrazolo[5,1-a]isoindol-7-yl)ethyl)-2-(4-methyl-5-oxo-2,5-dihydrofuran-3-yl)-2,8-diazaspiro[4.5]decan-1-one;
or a pharmaceutically acceptable salt thereof.

The compounds of the present invention are further described herein using the terms defined below unless otherwise specified.

"Alkyl", as well as other groups having the prefix "alk", such as alkoxy, and the like, means carbon chains which may be linear or branched, or combinations thereof, containing the indicated number of carbon atoms. Examples of alkyl groups include methyl, ethyl, propyl, isopropyl, butyl, sec- and tert-butyl, pentyl, hexyl, heptyl, octyl, nonyl and the like. In specific embodiments, alkyl means a linear or branched $C_{1-6}$ or $C_{1-3}$alkyl.

"Alkoxy" refers to an alkyl group linked to oxygen. In specific embodiments, alkoxy means a linear or branched $C_{1-6}$ or $C_{1-3}$alkoxy in which the point of attachment is at oxygen.

"Cycloalkyl" means a saturated cyclic hydrocarbon radical having the number of carbon atoms designated. Examples of cycloalkyl include cyclopropyl, cyclobutyl, cyclopentyl and cyclohexyl. In specific embodiments, cycloalkyl means a $C_{3-6}$ or $C_{3-4}$cycloalkyl. In particular embodiments, cycloalkyl means C3cycloalkyl (or cyclopropyl).

"Halogen" or "halo" includes fluorine, chlorine, bromine and iodine.

Unless expressly depicted or described otherwise, variables depicted in a structural formula with a "floating" bond, such as substituents $R^{12}$ and $R^{13}$ are permitted on any available carbon atom in the ring to which each is attached.

Substitution, where applicable, may be on any available carbon atom that results in a stable structure.

Also, number ranges where provided (e.g., 1-6) expressly include each and every number in that range as a discrete embodiment.

Atoms of the compounds described herein may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of any of (1)-(34). For example, different isotopic forms of hydrogen (H) include protium (1H) and deuterium (2H). Protium is the predominant hydrogen isotope found in nature. Enriching for deuterium may yield certain therapeutic advantages, such as increasing in vivo half-life or reducing dosage requirements, or may provide a compound useful as a standard for characterization of biological samples. Isotopically-enriched compounds of any of (1)-(34) described herein can be prepared without undue experimentation by conventional techniques well known to those skilled in the art or by processes analogous to those described in the Examples herein using appropriate isotopically-enriched reagents and/or intermediates.

Individual tautomers of the compounds of any of (1)-(34), as well as mixtures thereof, are encompassed herein. Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers.

Compounds described herein may contain an asymmetric center and may thus exist as enantiomers. Where the compounds according to the invention possess two or more asymmetric centers, they may additionally exist as diastereomers. When bonds to the chiral carbon are depicted as straight lines in the formulas of the invention, it is understood that both the (R) and (S) configurations of the chiral carbon, and hence both enantiomers and mixtures thereof, are embraced. The present invention includes all such possible stereoisomers as substantially pure resolved enantiomers, racemic mixtures thereof, as well as mixtures of diastereomers. Except where otherwise specified, the formulae encompassing compounds of the present invention are shown without a definitive stereochemistry at certain positions. The present invention therefore may be understood to include all stereoisomers of compounds of any of (1)-(34) and pharmaceutically acceptable salts thereof.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of any of (1)-(34) may be obtained by stereospecific synthesis using optically pure starting materials or reagents of known configuration.

Furthermore, some of the crystalline forms for compounds of the present invention may exist as polymorphs and as such are intended to be included in the present invention. In addition, some of the compounds of the instant invention may form solvates with water or common organic solvents. Solvates, and in particular, the hydrates of the compounds of any of (1)-(34) are also included in the present invention.

The term "pharmaceutically acceptable salt" refers to a salt prepared from pharmaceutically acceptable non-toxic bases or acids including inorganic bases or acids and organic bases or acids.

Salts of basic compounds encompassed within the term "pharmaceutically acceptable salt" refer to non-toxic salts of the compounds described herein which are generally prepared by reacting the free base with a suitable organic or inorganic acid. Representative salts of basic compounds described herein include, but are not limited to, the following: acetate, benzenesulfonate, benzoate, bicarbonate, bisulfate, bitartrate, borate, bromide, camsylate, carbonate, chloride, clavulanate, citrate, edetate, edisylate, estolate, esylate, formate, fumarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, palmitate, pamoate (embonate), pantothenate, phosphate/diphosphate, polygalacturonate, salicylate, stearate, sulfate, subacetate, succinate, tannate, tartrate, teoclate, tosylate, triethiodide and valerate. Furthermore, where the compounds described herein carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. In particular embodiments, the salt is selected from ammonium, calcium, magnesium, potassium, or sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

The compounds of Formula I according to the invention are inhibitors of ROMK, and therefore could be used as diuretic and/or natriuretic agents. ROMK inhibitors may be used to help to increase urination and increase urine volume and also to prevent or reduce reabsorption of sodium in the kidneys leading to increased excretion of sodium and water. Therefore, the compounds could be used for treatment or prophylaxis or both of disorders that benefit from increased excretion of water and sodium from the body. Accordingly, the compounds of this invention could be used in a method for inhibiting ROMK comprising administering a compound of Formula I in a ROMK-inhibitory effective amount to a patient in need thereof. This also encompasses the use of the compounds for inhibiting ROMK in a patient comprising administering a compound of claim 1 in a therapeutically effective amount to a patient in need of diueresis, natriuresis or both. The inhibition of ROMK by the compounds of Formula I can be examined, for example, in the Thallium Flux Assay described below. Moreover, this invention also relates to the use of the compounds of Formula I or salts thereof to validate in vitro assays, for example but not limited to the Thallium Flux Assay described herein.

The compounds of this invention could be used in a method for causing diuresis, natriuresis or both, comprising administering a compound of Formula I in a therapeutically effective amount to a patient in need thereof. Therefore, the compounds of Formula I of this invention could be used in methods for treatment of, prevention of or reduction of risk for developing medical conditions that benefit from increased excretion of water and sodium, such as but not limited to one or more of hypertension, such as essential hypertension (also known as primary or idiopathic hypertension) which is a form of hypertension for which no cause can be found, heart failure (which includes both acute heart failure and chronic heart failure, the latter also known as congestive heart failure) and/or other conditions associated with excessive salt and water retention. The compounds could also be used to treat hypertension which is associated with any of several primary diseases, such as renal, pulmonary, endocrine, and vascular diseases, including treatment of patients with medical conditions such as heart failure and/or chronic kidney disease. Furthermore, the compounds of Formula I could be used in methods for treatment of, prevention of or reduction of risk for developing one or more disorders such as pulmonary hypertension, particularly pulmonary arterial hypertension (PAH), cardiovascular disease, edematous states, diabetes mellitus, diabetes insipidus, postoperative volume overload, endothelial dysfunction, diastolic dysfunction, systolic dysfunction, stable and unstable angina pectoris, thromboses, restenosis, myocardial infarction, stroke, cardiac insufficiency, pulmonary hypertonia, atherosclerosis, hepatic cirrhosis, ascites, pre-eclampsia, cerebral edema, nephropathy, glomerulonephritis, nephrotic syndrome, acute kidney insufficiency, chronic kidney insufficiency (also referred to as chronic kidney disease, or more generally as renal impairment), acute tubular necrosis, hypercalcemia, idiopathic edema, Dent's disease, Meniere's disease, glaucoma, benign intracranial hypertension, and other conditions for which a diuretic or natriuretic or both would have therapeutic or prophylactic benefit. The compounds of the invention may be administered to a patient having, or at risk of having, one or more conditions for which a diuretic or natriuretic or both would have therapeutic or prophylactic benefit such as those described herein.

The compounds of Formula I may potentially have reduced liabilities (for example, hypo- or hyperkalemia, new onset of diabetes, dyslipidemia, etc.) over currently used clinical agents. Also the compounds may have reduced risk for diuretic tolerance, which can be a problem with long-term use of loop diuretics.

In general, compounds that are ROMK inhibitors can be identified as those compounds which, when tested, have an IC50 of 5 µM or less, particularly 1 µM or less, and more particularly 0.25 µM or less, in the Thallium Flux Assay, described in more detail further below.

The dosage amount of the compound to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I. A consideration of these factors is well within the purview of the ordinarily skilled clinician for the purpose of determining the therapeutically effective or prophylactically effective dosage amount needed to prevent, counter, or arrest the progress of the condition. It is expected that the compound will be administered chronically on a daily basis for a length of time appropriate to treat or prevent the medical condition relevant to the patient, including a course of therapy lasting days, months, years or the life of the patient.

In general, a daily dose of approximately 0.001 to 100 mg/kg, particularly 0.001 to 30 mg/kg, in particular 0.001 to 10 mg/kg (in each case mg per kg of bodyweight) is appropriate for administration to an adult weighing approximately 75 kg in order to obtain the desired results. The daily dose is particularly administered in a single dose or can be divided into several, for example two, three or four individual doses, and may be, for example but not limited to, 0.1 mg, 0.25 mg, 0.5 mg, 0.75 mg, 1 mg, 1.25 mg, 2 mg, 2.5 mg, 5 mg, 10 mg, 20 mg, 40 mg, 50 mg, 75 mg, 100 mg, 125 mg, 150 mg, 175 mg, 200 mg, etc., on a daily basis. In some cases, depending on the potency of the compound or the individual response, it may be necessary to deviate upwards or downwards from the given daily dose. Furthermore, the compound may be formulated for immediate or modified release such as extended or controlled release.

The term "patient" includes animals, particularly mammals and especially humans, who use the instant active agents for the prophylaxis or treatment of a medical condition. Administering of the drug to the patient includes both self-administration and administration to the patient by another person. The patient may be in need of treatment for an existing disease or medical condition, or may desire prophylactic treatment to prevent or reduce the risk for developing said disease or medical condition or developing long-term complications from a disease or medical condition.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician. A "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. The terms "preventing," "prevention," "prophylactic" and derivatives of these terms as used herein refer to administering a compound to a patient before the onset of clinical symptoms of a condition not yet present in the patient. It is understood that a specific daily dosage amount can simultaneously be both a therapeutically effective amount, e.g., for treatment of hypertension, and a prophylactically effective amount, e.g., for prevention or reduction of risk of myocardial infarction or prevention or reduction of risk for complications related to hypertension.

In the methods of treatment of this invention, the ROMK inhibitors may be administered via any suitable route of administration such as, for example, orally, parenterally, or rectally in dosage unit formulations containing conventional non-toxic pharmaceutically acceptable carriers, adjuvants and vehicles. The term parenteral as used herein includes subcutaneous injections, intravenous (IV), intramuscular, intrasternal injection or infusion techniques. Oral formulations are preferred for treatment of chronic indications such as hypertension or chronic heart failure, particularly solid oral dosage units such as pills, tablets or capsules, and more particularly tablets. IV dosing is preferred for acute treatment, for example for the treatment of acute heart failure.

This invention also provides pharmaceutical compositions comprised of a compound of Formula I and a pharmaceutically acceptable carrier which is comprised of one or more excipients or additives. An excipient or additive is an inert substance used to formulate the active drug ingredient. For oral use, the pharmaceutical compositions of this invention containing the active ingredient may be in forms such as pills, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Tablets contain the active ingredient in admixture with non-toxic pharmaceutically acceptable excipients which are suitable for the manufacture of tablets. The excipients may be for example, inert diluents, such as calcium carbonate, sodium carbonate, lactose, mannitol, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc.

Pharmaceutical compositions may also contain other customary additives, for example but not limited to, wetting agents, stabilizers, emulsifiers, dispersants, preservatives, sweeteners, colorants, flavorings, aromatizers, thickeners, buffer substances, solvents, solubilizers, agents for achieving a depot effect, salts for altering the osmotic pressure, coating agents or antioxidants. Oral immediate-release and time-controlled release dosage forms may be employed, as well as enterically coated oral dosage forms. Tablets may be uncoated or they may be coated by known techniques for aesthetic purposes, to mask taste or for other reasons. Coatings can also be used to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an anti-oxidant such as ascorbic acid. Syrups and elixirs may be formulated with sweetening agents, for example glycerol, propylene glycol, sorbitol or sucrose.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier. Furthermore, a therapeutically effective amount of a compound of this invention can be used for the preparation of a medicament useful for inhibiting ROMK, for causing diuresis and/or natriuresis, and/or for treating, preventing or reducing the risk for any of the medical conditions described herein, in dosage amounts described herein.

The amount of active compound of Formula I and/or its pharmaceutically acceptable salts in the pharmaceutical composition may be, for example but not limited to, from about 0.1 mg to 1 g, particularly 0.1 mg to about 200 mg, more particularly from about 0.1 mg to about 100 mg, and even more particularly from about 0.1 to about 50 mg, per dose on a free acid/free base weight basis, but depending on the type of the pharmaceutical composition, potency of the active ingredient and/or the medical condition being treated, it could also be lower or higher. Pharmaceutical compositions usually comprise about 0.5 to about 90 percent by weight of the active compound on a free acid/free base weight basis.

The compounds of Formula I inhibit ROMK. Due to this property, apart from use as pharmaceutically active compounds in human medicine and veterinary medicine, they can also be employed as a scientific tool or as aid for biochemical investigations in which such an effect on ROMK is intended, and also for diagnostic purposes, for example in the in vitro diagnosis of cell samples or tissue samples. The compounds of Formula I can also be employed as intermediates for the preparation of other pharmaceutically active compounds.

One or more additional pharmacologically active agents may be administered in combination with a compound of Formula I. The additional active agent (or agents) is intended to mean a medicinal compound that is different from the compound of Formula I, and which is a pharmaceutically active agent (or agents) that is active in the body, including pro-drugs, for example esterified forms, that convert to pharmaceutically active form after administration, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents). Examples of the one or more additional active agents which may be employed include but are not limited to thiazide-like diuretics, e.g., hydrochlorothiazide (HCTZ or HCT); angiotensin converting enzyme inhibitors (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); dual inhibitors of angiotensin converting enzyme (ACE) and neutral endopeptidase (NEP) such as omapatrilat, sampatrilat and fasidotril; angiotensin II receptor antagonists, also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g., olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®, etc.); potassium sparing diuretics such as amiloride HCl, spironolactone, epleranone, triamterene, each with or without HCTZ; carbonic anhydrase inhibitors, such as acetazolamide; neutral endopeptidase inhibitors (e.g., thiorphan and phosphoramidon); aldosterone antagonists; aldosterone synthase inhibitors; renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643); enalkrein; RO 42-5892; A 65317; CP 80794; ES 1005; ES 8891; SQ 34017; aliskiren (2(S),4(S),5(S),7(S)-N-(2-carbamoyl-2-methylpropyl)-5-amino-4-hydroxy-2,7-diisopropyl-8-[4-methoxy-3-(3-methoxy-propoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine, bepridil, nisoldipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); nitrates or nitric oxide donating compounds, e.g. isosorbide mononitrate; lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; phosphodiesterase-5 (PDE5) inhibitors such as sildenafil (Revatio, Viagra), tadalafil (Cialis, Adcirca) vardenafil HCl (Levitra); or with other drugs beneficial for the prevention or the treatment of the above-mentioned diseases including but not limited to diazoxide; and including the free-acid, free-base, and pharmaceutically acceptable salt forms, pro-drug forms (including but not limited to esters), and salts of pro-drugs of the above medicinal agents where chemically possible. Trademark names of pharmaceutical drugs noted above are provided for exemplification of the marketed form of the active agent(s); such pharmaceutical drugs could be used in a separate dosage form for concurrent or sequential administration with a compound of Formula I, or the active agent(s) therein could be used in a fixed dose drug combination including a compound of Formula I.

EXAMPLES

Several methods for preparing the compounds of this invention are described in the following Schemes and Examples. Starting materials and intermediates are purchased, made from known procedures, or as otherwise illustrated. Some frequently applied routes to the compounds of Formula I are also described by the Schemes as follows. In some cases the order of carrying out the the steps of reaction schemes may be varied to facilitate the reaction or to avoid unwanted reaction products. The "R" substituents in the Schemes correspond to the substituents defined in Formula I at the same positions on the structures. The ring structure:

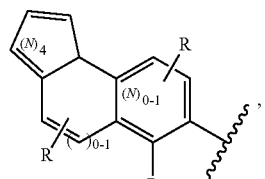

is intended to represent each of the individual groups of Z as defined in Formula I.

Compound 1.3, which is substituted at the benzylic position with an OH group, can be prepared following the sequence detailed in Scheme 1. Coupling of epoxides 1.1 to spirocyclic amines 1.2 at elevated temperatures leads to the formation of alcohols 1.3 as the major product and alcohols 1.4 as a minor side product (Nomura, Y. et al. Chemical & Pharmaceutical Bulletin, 1995, 43(2), 241-6). The reaction can be carried out with conventional heating, or by heating using a microwave apparatus. A number of solvents can be used in this reaction, for example, ethanol and 2-propanol. Spirocyclic amines may be free bases, or they may be salts, in which case a base such as triethylamine or N,N-diisopropylethylamine may be added. Note that when enantiomerically pure chiral epoxides are employed the epoxide opening occurs with retention of stereochemistry in the benzylic position and the individual isomer may be obtained. Alternatively, chiral HPLC separation of enantiomers or diastereomers of 1.3 or 1.4 may be performed to provide single enantiomers or diastereomers.

SCHEME 1

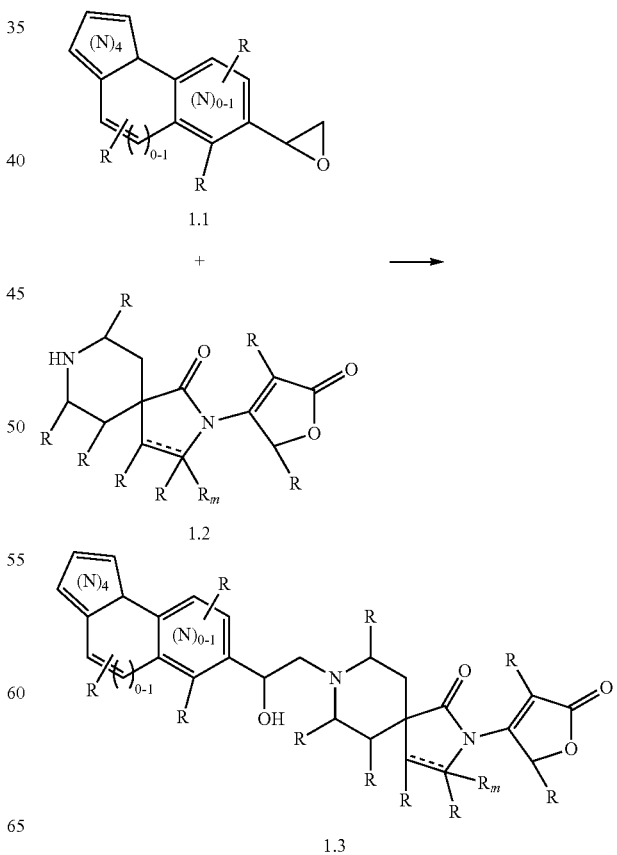

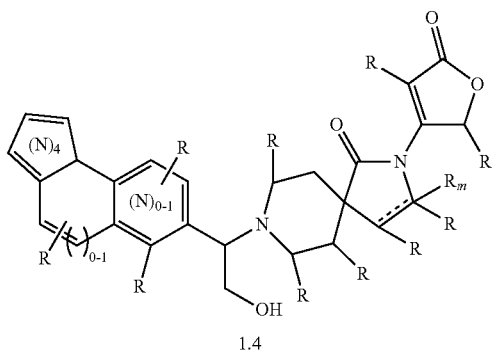

1.4

Compounds of formula 2.2 can be prepared by the sequence detailed in Scheme 2. Aldehydes or ketones 2.1 may be used in reductive alkylation reactions of spirocyclic amines 1.2 by using various reductive amination conditions (e.g., using sodium cyanoborohydride, sodium triacetoxy borohydride, or titanium tetra-isopropoxide, followed by sodium borohydride or sodium cyanoborohydride).

SCHEME 2

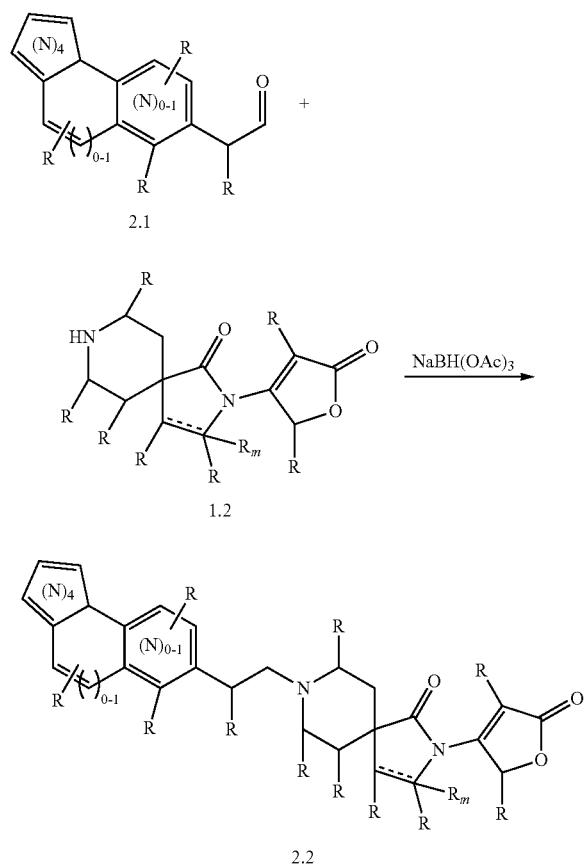

Spirocyclic amidofuranones 1.2 can be prepared as described in Scheme 3. Spirocyclic amino lactams 3.1 may be coupled to furanone triflates or bromides 3.2 using a palladium catalyst and ligand, for example palladium acetate and 4,5-bis(diphenylphosphino)-9,9-dimethylxanthene.

Some spirocyclic amino lactams 3.1 described herein are commercially available, others can be prepared as described in the experimental section below. 4-Bromofuran-2(5H)-one is commercially available, other furanones can be prepared as described in the examples below. Intermediates 3.3 are converted to spirocyclic amidofuranones 1.2 by removal of the protective group, for example, tert-butoxycarbonyl can be removed with TFA or HCl.

SCHEME 3

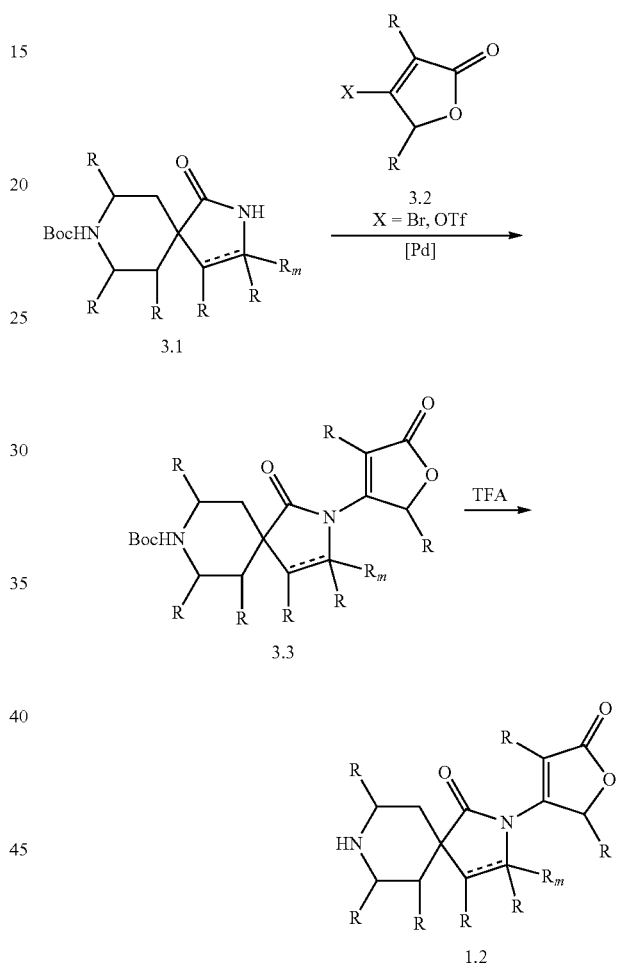

Spirocyclic amino lactams 4.4, can be prepared in numerous ways, including those described in Scheme 4. Commercially available aminoesters 4.1 can be alkylated with bromoacetonitrile 4.2 using a base such as lithium diisopropylamide to afford nitrile intermediates 4.3. Reduction, for example using hydrogenation in the presence of platinum oxide, or Raney Nickel, produces lactams 4.4. Alternatively, aminoesters 4.1 may be alkylated with allyl halides 4.5 using a base such as lithium diisopropylamide to furnish allyl intermediates 4.6. Oxidative cleavage, employing, for example, osmium tetraoxide and sodium periodate provides ketones or aldehydes 4.7. Reductive amination with tandem lactam cyclization to 4.4 can be accomplished in several ways, including by treatment with ammonium acetate and sodium cyanoborohydride in a solvent such as methanol, as shown.

SCHEME 4

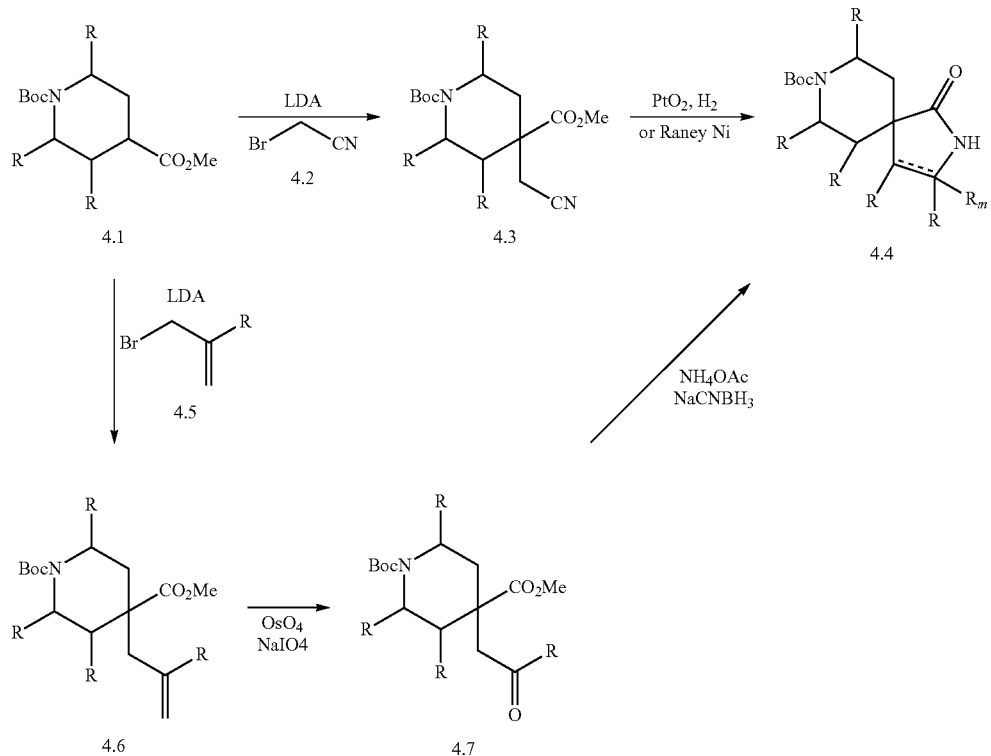

Scheme 5 shows preparation of spirocyclic furanone intermediates 5.5A and 5.5B. Commercially available aminoesters 5.1 can be alkylated with bromoacetonitrile using a base such as KHMDS to afford nitrile intermediates 5.2. Reduction, for example using platinum oxide and hydrogen, produces aminoalcohols 5.3, which was cyclized with ammonia in methanol to give lactams 5.4. Coupling of lactams 5.4 with furanone triflates or bromides using a palladium catalyst and ligand followed by column separation generates intermediates trans-isomers 5.5A and cis-isomers 5.5B.

SCHEME 5

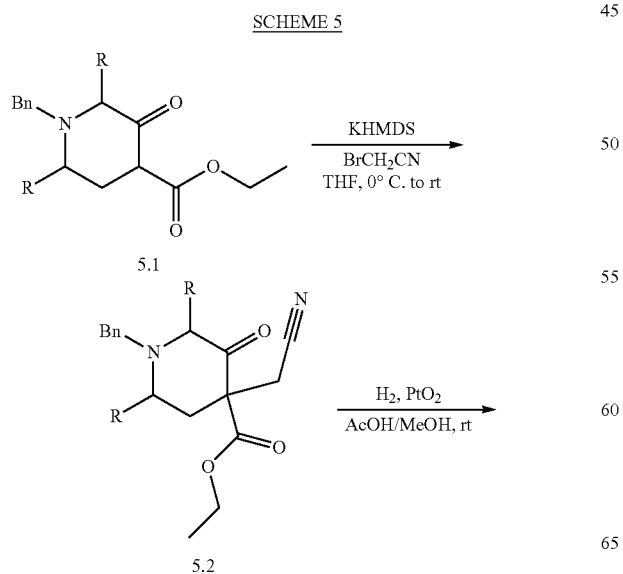

-continued

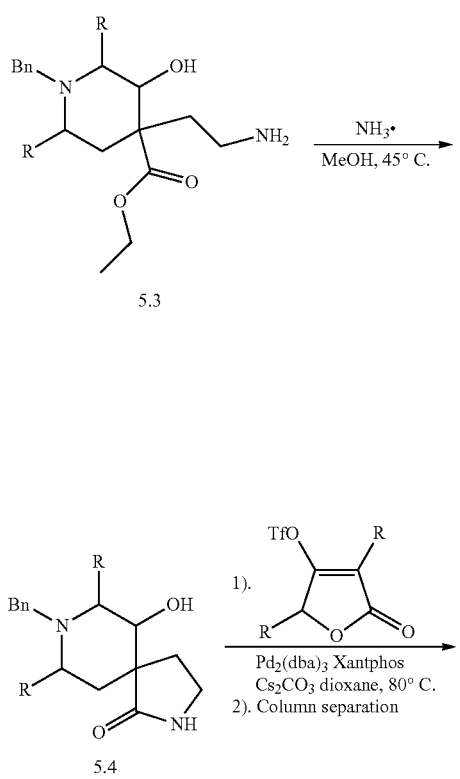

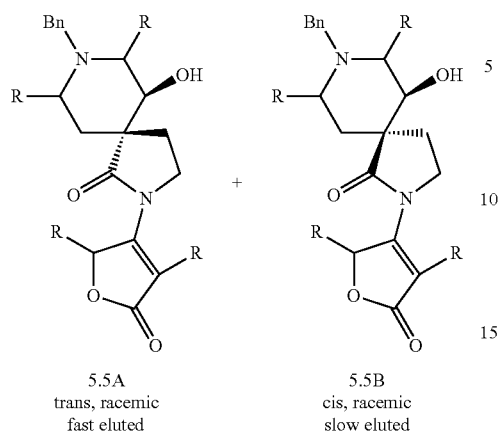

5.5A
trans, racemic
fast eluted 5.5B
cis, racemic
slow eluted

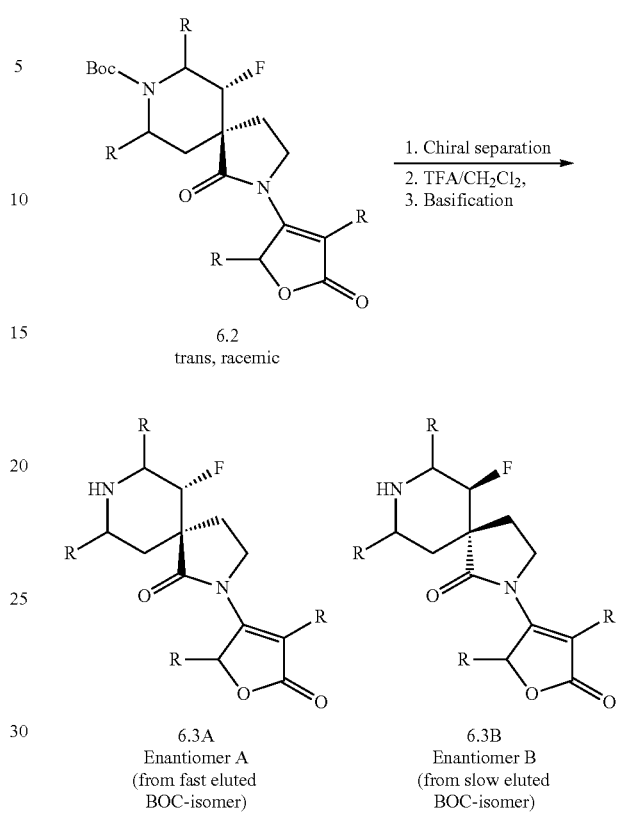

6.2
trans, racemic 6.3A
Enantiomer A
(from fast eluted BOC-isomer)

6.3B
Enantiomer B
(from slow eluted BOC-isomer)

Preparation of intermediates 6.3A and 6.3B is accomplished as described in Scheme 6. The benzyl-protection group in cis racemic alcohols 5.5B is replaced by a BOC group. The BOC-protected compounds of type 6.1 can then be transformed to trans-racemic fluorides 6.2 which are separated by chiral column, and subsequent deprotected of the BOC group with TFA in DCM to give intermediates of type 6.3.

SCHEME 6

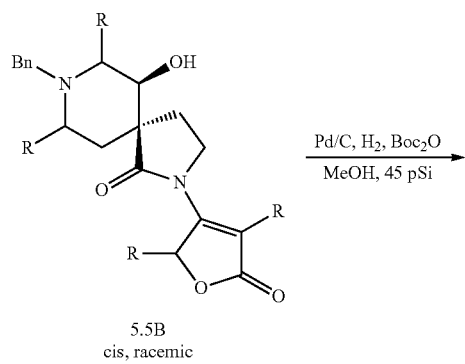

5.5B
cis, racemic

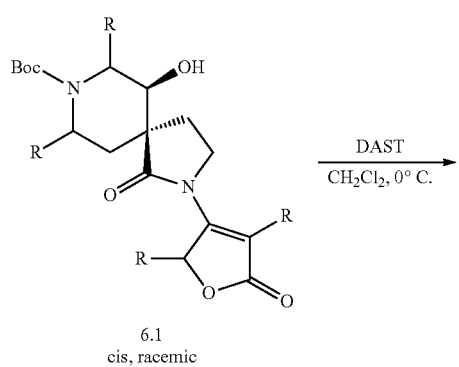

6.1
cis, racemic

Preparation of tetrazole-epoxide intermediates of type 1.1 may start from halo-substituted aniline 7.1 (Scheme 7). The epoxide ring in intermediate 1.1 can be built by treatment of 7.1 (where X is chloride, bromide, iodide, or trifluoromethane sulfonate) with potassium vinyl trifluoroborate (Molander, G.; Luciana, A. Journal of Organic Chemistry, 2005, 70(10), 3950-3956) under palladium catalyzed coupling conditions followed by epoxidation of the formed styrene (7.2) with NBS/NaOH. Alternatively, other methods for formation of styrene may be employed, for example, using vinylstannane reagents and palladium catalyst, and other methods for epoxidation of the styrene may use, for example, m-CPBA. The racemic epoxides of formula 1.1 can be resolved under chiral HPLC chromatography conditions to afford its enantiomers (R)-7.3A and (S)-7.3B.

SCHEME 7

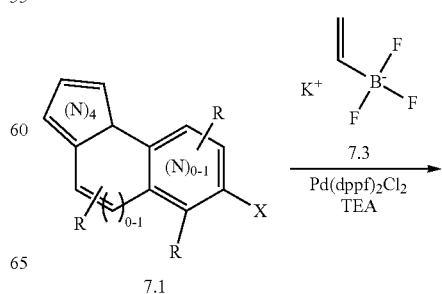

-continued

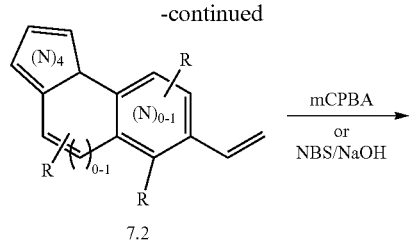

7.2

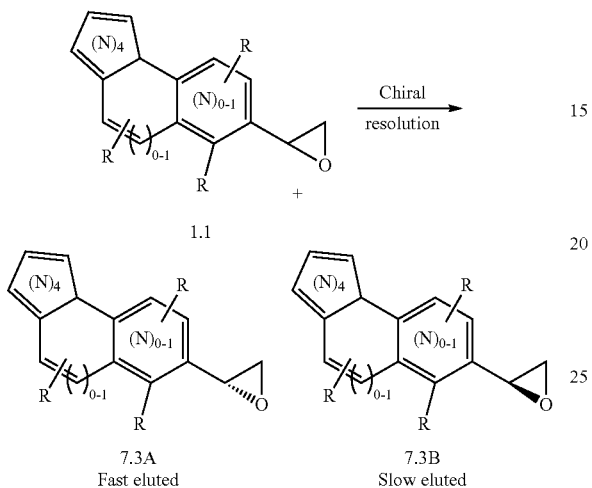

1.1

7.3A
Fast eluted 7.3B
Slow eluted

The formation of the tetrazole ring in tetrazolo[1,5-a]quinoline intermediates of type 8.2 can be accomplished by cyclization of 6-halo-substituted quinoline 8.1 or 6-halo-subsituted-2-chloroquinoline 8.3 (Scheme 8) with sodium azide at elevated temperature such as 130° C.

SCHEME 8

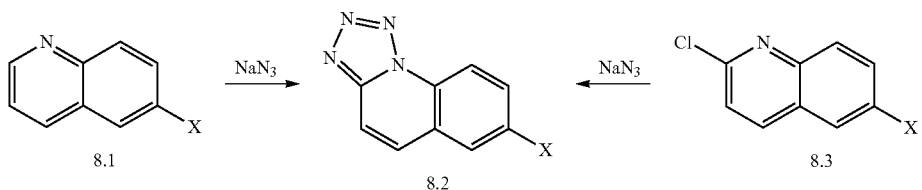

8.1            8.2            8.3

Formation of the tetrazole ring in substituted 4,5-dihydrotetrazolo[1,5-a]quinoline intermediates of type 9.2 can be achieved by incorporating azido group to substituted 3,4-dihydroquinolin-2(1H)-one under Mitsunobu condition followed by cylization in situ.

SCHEME 9

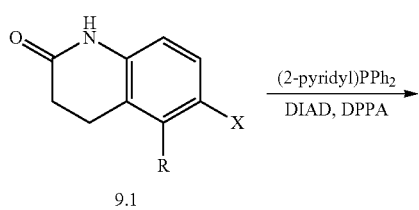

9.1

-continued

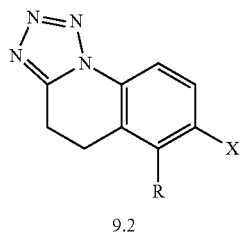

9.2

Preparation of substituted 5H-tetrazolo[5,1-a]isoindole intermediates 10.3 in scheme 10 may start from substituted 2-(bromomethyl)benzonitrile intermediates 10.1. Formation of C-linked tetrazole ring can be accomplished by intra molecular cylization of the azido and cyano groups in intermediates 10.2 at acidic condition. The azido group in intermediates 10.2 can be generated by $SN_2$ substitution of bromo group with sodium azide.

SCHEME 10

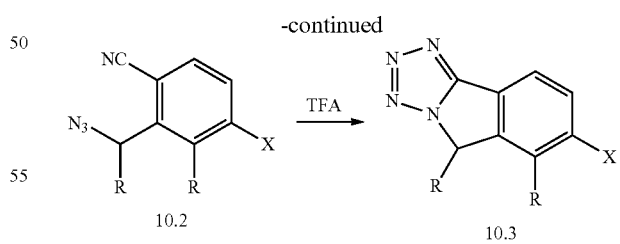

10.1

-continued 10.2            10.3

The independent synthesis of diastereomers and enantiomers or their chromatographic separations may be achieved as known in the art by appropriate modification of the methodology disclosed herein. Their absolute stereochemistry may be determined by x-ray crystallography of crystalline products or crystalline intermediates which are derivatized, if necessary, with a reagent containing an asymmetric center of known absolute stereochemistry, or by vibrational circular dichroism (VCD) spectroscopy.

The subject compounds may be prepared by modification of the procedures disclosed in the Examples as appropriate. Starting materials are commercially available or made by known procedures or as illustrated.

Reactions sensitive to moisture or air were performed under nitrogen or argon using anhydrous solvents and reagents. The progress of reactions was determined by either analytical thin layer chromatography (TLC) usually performed with E. Merck pre-coated TLC plates, silica gel 60F-254, layer thickness 0.25 mm or liquid chromatography-mass spectrometry (LC-MS).

Typically the analytical LC-MS system used consisted of a WATERS ZQ platform with electrospray ionization in positive ion detection mode with an Agilent 1100 series HPLC with autosampler. The column was usually a WATERS XTERRA MS C18, 3.0×50 mm, 5 μm. The flow rate was 1 mL/min, and the injection volume was 10 μL. UV detection was in the range 210-400 nm. The mobile phase consisted of solvent A (water plus 0.05% TFA) and solvent B (acetonitrile plus 0.05% TFA) with a gradient of 100% solvent A for 0.7 min changing to 100% solvent B over 3.75 min, maintained for 1.1 min, then reverting to 100% solvent A over 0.2 min.

Preparative HPLC purifications were usually performed using a mass spectrometry directed system. Usually they were performed on a WATERS Chromatography Workstation configured with an LC-MS System consisting of: WATERS ZQ single quad MS system with Electrospray Ionization, WATERS 2525 Gradient Pump, WATERS 2767 Injector/Collector, WATERS 996 PDA Detector, the MS Conditions of: 150-750 amu, Positive Electrospray, Collection Triggered by MS, and a WATERS SUNFIRE C-18 5 micron, 30 mm (id)×100 mm column. The mobile phases consisted of mixtures of acetonitrile (10-100%) in water containing 0.1% TFA. Flow rates were maintained at 50 mL/min, the injection volume was 1800 μL, and the UV detection range was 210-400 nm. Mobile phase gradients were optimized for the individual compounds.

Reactions performed using microwave irradiation were normally carried out using an Emrys Optimizer manufactured by Personal Chemistry, or an Initiator manufactured by BIOTAGE.

Concentration of solutions was carried out on a rotary evaporator under reduced pressure. Flash chromatography was usually performed using a BIOTAGE Flash Chromatography apparatus (Dyax Corp.) on silica gel (32-63 mM, 60 Å pore size) in pre-packed cartridges of the size noted. $^1$H NMR spectra were acquired at 500 MHz spectrometers in CDCl$_3$ solutions unless otherwise noted. Chemical shifts were reported in parts per million (ppm). Tetramethylsilane (TMS) was used as the internal reference in CDCl$_3$ solutions, and residual CH$_3$OH peak or TMS was used as the internal reference in CD$_3$OD solutions. Coupling constants (J) were reported in hertz (Hz).

Chiral analytical chromatography was usually performed on one of CHIRALPAK AS, CHIRALPAK AD, CHIRALCEL OD, CHIRALCEL IA, or CHIRALCEL OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was sometimes conducted on one of CHIRALPAK AS, CHIRALPAK AD, CHIRALCEL OD, CHIRALCEL IA, or CHIRALCEL OJ columns (20×250 mm) (Daicel Chemical Industries, Ltd.) with desired isocratic solvent systems identified on chiral analytical chromatography or by supercritical fluid (SFC) conditions. Alternatively, chiral preparative chromatography was conducted by supercritical fluid (SFC) conditions using one of CHIRALPAK AS, CHIRALPAK AD-H, CHIRALCEL OD-H, CHIRALPAK IC, or CHIRALCEL OJ-H columns (250×21.2 mm) (Daicel Chemical Industries, Ltd.). Where retention times are provided in the Examples and Tables, they are not intended to be a definitive characteristic of a particular compound since, as known to those skilled in the art, retention times will vary and the timing and/or order of peak elution may change depending on the chromatographic conditions, such as the column used, the condition of the column, and the solvent system and instruments used.

Flash chromatography was carried out on silica gel (230-400 mesh). NMR spectra were obtained in CDCl$_3$ solution unless otherwise noted. Coupling constants (J) are in hertz (Hz).

Abbreviations used herein include: —C(O)CH$_3$ (Ac); acetic acid (AcOH; HOAc); —OC(O)CH$_3$ (OAc); aqueous (aq); benzyl (bn); benzyloxycarbonyl (Cbz); benzyol peroxide (BPO); 3-chloroperoxybenzoic acid (mCPBA); Dess-Martin Periodinane (DMP; 1,1,1-Triacetoxy-1,1-dihydro-1,2,benziodoxol-3(1H)-one; deuterated chloroform (CDCl$_3$); concentrated HCL (Conc. HCl); dibenzylideneacetone (dba); diethyl amine (DEA); di-t-butyl dicarbonate ((BOC)$_2$O, Boc$_2$O); 1,8-Diazabicyclo[5.4.0]undec-7-ene (DBU); Dicyclohexylphosphino-2',4',6'-triisopropylbiphenyl (X-Phos); N,N-diisopropylethylamine (DIPEA, DIEA or Hunig's base); N;N-dimethylformamide (DMF); dimethylsulfide (DMS); dioxane is 1,4-dioxane; 1,2-dichloroethane (DCE); 1-chloroethylchloroformate (ACE-Cl); 1,1'-bis(diphenylphosphino)ferrocene (dppf, DPPF); ethyl acetate (EtOAc or EA); diethyl ether (ether or Et$_2$O); petroleum ether (PE or petrol ether); gram(s) (g); hexane (Hex); hour(s) (h or hr); hexamethylphosphoramide (HMPA); high pressure liquid chromatography (HPLC); 2-propanol (IPA); lithium diisopropylamide (LDA); mass spectrum (ms or MS); methanol-d4 (CD$_3$OD); microliter(s) (IL); milligram(s) (mg); milliliter(s) (mL); millimole (mmol); minute(s) (min); methyl t-butylether (MTBE); medium pressure liquid chromatography (MPLC); N-methylmorpholine-N-oxide (NMO); Pd(dppf)Cl$_2$ or PdCl$_2$(dppf) is 1,1'-Bis(diphenylphosphino)ferrocene]dichloropalladium(II) which may be complexed with CH$_2$Cl$_2$; phenyl (Ph); potassium bis(trimethylsilyl)amide (KHMDS); p-toluenesulfonic acid (TsOH or PTSA); tetrakis(triphenylphosphine)palladium (Pd(PPh$_3$)$_4$);
tris(dibenzylidineacetone)dipalladium (Pd$_2$(dba)$_3$); retention time (R$_t$); room temperature (rt or RT); saturated (sat. or sat'd); saturated aqueous sodium chloride solution (brine); sodium triacetoxyborohydride (NaBH(OAc)$_3$); trifluoromethanesulfonic anhydride (triflic anhydride, (Tf)$_2$O); triethylamine (TEA); trifluoroacetic acid (TFA); tetrahydrofuran (THF); flash chromatography (FC); liquid chromatography (LC); liquid chromatography-mass spectrometry (LCMS, LC/MS or LC-MS); supercritical fluid chromatography (SFC); t-butyloxycarbonyl (Boc or BOC); Diethylaminosulfur trifluoride (DAST); Diethylaminodifluorosulfinium tetrafluoroborate (XtalFluor-E); dichloromethane (DCM); dimethylacetamide (DMA; DMAC); dimethylsulfoxide (DMSO); 1,3-Bis(diphenylphosphino)propane (DPPP); 4,5-Bis(diphenylphosphino)-9,9-dimethylxanthene (Xantphos); acetic acid (HOAc); methyl (Me); methanol (MeOH); N-bromosuccinimide (NBS); N-chlorosuccinimide (NCS); N-iodosuccinimide (NIS); thin layer chromatography (TLC). CELITE® is a trademark name for diatomaceous earth, and SOLKA FLOC® is a trademark name for powdered cellulose. X or x may be used to express the number of times an action was repeated (e.g., washed with 2×200 mL 1N HCl), or to convey a dimension (e.g., the dimension of a column is 30×250 mm).

The following are representative procedures for the preparation of intermediates used to prepare the final products described in the Examples that follow thereafter. These examples are provided for the purpose of further illustration only and are not intended to be limitations on the disclosed invention.

It is understood that a chiral center in a compound may exist in the "S" or "R" stereo-configurations, or as a mixture of both. In many of the examples for intermediate compounds and final compounds, such compounds having a racemic chiral center were separated into individual stereoisomers, for example, referred to as isomer A (or enantiomer A or the like), which refers to the observed faster eluting isomer, and isomer B (or enantiomer B or the like), which refers to the observed slower eluting isomer, and each such isomer may be noted in the example as either the fast or slow eluting isomer. When a single "A" or "B" isomer intermediate is used to prepare a downstream compound, the downstream compound may take the "A" or "B" designation that corresponds to the previously used intermediate. Any Intermediates described below may be referred to herein by their number preceded by "I-" or "Int-." For illustration, in the example titled "Intermediate 3," the racemic parent title compound would be referred to as Intermediate 3 (or I-3), and the separated stereoisomers are noted as Intermediates 3A and 3B (or I-3A and I-3B). In some examples, compounds having a chiral center were derived synthetically from a single isomer intermediate; e.g., Example 4A was made using stereoisomer I-3A. Except for a defined chiral center in a parent isomer mixture, absolute stereochemistry (R or S) of each of the separated isomers was not determined, unless specifically described otherwise. An asterisk (*) may be used in a chemical structure drawing that indicates the location of a chiral center.

Intermediate 1

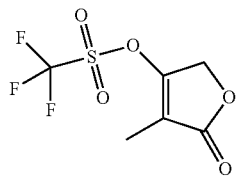

4-Methyl-5-oxo-2,5-dihydrofuran-3-yl trifluoromethanesulfonate

Step A: Ethyl 4-bromo-2-methyl-3-oxobutanoate

To a solution of ethyl 2-methyl-3-oxobutanoate (5.05 g, 35.0 mmol) in water (10 mL) at 0° C. was added bromine (1.805 mL, 35.0 mmol) dropwise over 2 h. The resulting mixture was stirred at room temperature for 16 h, and extracted with ethyl acetate. The organic layer was separated, dried over sodium sulfate, and concentrated in vacuum to give the title compound. ¹H NMR (500 MHz, CDCl₃), δ 4.32-4.27 (m, 2 H), 2.455 (s, 2 H), 1.99 (s, 3 H), 1.337-1.31 (t, 3 H).

Step B: 4-Hydroxy-3-methylfuran-2(5H)-one

A mixture of ethyl 4-bromo-2-methyl-3-oxobutanoate (7.81 g, 35 mmol) and hydrogen bromide (0.040 mL, 48%, 0.35 mmol) was heated at 100° C. for 6 h. The precipitate was collected by filtration, and washed with ethyl acetate to give the title compound. ¹H NMR (500 MHz, CDCl₃), δ 4.60 (s, 2 H), 3.31 (s, 1H), 1.69 (s, 3 H).

Step C: 4-Methyl-5-oxo-2,5-dihydrofuran-3-yl trifluoromethanesulfonate

To a solution of 4-hydroxy-3-methylfuran-2(5H)-one (400 mg, 3.51 mmol) in dichloromethane (10 mL) at −78° C. were added 2,6-lutidine (0.612 mL, 5.26 mmol) and trifluoromethanesulfonic anhydride (0.711 mL, 4.21 mmol) dropwise. The reaction mixture was stirred at −78° C. for 0.5 h, and at rt for 1 h. The mixture was diluted with dichloromethane, washed with 1 N hydrogen chloride three times and saturated sodium bicarbonate solution, dried over sodium sulfate, and concentrated under reduced pressure to give the title compound. LCMS [M+1]⁺=247.0.

Intermediate 2

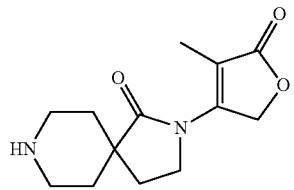 [SMILES: CC1=C(N2CCC3(CCNCC3)C2=O)COC1=O]

2-(4-Methyl-5-oxo-2,5-dihydrofuran-3-yl)-2,8-diazaspiro[4.5]decan-1-one

Step A: Methyl piperidine-4-carboxylate

To a solution of piperidine-4-carboxylic acid (1000 g, 7.75 mol) in MeOH (8000 mL) was added SOCl₂ (1000 mL) at 0° C. The mixture was stirred at rt for 18 h and concentrated to give the title compound. ¹H-NMR (400 MHz, CD₃OD) δ 3.74 (s, 3 H), 3.43-3.35 (m, 2 H), 3.12-3.06 (m, 2H), 2.81-2.74 (m, 1 H), 2.20-2.15 (m, 2H), 1.95-1.85 (m, 2H).

Step B: 1-tert-Butyl 4-methyl piperidine-1,4-dicarboxylate

To a solution of methyl piperidine-4-carboxylate (1400 g, 7.75 mol) in DCM (8000 mL) were added NaHCO₃ (1953 g, 23.21 mol) and Boc₂O (2030 g, 9.3 mol) dropwise at 0° C. The mixture was stirred at rt for 18 h, and was filtered. The filtrate was concentrated in vacuum to give the title compound. ¹H-NMR (400 MHz, CDCl₃) δ 4.100-3.90 (m, 2 H), 3.68 (s, 3 H), 2.85-2.79 (m, 2 H), 2.47-2.41 (m, 1 H), 1.88-1.80 (m, 2 H), 1.66-1.52 (m, 2H), 1.47 (s, 9 H).

Step C: 1-tert-Butyl 4-methyl 4-(cyanomethyl)piperidine-1,4-dicarboxylate

To a solution of 1-tert-butyl 4-methyl piperidine-1,4-dicarboxylate (185 g, 761.3 mmol) in THF (1200 mL) was added dropwise of LDA [prepared from n-BuLi (2.5 M, 420 mL) and diisopropylamine (128 g, 1.07 mol) in THF (300 mL)] at −70° C. under N₂. The mixture was stirred at −70° C. for 1.5 h, and to this mixture was added a solution of bromoacetonitrile (128 g, 1.12 mol) in THF (300 mL) at −70° C. Stirring continued at −70° C. for 1 h and at 20° C. for 18 h. The resulting mixture was quenched with H₂O. The organic layer was separated, and the aqueous was extracted with EtOAc three times. The combined organic extracts were dried over Na₂SO₄ and concentrated. The residue was purified by silica gel chromatography eluted with PE/EA (5:1) to give the title compound. ¹H-NMR (400 MHz, CDCl$_3$) δ 3.90-3.75 (m, 5 H), 3.12-3.00 (m, 2 H), 2.61-2.56 (m, 2 H), 2.19-2.1 (m, 2 H), 1.59-1.50 (m, 2 H), 1.40 (s, 9 H).

Step D: tert-Butyl 1-oxo-2,8-diazaspiro[4.5]decane-8-carboxylate

To a solution of 1-tert-butyl 4-methyl 4-(cyanomethyl)piperidine-1,4-dicarboxylate (350 g, 1.2 mol) in MeOH (6000 mL) were added NH$_3$.H$_2$O (400 mL) and Raney-Ni (300 g) at rt. The mixture was stirred under 2 MPa of hydrogen at 50° C. for 18 h, and filtered. The filtrate was concentrated. The crude product was washed with EtOAc to give the title compound. $^1$H-NMR (400 MHz, CDCl$_3$) δ 6.30 (s, 1 H), 4.08-3.92 (m, 2 H), 3.38-3.30 (m, 2 H), 3.01-2.91 (m, 2 H), 2.10-2.00 (m, 2 H), 1.88-1.78 (m, 2 H), 1.49-1.32 (m, 11 H).

Step E: tert-Butyl 2-(4-methyl-5-oxo-2,5-dihydrofuran-3-yl)-1-oxo-2,8-diazaspiro[4.5]decane-8-carboxylate:

To a mixture of tert-butyl 1-oxo-2,8-diazaspiro[4.5]decane-8-carboxylate (80.0 g, 315 mmol) and 4-methyl-5-oxo-2,5-dihydrofuran-3-yltrifluoromethanesulfonate (Int. 1; 85.2 g, 346 mmol), Xantphos (13.6 g, 23.6 mmol), and Cs$_2$CO$_3$ (153.7 g, 471.8 mmol) in toluene (1200 mL), was added Pd$_2$(dba)$_3$ (7.20 g, 7.86 mmol) under N$_2$. The reaction mixture was heated at 90° C. under N$_2$ for 18 h, filtered through a pad of CELITE. The filtrate was concentrated. The residue was purified via crystallization to give the title compound. $^1$H NMR (400 MHz, CDCl$_3$) δ 5.23 (s, 2 H), 4.02-3.99 (m, 4 H), 3.06-3.05 (m, 2 H), 2.15-2.11 (m, 2 H), 2.02 (s, 3 H), 1.87-1.81 (m, 2 H), 1.51-1.41 (m, 11 H).

Step F: 2-(4-Methyl-5-oxo-2,5-dihydrofuran-3-yl)-2,8-diazaspiro[4.5]decan-1-one:

To a mixture of of tert-butyl 2-(4-methyl-5-oxo-2,5-dihydrofuran-3-yl)-1-oxo-2,8-diazaspiro[4.5]decane-8-carboxylate (57.0 g, 163 mmol) in EtOAc (180 mL) was added saturated HCl (g)/EtOAc (712 mL) at 0° C. The reaction mixture was stirred at room temperature for 3 h, and filtered. The filtrate was concentrated to give the HCl salt. To a mixture of HCl salt (54.2 g, 189 mmol) in MeOH (550 mL) was added NaHCO$_3$ (31.8 g, 378 mmol) at 0° C. The mixture was stirred at rt for 3 h until the pH=8. The mixture was filtered, and the filtrate was concentrated. The residue was re-dissolved in MeOH, and concentrated until a precipitate appeared. The precipitate was filtered off. The filtrate was concentrated to give the title compound as a free amine. 1H NMR (400 MHz, CD$_3$OD) δ 5.24 (s, 2 H), 4.10-4.07 (m, 2 H), 3.22-3.16 (m, 2 H), 2.93-2.87 (m, 2 H), 2.22-2.19 (m, 2 H), 2.0 (s, 3 H), 1.94-1.87 (m, 2 H), 1.67-1.61 (m, 2 H).

Intermediate 3A

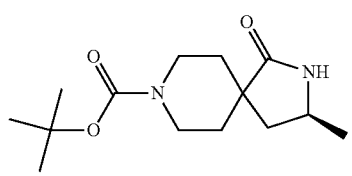 [SMILES: C[C@H]1CC2(CCN(C(=O)OC(C)(C)C)CC2)C(=O)N1]

(S)-tert-Butyl 3-methyl-1-oxo-2,8-diazaspiro[4.5]decane-8-carboxylate

Intermediate 3B

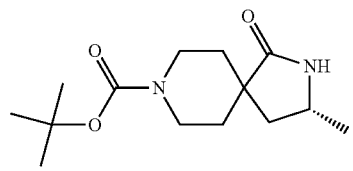 [SMILES: C[C@@H]1CC2(CCN(C(=O)OC(C)(C)C)CC2)C(=O)N1]

(R)-tert-Butyl 3-methyl-1-oxo-2,8-diazaspiro[4.5]decane-8-carboxylate

Step A: 1-tert-Butyl 4-methyl 4-(2-methylallyl)piperidine-1,4-dicarboxylate

A solution of N-boc-piperidine-4-carboxylic acid methyl ester (2 g, 8.22 mmol) in THF (40 ml) was cooled to −78° C. Under nitrogen, to this solution was added LDA (6.17 ml, 12.33 mmol, 2.0 M in THF) dropwise. The reaction mixture was stirred at −78° C. for 30 minutes, and a solution of 3-bromo-2-methylpropene (1.6 g, 11.85 mmol) in THF (2 ml) was added. After the mixture was stirred for 1 h at the same temperature, the reaction was quenched with saturated ammonium chloride aqueous (5 ml). The mixture was allowed to warm up to rt, extracted with EtOAc twice. The combined organic layers were washed with brine, dried over anhydrous sodium sulfate and filtered. The filtrate was concentrated and the crude product was purified by silica gel column chromatography eluting with 0-30% ethyl acetate/hexane to give the title compound. LCMS [M−56+1]$^+$=242.2.

Step B: 1-tert-Butyl 4-methyl 4-(2-oxopropyl)piperidine-1,4-dicarboxylate

To a solution of 1-tert-butyl 4-methyl 4-(2-methylallyl)piperidine-1,4-dicarboxylate (2.2 g, 7.40 mmol) in dioxane/water(60 ml, 1/1) under nitrogen was added osmium tetraoxide (0.038 g, 0.148 mmol) and sodium periodate (2.88 g, 13.46 mmol). The mixture was stirred at rt for 3 h. The mixture was then diluted with dichloromethane, and washed with 20% Na$_2$S$_2$O$_3$ (20 ml). The organic layers were combined and washed with brine, dried over anhydrous sodium sulfate, and filtered. The filtrates were concentrated and the residue was purified by silica gel column chromatography eluting with 0-60% ethyl acetate in hexane to afford the title compound. LCMS [M+23]$^+$=322.2.

Step C: tert-Butyl 3-methyl-1-oxo-2,8-diazaspiro[4.5]decane-8-carboxylate (racemic)

To a solution of 1-tert-Butyl 4-methyl 4-(2-oxopropyl)piperidine-1,4-dicarboxylate (1.15 g, 3.84 mmol) in methanol (25 ml) were added ammonium acetate (3.85 g, 49.9 mmol), sodium cyanoborohydride (0.681 g, 10.83 mmol) and magnesium sulfate (2.54 g, 21.13 mmol). The mixture was heated at 80° C. in a sealed tube for 12 hours, cooled to rt, and filtered through a pad of CELITE. The filter cake was washed with methanol. The combined filtrates were then concentrated, and the residue was purified by silica gel column chromatography eluting with 0-10% methanol in ethyl acetate to afford the title compound. LCMS [M+23]$^+$=291.2.

Step D: (S)-tert-Butyl 3-methyl-1-oxo-2,8-diazaspiro[4.5] decane-8-carboxylate, and (R)-tert-Butyl 3-methyl-1-oxo-2,8-diazaspiro[4.5]decane-8-carboxylate.

tert-Butyl 3-methyl-1-oxo-2,8-diazaspiro[4.5]decane-8-carboxylate (racemic) was subjected to SFC chiral separation. The two enantiomers were resolved on CHIRALCEL IA column eluting with 30% MeOH:MeCN (2:1)/CO₂ (100 bar, 35° C.). The fast eluting component was (S)-tert-Butyl 3-methyl-1-oxo-2,8-diazaspiro[4.5]decane-8-carboxylate, and the slow eluting component was (R)-tert-Butyl 3-methyl-1-oxo-2,8-diazaspiro[4.5]decane-8-carboxylate.

Intermediate 4A

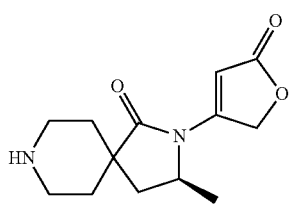 [SMILES: C[C@H]1CC2(CCNCC2)C(=O)N1C1=CC(=O)OC1]

(S)-3-methyl-2-(5-oxo-2,5-dihydrofuran-3-yl)-2,8-diazaspiro[4.5]decan-1-one

Step A: (S)-tert-butyl 3-methyl-1-oxo-2-(5-oxo-2,5-dihydrofuran-3-yl)-2,8-diazaspiro[4.5]decane-8-carboxylate To a sealed tube was added (S)-tert-butyl 3-methyl-1-oxo-2,8-diazaspiro[4.5]decane-8-carboxylate (Int. 3A; 4.20 g, 15.65 mmol), 4-bromofuran-2-one (3.83 g, 23.48 mmol), 4,5-bis(diphenylphosphino)-9,9-dimethylxanthene (3.62 g, 6.26 mmol), K₂CO₃ (4.33 g, 31.3 mmol), water (846 µl, 47.0 mmol) and palladium (II) acetate (0.376 g, 1.675 mmol) and toluene (80 ml). The resulting mixture was bubbled with N₂ gas for 20 min. The tube was sealed and the mixture was heated at 90° C. for 48 hrs. After cooling to rt, the mixture was diluted with EtOAc and filtered. The filtrates were concentrated and the residue was purified by silica gel column chromatography using 0-100% EtOAc/hexane as the gradient to give the title compound. LCMS[M+1]⁺=351.4.

Step B: (S)-3-methyl-2-(5-oxo-2,5-dihydrofuran-3-yl)-2,8-diazaspiro[4.5]decan-1-one To the solution of (S)-tert-butyl 3-methyl-1-oxo-2-(5-oxo-2,5-dihydrofuran-3-yl)-2,8-diazaspiro[4.5]decane-8-carboxylate (1.78 g, 5.08 mmol) in DCM (20 mL) was added trifluoroacetic acid (10 ml). The resulting solution was stirred at rt for 1 hr. The solution was concentrated and the residue was basified on ion-exchange column (SCX) by washing with methanol and eluting with 1 N ammonia/methanol to give the title compound. LCMS [M+1]⁺=251.23.

Intermediate 4B

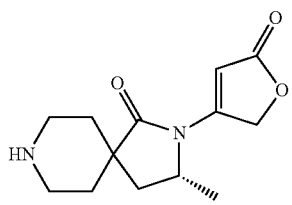 [SMILES: C[C@@H]1CC2(CCNCC2)C(=O)N1C1=CC(=O)OC1]

(R)-3-methyl-2-(5-oxo-2,5-dihydrofuran-3-yl)-2,8-diazaspiro[4.5] decan-1-one (R)-3-methyl-2-(5-oxo-2,5-dihydrofuran-3-yl)-2,8-diazaspiro[4.5]decan-1-one was prepared using a similar procedure as (S)-3-methyl-2-(5-oxo-2,5-dihydrofuran-3-yl)-2,8-diazaspiro[4.5]decan-1-one (intermediate 4A), but starting in step (A) with (R)-tert-butyl 3-methyl-1-oxo-2,8-diazaspiro[4.5]decane-8-carboxylate (Int. 3B).

Intermediate 5

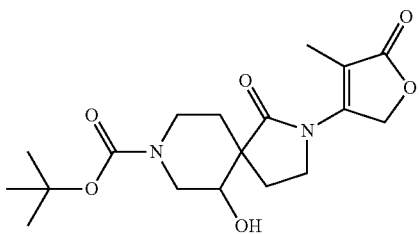 [SMILES: CC1=C(N2CCC3(CCN(C(=O)OC(C)(C)C)CC3O)C2=O)COC1=O]

tert-butyl 6-hydroxy-2-(4-methyl-5-oxo-2,5-dihydrofuran-3-yl)-1-oxo-2,8-diazaspiro[4.5]decane-8-carboxylate (cis)

Step A: Ethyl 1-benzyl-4-(cyanomethyl)-3-oxopiperidine-4-carboxylate

To a flask charged with ethyl 1-benzyl-3-oxopiperidine-4-carboxylate (1.0 g, 3.8 mmol) and a stir bar was added K₂CO₃ (1.06 g, 7.6 mmol), bromoacetonitrile (0.92 g, 7.6 mmol), and acetone (15 mL). The reaction was allowed to stir at rt for 2 h, then heated to 45° C. for 3 h. The reaction was quenched with saturated NH₄Cl solution, extracted with EtOAc, dried over Na₂SO₄, filtered and concentrated. The crude product was purified by MPLC using 10-100% acetonitrile (0.1% TFA)/water (0.1% TFA) as the gradient to furnish the title compound. LCMS [M+1]⁺=301.

Step B: 8-Benzyl-6-hydroxy-2,8-diazaspiro[4.5]decan-1-one

To a flask charged with ethyl 1-benzyl-4-(cyanomethyl)-3-oxopiperidine-4-carboxylate (900 mg, 3.0 mmol) were added platinum oxide (100 mg, 0.44 mmol), MeOH (20 mL) and acetic acid (20 mL). The mixture was allowed to stir vigorously under an atmosphere of hydrogen for 24 h. The catalyst was removed by filtration through a pad of CELITE, and the filtrate was concentrated under reduced pressure. The residue was dissolved in EtOH (100 mL), and K₂CO₃ (2.1 g, 15 mmol) was added. The mixture was heated at 90° C. for 4 h, cooled to rt, and DCM (200 mL) was added to precipitate the solids. The solids were then removed by filtration, the filtrate was concentrated, and the residue was purified on a silica gel column using 0-10% MeOH/DCM (mixed with 10% NH₄OH) as eluting solvents to give the title compound. LCMS [M+1]⁺=261.

Step C: 8-Benzyl-6-hydroxy-2-(4-methyl-5-oxo-2,5-dihydrofuran-3-yl)-2,8-diazaspiro[4.5]decan-1-one (trans and cis)

To a flask charged with 8-benzyl-6-hydroxy-2,8-diazaspiro[4.5]decan-1-one (520 mg, 2.0 mmol) were added palladium acetate (22 mg, 0.10 mmol), K₂CO₃ (550 mg, 4.00 mmol), Xantphos (120 mg, 0.20 mmol), 4-Methyl-5-oxo-2,5-dihydrofuran-3-yltrifluoromethanesulfonate (Int. 1; 640 mg, 2.6 mmol), and water (110 mg, 6.0 mmol). The mixture was heated to 60° C. for 16 h. The reaction mixture was diluted with EtOAc, washed with water, dried over Na₂SO₄, filtered and concentrated. The resultant oil was loaded onto a silica gel column, and eluted with EtOAc/hexane. Two peaks were separated. The fast eluting peak was the minor product (Bn-trans, racemic), and the slow moving spot was the major product (Bn-cis, racemic). LCMS [M+1]⁺=357.

Step D: tert-Butyl 6-hydroxy-2-(4-methyl-5-oxo-2,5-dihydrofuran-3-yl)-1-oxo-2,8-diazaspiro[4.5]decane-8-carboxylate (cis).

To a solution of 8-benzyl-6-hydroxy-2-(4-methyl-5-oxo-2,5-dihydrofuran-3-yl)-2,8-diazaspiro[4.5]decan-1-one (cis) (10 g, 28.2 mmol) and di-tert-butylcarbonate (7.21 ml, 31.0 mmol) in methanol (50 ml) was added palladium on carbon (1.501 g, 1.411 mmol). The resulting mixture was subjected to hydrogenation at 45 Psi at rt over the weekend, and filtered through CELITE under nitrogen. The filtrate was concentrated and the residue was purified on silica gel using ethyl acetate/hexane as eluting solvents to give the title compound. LCMS [M+1]⁺=367.1.

Intermediate 6A

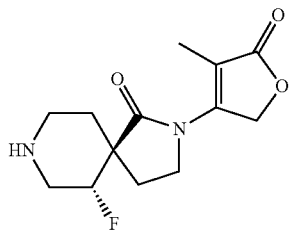 [SMILES: CC1=C(N2CC[C@]3(CCNC[C@H]3F)C2=O)COC1=O]

(5R,6S)-6-fluoro-2-(4-methyl-5-oxo-2,5-dihydrofuran-3-yl)-2,8-diazaspiro[4.5]decan-1-onetrans, enantiomer A)

Step A: (5S,6S)-tert-butyl 6-fluoro-2-(4-methyl-5-oxo-2,5-dihydrofuran-3-yl)-1-oxo-2,8-diazaspiro[4.5]decane-8-carboxylate (trans, fast enantiomer A) and (5R,6R)-tert-butyl 6-fluoro-2-(4-methyl-5-oxo-2,5-dihydrofuran-3-yl)-1-oxo-2,8-diazaspiro[4.5]decane-8-carboxylate (trans, slow, enantiomer B).

To the solution of tert-butyl 6-hydroxy-2-(4-methyl-5-oxo-2,5-dihydrofuran-3-yl)-1-oxo-2,8-diazaspiro[4.5]decane-8-carboxylate (intermediate 5, cis, racemic) (1.84 g, 5.02 mmol) in methylene chloride (100 ml) was added DAST (0.863 ml, 6.53 mmol) dropwise under nitrogen at 0° C. The resulting solution was stirred at 0° C. for 2.5 h, and quenched with addition of 200 mL saturated sodium bicarbonate. The organic layer was separated, and the aqueous layer was extracted with methylene chloride two times. The combined organic layers were dried over sodium sulfate, concentrated and the residue was purified on silica gel column using ethyl acetate/hexane as eluting solvents to give tert-butyl 6-fluoro-2-(4-methyl-5-oxo-2,5-dihydrofuran-3-yl)-1-oxo-2,8-diazaspiro[4.5]decane-8-carboxylate (trans, racemic). LCMS [M+1]⁺=369.19. The racemate was separated on chiral AD-H column using methanol (0.05% DEA) in CO₂ to give (5S,6S)-tert-butyl 6-fluoro-2-(4-methyl-5-oxo-2,5-dihydrofuran-3-yl)-1-oxo-2,8-diazaspiro[4.5]decane-8-carboxylate (trans, fast enantiomer A), and (5R,6R)-tert-butyl 6-fluoro-2-(4-methyl-5-oxo-2,5-dihydrofuran-3-yl)-1-oxo-2,8-diazaspiro[4.5]decane-8-carboxylate (trans, slow, enantiomer B). LCMS [M+1-56]⁺=313.0.

Step B: (5R,6S)-6-fluoro-2-(4-methyl-5-oxo-2,5-dihydrofuran-3-yl)-2,8-diazaspiro[4.5]decan-1-one (trans, enantiomer A)

To a solution of (5S,6S)-tert-butyl 6-fluoro-2-(4-methyl-5-oxo-2,5-dihydrofuran-3-yl)-1-oxo-2,8-diazaspiro[4.5]decane-8-carboxylate (trans, fast enantiomer A) (0.60 g, 1.629 mmol) in methylene chloride (5 ml) was added trifluoroacetic acid (5 ml, 64.9 mmol). The resulting solution was stirred at rt for 2 h, and concentrated. The residue was basified on BOND ELUT SCX ion exchange column washed with MeOH to remove the acid followed by eluting with 1 N ammonia in methanol to give (5R,6S)-6-fluoro-2-(4-methyl-5-oxo-2,5-dihydrofuran-3-yl)-2,8-diazaspiro[4.5]decan-1-one (trans, enantiomer A). LCMS [M+1]⁺=269.0.

Intermediate 6B

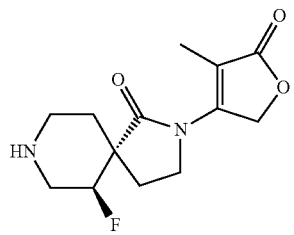

(5S,6R)-6-fluoro-2-(4-methyl-5-oxo-2,5-dihydrofuran-3-yl)-2,8-diazaspiro[4.5]decan-1-one (trans, enantiomer B)

To a solution of (5R,6R)-tert-butyl 6-fluoro-2-(4-methyl-5-oxo-2,5-dihydrofuran-3-yl)-1-oxo-2,8-diazaspiro[4.5]decane-8-carboxylate (Int. 6A, step A, trans, slow, enantiomer B) (0.60 g, 1.629 mmol) in methylene chloride (5 ml) was added trifluoroacetic acid (5 ml, 64.9 mmol). The resulting solution was stirred at rt for 2 h, and concentrated. The residue was basified on BOND ELUT SCX ion exchange column, washed with MeOH to remove the acid, and then eluted with 1 N ammonia in methanol to give (5S,6R)-6-fluoro-2-(4-methyl-5-oxo-2,5-dihydrofuran-3-yl)-2,8-diazaspiro[4.5]decan-1-one (trans, enantiomer B). LCMS [M+1]⁺=269.0.

Intermediate 7

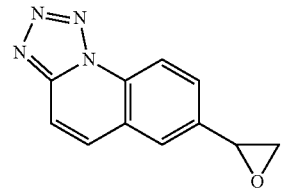 [SMILES: c1cc2c(ccc3nnnn32)cc1C1CO1]

7-(oxiran-2-yl)tetrazolo[1,5-α]quinoline

Step A: 7-bromotetrazolo[1,5-α]quinoline
A solution of 6-bromo-2-chloroquinoline (4.00 g, 16.6 mmol) and sodium azide (2.16 g, 3.32 mmol) in 20 mL DMF was stirred at 130° C. for 18 h. Then the solution was poured into cold water (200 mL) and stirred for 30 min, filtered and washed with cold water, and dried to afford the title compound. LC/MS[M+1]$^+$=248.9.

Step B: 7-vinyltetrazolo[1,5-α]quinoline

To a mixture of 7-bromotetrazolo[1,5-α]quinoline (3.35 g, 13.4 mmol), potassium vinyltrifluoroborate (3.62 g, 8.0 mmol), and Pd(dppf)Cl$_2$ (335 mg, 0.44 mmol) in EtOH (100 mL) was added Et$_3$N (1.31 g, 13.2 mmol), and the mixture was heated at 80° C. for 2 hours. The mixture was cooled, filtered, the cake rinsed with EtOH, and then concentrated, The residue was then purified on a silica gel column eluted with petroleum ether/EtOAc from 5/1 to 1/1 as the eluting solvents to afford the title compound. LC/MS [M+1]$^+$=197.1.

Step C: 7-(oxiran-2-yl)tetrazolo[1,5-α]quinoline

A mixture of 7-vinyltetrazolo[1,5-α]quinoline (1.64 g, 8.32 mmol) and NBS (1.62 g, 9.15 mmol) in a solution of t-butanol (27.3 mL) and water (54.6 mL) was heated to 40° C., stirred until the solid was mostly dissolved, and then stirred for another 2 hours. A solution of NaOH (998 mg, 25.0 mmol) in water (11 mL) was added slowly. The mixture was cooled to 0° C., then stirred for 1 hour, concentrated, and then purified on a silica gel column with petroleum ether/EtOAc=1/1 as the eluting solvents to afford the title compound. LC/MS[M+1]$^+$=213.1.

Intermediate 8

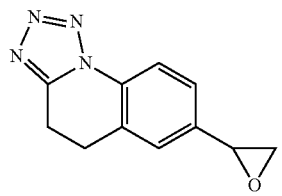 [SMILES: c1cc2c(cc1C1CO1)CCc1nnnn1-2]

7-(oxiran-2-yl)-4,5-dihydrotetrazolo[1,5-α]quinoline

Step A: 6-bromo-3,4-dihydroquinolin-2(1H)-one

To a solution of 3,4-dihydro-1H-quinolin-2-one (5.00 g, 31.0 mmol) in 40 mL of CH$_3$CN was added NBS (6.80 g, 38.0 mmol) in portions at 0° C. The mixture was stirred at 0° C. for 2 h, then 30 mL of water was added and the solution was extracted with ethyl acetate three times. The combined organic phase was dried over Na$_2$SO$_4$, filtered and then concentrated to afford the title compound. LC/MS[M+1]$^+$=226.

Step B: 7-bromo-4,5-dihydrotetrazolo[1,5-α]quinoline

A solution of 6-bromo-3,4-dihydroquinolin-2(1H)-one (1.00 g, 4.4 mmol) and diphenyl-2-pyridylphosphine (4.60 g, 17.6 mmol) in THF (15 mL) was added diisopropyl azadicarboxylate (3.60 g, 17.6 mmol), followed by addition of DPPA (4.80 g, 17.6 mmol). The mixture was stirred at 45° C. for 24 h, diluted with ethyl acetate and washed with saturated aqueous sodium bicarbonate solution. The organic layer was dried over anhydrous Na$_2$SO$_4$ and concentrated. The residue was purified by flash chromatography on a silica gel column using petroleum ether/EtOAc from 10:1 to 3:1 as eluting solvents to afford the title compound as a yellow solid. LC/MS [M+1]$^+$=251.

Step C: 7-vinyl-4,5-dihydrotetrazolo[1,5-α]quinoline

To a mixture of 7-bromo-4,5-dihydrotetrazolo[1,5-α]quinoline (500 mg, 2.0 mmol), potassium vinyltrifluoroborate (536 mg, 4.0 mmol), and Pd(dppf)Cl$_2$ (50 mg, 10%) in EtOH (10 mL) was added Et$_3$N (404 mg, 4.0 mmol), and the resulting mixture was heated at 80° C. for 2 hours. The mixture was cooled and filtered, the cake rinsed with EtOH (20 mL), and concentrated. The resultant product was then purified by flash chromatography on a silica gel column using petroleum ether/EtOAc from 10:1 to 3:1 as the eluting solvents to afford the title compound. LC/MS[M+1]$^+$=199.

Step D: 7-(oxiran-2-yl)-4,5-dihydrotetrazolo[1,5-α]quinoline

A mixture of 7-vinyl-4,5-dihydrotetrazolo[1,5-α]quinoline (300 mg, 1.51 mmol) and NBS (298 mg, 1.68 mmol) in a solution of t-butanol (5 mL) and water (10 mL) was heated to 40° C. The mixture was stirred until the solid was mostly dissolved, and then stirred for another 2 hours. A solution of NaOH (184 mg, 4.59 mmol) in water (2 mL) was added slowly. The mixture was then cooled to 0° C., stirred for 1 hour, and concentrated. The resultant product was purified by flash chromatography on a silica gel column using petroleum ether/EtOAc from 10:1 to 1:1 as the eluting solvents to afford the title compound. LC/MS [M+1]$^+$=215.

Intermediate 9

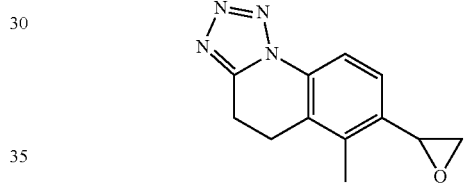

6-methyl-7-(oxiran-2-yl)-4,5-dihydrotetrazolo[1,5-α]quinoline

Step A: 3-chloro-N-(m-tolyl)propanamide

3-Chloropropanoyl chloride (7.05 g, 56.0 mmol) was added dropwise to a solution of m-toluidine (5.00 g, 46.8 mmol), and TEA (7.10 g, 65.2 mmol) in DCM (30 mL). The mixture was stirred at room temperature for 16 hours. 20 mL of water was then added, and the organic layer was separated, washed with brine, dried over MgSO$_4$, filtered and concentrated to afford the title compound. LC/MS [M+1]$^+$=198.

Step B: 5-methyl-3,4-dihydroquinolin-2(1H)-one

To a solution of 3-chloro-N-(m-tolyl)propanamide (6.00 g, 30.5 mmol) in chlorobenzene (60 mL) was added AlCl$_3$ (16.08 g, 122 mmol) in several portions. The temperature was slowly raised to 140° C. and the solution was stirred at this temperature for 6 hours. The mixture was cooled, diluted with 100 mL of toluene, quenched with 200 mL water and then extracted with DCM. The organic layer was concentrated to afford the title compound and 7-methyl-3,4-dihydroquinolin-2(1H)-one (1:1 mixture). LC/MS [M+1]$^+$=162.

Step C: 6-bromo-5-methyl-3,4-dihydroquinolin-2(1H)-one

To a solution of 5-methyl-3,4-dihydroquinolin-2(1H)-one and 7-methyl-3,4-dihydroquinolin-2(1H)-one (3.00 g, 18.5 mmol, 1:1 mixture) in CH$_3$CN (30 ml) was added NBS (3.76 g, 2.10 mmol). The mixture was stirred at 25° C. for 16 hours. The mixture was then concentrated and the residue was purified by flash column chromatography on a silica gel column using 35-40% EtOAc/petroleum ether as the eluting solvents to afford the title compound and 7-bromo-8-methyl-4,5-dihydrotetrazolo[1,5-α]quinoline. LC/MS [M+1]$^+$=240; 242.

Step D: 7-bromo-6-methyl-4,5-dihydrotetrazolo[1,5-α]quinoline

To a mixutre of 6-bromo-5-methyl-3,4-dihydroquinolin-2(1H)-one and 7-bromo-8-methyl-4,5-dihydrotetrazolo[1,5-α]quinoline (1.00 g, 4.10 mmol), DPPA (4.54 g, 16.5 mmol), and (2-pyridyl)PPh$_2$ (4.35 g, 1.65 mmol) in THF (15 mL) was added DIAD (3.34 g, 1.65 mmol) dropwise. The mixture was stirred at 50° C. for 18 hours. The mixture was then diluted with EtOAc and washed with aqueous Na$_2$CO$_3$. The organic layer was separated, dried over Na$_2$SO$_4$, filtered and concentrated to afford the title compound as crude product. $^1$H NMR (400 MHz, CDCl$_3$) δ 8.69 (d, J=8.4 Hz, 1H), 7.60 (d, J=8.4 Hz, 1H), 3.29 (t, J=7.2 Hz, 2H), 3.11 (t, J=7.2 Hz, 2H), 2.44 (s, 3H). LC/MS [M+1]$^+$=265; 267.

Step E: 6-methyl-7-vinyl-4,5-dihydrotetrazolo[1,5 -α]quinoline

To a mixture of 7-bromo-6-methyl-4,5-dihydrotetrazolo[1,5-α]quinoline (410 mg, 1.55 mmol), potassium vinyltrifluoroborate (249 mg, 1.86 mmol), and Pd(dppf)Cl$_2$ (115 mg, 0.155 mmol) in EtOH (10 mL) was added Et$_3$N (313 mg, 3.10 mmol). The resulting mixture was heated to 80° C. and stirred for 3 hours. The mixture was filtered, concentrated, and the residue was then purified by flash column chromatography on silica gel using EtOAc/petroleum ether as the eluting solvents to afford the title compound. LC/MS [M+1]$^+$=213.

Step F: 6-methyl-7-(oxiran-2-yl)-4,5-dihydrotetrazolo[1,5-α]quinoline

A mixture of 6-methyl-7-vinyl-4,5-dihydrotetrazolo[1,5 -α] quinoline (120 mg, 0.57 mmol) and NBS (111 mg, 0.62 mmol) in a solution of t-butanol (2 mL) and water (4 mL) was heated to 40° C. and stirred until the solid was mostly dissolved. The mixture was then stirred for another 2 hours. A solution of NaOH (68 mg, 1.7 mmol) in water (5 mL) was then added slowly. The solution was cooled to 0° C., and stirred for 1 hour. The mixture was then concentrated and purified by flash silica gel column chromatography using 50% EtOAc/petroleum ether as the eluting solvents to afford the title compound. LC/MS[M+1]$^+$=229.

Intermediate 10

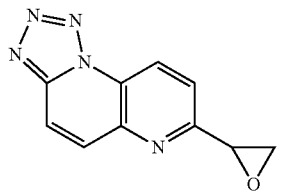 [SMILES: c1cc2c(ccc3nnnn32)nc1C1CO1]

7-(oxiran-2-yl)tetrazolo[1,5-α][1,5]naphthyridine

Step A: 6-chloro-2-iodopyridin-3-amine

To a solution of 6-chloropyridin-3-amine (10.00 g, 77.8 mmol) in EtOH (150 mL) was added Ag$_2$SO$_4$ (12.10 g, 38.9 mmol) and I$_2$(23.70 g, 93.4 mmol) at room temperature. The mixture was stirred at room temperature overnight and then concentrated. Water (100 mL) and EtOAc (200 mL) were added to the residue. The organic layer was separated and the aqueous layer was extracted with EtOAc three times. The combined organic layers were dried over anhydrous Na$_2$SO$_4$, filtered and concentrated. The residue was purified by chromatography on a silica gel column using petroleum ether/EtOAc (7:1) as the eluting solvents to afford the title compound. LC/MS [M+1]$^+$=255.

Step B: (E)-ethyl 3-(3-amino-6-chloropyridin-2-yl)acrylate

A mixture of 6-chloro-2-iodopyridin-3-amine (5.50 g, 21.6 mmol), ethyl acrylate (2.65 g, 26 mmol), Pd(OAc)$_2$ (0.24 g, 1.08 mmol), DIEA (5.60 g, 43.2 mmol) and X-Phos (1.05 g, 2.2 mmol) in dioxane (60 mL) was heated at 80° C. for 3 h under N$_2$ protection. The mixture was then filtered and concentrated. The crude product was purified by flash column chromatography on a silica gel column using ethyl acetate/petroleum ether from 100:1 to 20:1 as the eluting solvents to afford the title compound. LC/MS [M+1]$^+$=227.

Step C: 6-chloro-1,5-naphthyridin-2(1H)-one

To a solution of (E)-ethyl 3-(3-amino-6-chloropyridin-2-yl)acrylate (2.00 g, 8.8 mmol), DBU (2.69 g, 17.6 mmol) in EtOH (20 mL) was added 5 mL of DBU dropwise at room temperature. The resulting mixture was stirred at 100° C. for 18 h under N$_2$. After concentration, the crude product was purified by chromatography on a silica gel column using petroleum ether/EtOAc (15:1) as the eluting solvents to afford the title compound. LC/MS [M+1]$^+$=181.2.

Step D: 6-chloro-1,5-naphthyridin-2-yl trifluoromethanesulfonate

To a mixture of 6-chloro-1,5-naphthyridin-2(1H)-one (1.68 g, 9.3 mmol) and K$_2$CO$_3$ (1.93 g, 14.0 mmol) in DMF (30 mL) was added PhNTf$_2$ (6.64 g, 14.0 mmol) in portions. The resulting mixture was stirred at room temperature for 24 hours under N$_2$. The reaction mixture was diluted with water (20 mL), and then extracted with EtOAc three times. The combined organic layers were dried over anhydrous Na$_2$SO$_4$, filtered and concentrated. The crude product was purified by chromatography on a silica gel column using petroleum ether/EtOAc (5:1) as the eluting solvents to afford the title compound. LC/MS [M+1]$^+$=313.0.

Step E: 2-chloro-6-vinyl-1,5-naphthyridine

To a solution of 6-chloro-1,5-naphthyridin-2-yl trifluoromethanesulfonate (100 mg, 0.32 mmol), potassium vinyltrifluoroborate (21 mg, 0.16 mmol) in EtOH (2 mL) was added Pd(PPh$_3$)$_2$Cl$_2$ (10 mg) and TEA (32 mg, 0.32 mmol) at room temperature. The mixture was heated at 80° C. for 4 h and then cooled. After concentration, the crude product was directly used in the next step. LC/MS [M+1]$^+$=191.

Step F: 7-vinyltetrazolo[1,5-α][1,5]naphthyridine

To a solution of 2-chloro-6-vinyl-1,5-naphthyridine (48 mg, 0.25 mmol) in DMF (5 mL) was added NaN$_3$ (48 mg, 0.75 mmol). The mixture was stirred at 130° C. for 3 h under N$_2$. The mixture was cooled and poured into water, and extracted by EtOAc. The combined organic layers were dried over anhydrous Na$_2$SO$_4$, filtered and concentrated. The crude product was purified by preparative TLC using petroleum ether/EtOAc (3:1) as the developing solvents to afford the title compound. LC/MS[M+1]$^+$=198.1.

Step G: 7-(oxiran-2-yl)tetrazolo[1,5-α][1,5]naphthyridine

To a solution of 7-vinyltetrazolo[1,5-α][1,5]naphthyridine (20 mg, 0.1 mmol) in t-BuOH (1 mL) and water (2 mL) was added NBS (20 mg, 0.11 mmol). The mixture was heated to 40° C. and stirred for 2 h. The mixture was then cooled to 0° C. and NaOH (12 mg, 0.30 mmol) in water (1 mL) was added. The mixture was stirred at room temperature for 1 h. The mixture was then extracted with dichloromethane. The organic layer was washed by brine, dried over anhydrous Na$_2$SO$_4$, filtered and concentrated. The crude product was purified by preparative TLC using petroleum ether/EtOAc as the developing solvents to afford the title compound. $^1$H NMR (400 MHz, CD$_3$OD) δ 9.07 (d, J=8.4 Hz, 1H), 8.28 (d, J=9.6 Hz, 1H), 8.22 (d, J=9.6 Hz, 1H), 7.82 (d, J=8.8 Hz, 1H), 4.26 (m, 1H), 3.36 (m, 1H), 3.09 (m, 1H); LC/MS [M+1]$^+$=214.1.

Intermediate 11

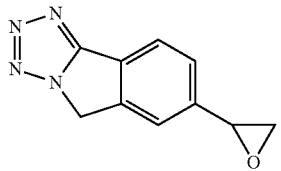

7-(oxiran-2-yl)-5H-tetrazolo[5,1-a]isoindole

Intermediate 11A

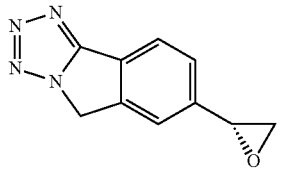 [SMILES: c1cc2c(cc1[C@@H]1CO1)Cn1nnnc1-2]

(R)-7-(oxiran-2-yl)-5H-tetrazolo[5,1-a]isoindole
(fast, enantiomer A)

Intermediate 11B

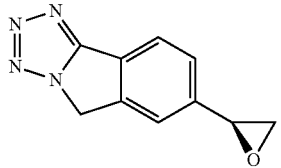 [SMILES: c1cc2c(cc1[C@H]1CO1)Cn1nnnc1-2]

(S)-7-(oxiran-2-yl)-5H-tetrazolo[5,1-a]isoindole
(slow, enantiomer B)

Step A: 4-bromo-2-(bromomethyl)benzonitrile

A mixture of 4-bromo-2-methylbenzonitrile (15.00 g, 74.2 mmol), NBS (13.87 g, 77.9 mmol) and benzoyl peroxide (0.63 g, 2.60 mmol) in CCl$_4$ (250 ml) was stirred at 80° C. for 6 h. The suspension was filtered and concentrated. The residue was purified via a BIOTAGE column using 0-10% EtOAc/petroleum ether as eluting solvents to afford the title compound.

Step B: 2-(azidomethyl)-4-bromobenzonitrile

A mixture of 4-bromo-2-(bromomethyl)benzonitrile (17.00 g, 61.8 mmol) and NaN$_3$ (4.42 g, 68.0 mmol) in DMF (120 mL) was stirred at 25° C. for 16 hours. The mixture was diluted with H$_2$O (120 mL), and then extracted with EtOAc three times. The combined organic phase was washed with brine five times, dried over Na$_2$SO$_4$, filtered and concentrated to afford the title compound. LC/MS [M+1]$^+$=237; 239.

Step C: 7-bromo-5H-tetrazolo[5,1-α]isoindole

A mixture of 2-(azidomethyl)-4-bromobenzonitrile (14.50 g, 61.1 mmol) in TFA (100 mL) was stirred at 18° C. for 2 h. The mixture was diluted with MeOH (100 mL) and the resulting white suspension was filtered and dried to afford the title compound. LC/MS [M+1]$^+$=237; 239.

Step D: 7-vinyl-5H-tetrazolo[5,1-α]isoindole

A mixture of 7-bromo-5H-tetrazolo[5,1-α]isoindole (2.00 g, 8.44 mmol), potassium vinyltrifluoroborate (1.36 g, 10.1 mmol), Pd(dppf)Cl$_2$ (614 mg, 0.84 mmol) and NEt$_3$ (1.75 mL, 12.6 mmol) in anhydrous EtOH (60 mL) was stirred at reflux for 6 hours under N$_2$. The mixture was concentrated and the residue was purified via a BIOTAGE column using 0-35% EtOAc/petroleum ether as the eluting solvents to afford the title compound. LC/MS [M+1]$^+$=185.

Step E: 7-(oxiran-2-yl)-5H-tetrazolo[5,1-α]isoindole m-CPBA (2.04 g, 6.51 mmol) was added in small portions to a stirred mixture of 7-vinyl-5H-tetrazolo[5,1-α]isoindole (800 mg, 4.34 mmol) in CHCl$_3$ (40 mL) at 5° C. The resulting mixture was stirred at 25° C. for 6 h. The mixture was diluted with DCM (20 mL), washed with saturated aq. Na$_2$SO$_3$ (20 mL), water (20 mL), and the mixture was then concentrated. The crude product was purified via a BIOTAGE column using 0-40% EtOAc/petroleum ether as the eluting solvents to afford the title compound. $^1$H NMR (400 MHz, CD$_3$OD) δ 8.01 (d, J=8.0 Hz, 1H), 7.70 (s, 1H), 7.61 (d, J=8.0 Hz, 1H), 5.52 (s, 2H), 4.06 (t, J=3.2 Hz, 1H), 3.23 (t, J=4.4 Hz, 1H), 2.86 (dd, J=5.2 Hz, 2.4 Hz, 1H); LC/MS [M+1]$^+$=201. 7-(oxiran-2-yl)-5H-tetrazolo[5,1-α]isoindole was then separated by chiral SFC eluting with 25% EtOH (0.05% NH$_4$OH)/CO$_2$ on a CHIRALPAK AY column to give the two following enantiomers.

(R)-7-(oxiran-2-yl)-5H-tetrazolo[5,1-α]isoindole: fast-eluting fraction. $^1$H NMR (400 MHz, CD$_3$OD) δ 8.01 (d, J=8.0 Hz, 1H), 7.70 (s, 1H), 7.61 (d, J=8.0 Hz, 1H), 5.52 (s, 2H), 4.06 (t, J=3.2 Hz, 1H), 3.23 (t, J=4.4 Hz, 1H), 2.86 (dd, J=5.2 Hz, 2.4 Hz, 1H); LC/MS [M+1]$^+$=201.

(S)-7-(oxiran-2-yl)-5H-tetrazolo[5,1-α]isoindole: slow-eluting fraction. LC/MS [M+1]$^+$=201.
$^1$H NMR (400 MHz, CD$_3$OD) δ 8.01 (d, J=8.0 Hz, 1H), 7.70 (s, 1H), 7.61 (d, J=8.0 Hz, 1H), 5.52 (s, 2H), 4.06 (t, J=3.2 Hz, 1H), 3.23 (t, J=4.4 Hz, 1H), 2.86 (dd, J=5.2 Hz, 2.4 Hz, 1H).

Intermediate 12

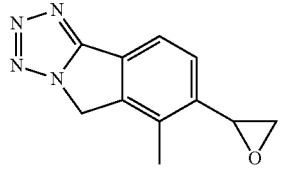 [SMILES: Cc1c(C2CO2)ccc2c1Cn1nnnc1-2]

6-methyl-7-(oxiran-2-yl)-5H-tetrazolo[5,1-a]isoindole

Step A: 3-(hydroxymethyl)-2-methylphenol

BH$_3$.Me$_2$S (10 M, 30 mL) was added dropwise to a solution of 3-hydroxy-2-methylbenzoic acid (10.00 g, 65.7 mmol) in THF (200 mL). The resulting solution was stirred at room temperature for 16 h. MeOH (60 mL) was added dropwise to the reaction mixture at 0° C. The mixture was then concentrated and extracted with EtOAc, and washed with 0.5 M HCl. The combined organic layer was dried over $Na_2SO_4$, filtered and concentrated to afford the title compound. $^1$H NMR (400 MHz, DMSO-$d_6$) δ 10.01 (s, 1H), 7.21-7.06 (m, 1H), 6.97 (d, J=7.4 Hz, 1H), 6.85 (d, J=7.8 Hz, 1H), 5.28 (t, J=5.3 Hz, 1H), 4.61-4.45 (m, 2H).

Step B: 4-bromo-3-(hydroxymethyl)-2-methylphenol

A solution of 3-(hydroxymethyl)-2-methylphenol (1.70 g, 10.4 mmol) in TFA (20 mL) was cooled to 0° C. and then NBS (1.85 g, 10.4 mmol) was added in portions. The resulting mixture was stirred at 0° C. for 1 h, concentrated, diluted with EtOAc, and washed with water. The combined organic layer was then concentrated and purified by flash chromatography on a silica gel column using 30-50% EtOAc/petroleum ether as the eluting solvents to afford the title compound.

Step C: 1-bromo-4-methoxy-2-(methoxymethyl)-3-methylbenzene

A solution of 4-bromo-3-(hydroxymethyl)-2-methylphenol (10.00 g, 46 mmol) and KOH (6.20 g, 110 mmol) in DMSO (60 mL) was stirred at room temperature for 10 min. MeI (17.00 g, 120 mmol) was added, the resulting mixture was stirred at room temperature for 20 h. The reaction mixture was partitioned between water and EtOAc. The organic layer was dried over $Na_2SO_4$, filtered and concentrated to afford the title compound.

Step D: 4-methoxy-2-(methoxymethyl)-3-methylbenzonitrile

A solution of 1-bromo-4-methoxy-2-(methoxymethyl)-3-methylbenzene (10.00 g, 41 mmol) and CuCN (11.00 g, 122 mmol) in DMF (100 mL) was stirred at 140° C. for 1.5 h. The reaction was cooled to room temperature, diluted with EtOAc and filtered through a pad of CELITE. The filtrate was washed with brine, dried over sodium sulfate, filtered and concentrated. The residue was purified by silica gel flash chromatography with 0-10% EtOAc/petroleum as the eluting solvents to afford the title compound.

Step E: 2-(bromomethyl)-4-hydroxy-3-methylbenzonitrile

To a solution of 4-methoxy-2-(methoxymethyl)-3-methylbenzonitrile (7.00 g, 36.6 mmol) in DCM (100 mL) was added dropwise $BBr_3$ (55.00 g, 0.22 mol) at −78° C. The resulting mixture was warmed to room temperature and stirred for 10 h. The reaction mixture was quenched by water at 0° C., and extracted with EtOAc. The organic layer was washed with brine, dried over sodium sulfate, filtered and then concentrated. The residue was then purified by silica gel flash chromatography using 10-40% EtOAc/petroleum ether as the eluting solvents to afford the title compound.

Step F: 2-(azidomethyl)-4-hydroxy-3-methylbenzonitrile

A solution of 2-(bromomethyl)-4-hydroxy-3-methylbenzonitrile (5.60 g, 24.8 mmol) and $NaN_3$ (2.00 g, 30.0 mmol) in DMF (40 mL) was stirred at room temperature for 10 h. The reaction mixture was extracted with EtOAc and water. The organic layer was washed with brine, dried over sodium sulfate, filtered and concentrated. The residue was purified by silica gel flash chromatography using 10-30% EtOAc/petroleum ether as the eluting solvents to afford the title compound. LC/MS [M+1]$^+$=189.

Step G: 6-methyl-5H-tetrazolo[5,1-α]isoindol-7-ol

A solution of 2-(azidomethyl)-4-hydroxy-3-methylbenzonitrile (1.00 g, 5.13 mmol) in TFA (6 mL) was stirred at room temperature for 2 h. The mixture was filtered and dried to afford the title compound. LC/MS [M+1]$^+$=189.

Step H: 6-methyl-5H-tetrazolo[5,1-α]isoindol-7-yl trifluoromethanesulfonate

To a solution of 6-methyl-5H-tetrazolo[5,1-a]isoindol-7-ol (200 mg, 1.1 mmol) in DCM was added TEA (1.20 g, 12 mmol) and $(Tf)_2O$ (600 mg) at 0° C. The resulting mixture was then stirred at room temperature for 5 h. The reaction mixture was diluted with EtOAc, washed with water and then dried with $Na_2SO_4$. The residue was then filtered and concentrated to afford the title compound. LC/MS [M+1]$^+$=321.

Step I: 6-methyl-7-vinyl-5H-tetrazolo[5,1-α]isoindole

A solution of 6-methyl-5H-tetrazolo[5,1-α]isoindol-7-yl-trifluoromethanesulfonate (300 mg, 0.94 mmol), potassium vinyltrifluoroborate (188 mg, 1.41 mmol), $PdCl_2(dppf)$ (30 mg, 5%) and TEA (190 mg, 1.87 mmol) in dioxane (10 mL) was heated at 70° C. for 16 h under $N_2$. The reaction mixture was concentrated, diluted with EtOAc, washed with brine and concentrated. The residue was purified by silica gel flash chromatography using 0-40% EtOAc/petroleum ether as the eluting solvents to afford the title compound. LC/MS [M+1]$^+$=199.

Step J: 6-methyl-7-(oxiran-2-yl)-5H-tetrazolo[5,1-α]isoindole m-CPBA (55%, 95 mg, 0.30 mmol) was added to a stirred mixture of 6-methyl-7-vinyl-5H-tetrazolo[5,1-α]isoindole (40 mg, 0.20 mmol) in $CHCl_3$ (4 mL) at 5° C. The resulting mixture was stirred at 25° C. for 6 h, and quenched by addition of saturated aqueous $Na_2S_2O_3$. The mixture was diluted with DCM (10 mL), washed with water (20 mL*2), and then concentrated. The crude product was then purified by preparative TLC using petroleum / EtOAc as the eluting solvents to afford the title compound. $^1$H NMR (400 MHz, $CDCl_3$) δ 7.90 (d, J=8.2 Hz, 1H), 7.49 (d, J=7.8 Hz, 1H), 5.29 (s, 2H), 4.10 (s, 1H), 3.26 (t, J=4.7 Hz, 1H), 2.73 (d, J=3.1 Hz, 1H), 2.50 (s, 3H); LC/MS [M+1]$^+$=215.

Intermediate 13A

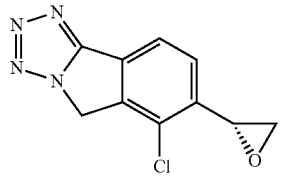 [SMILES: Clc1c([C@@H]2CO2)ccc2c1Cn1nnnc1-2]

(R)-6-chloro-7-(oxiran-2-yl)-5H-tetrazolo[5,1-a]isoindole (fast, enantiomer A)

Intermediate 13B

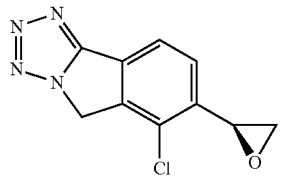 [SMILES: Clc1c([C@H]2CO2)ccc2c1Cn1nnnc1-2]

(S)-6-chloro-7-(oxiran-2-yl)-5H-tetrazolo[5,1-a]isoindole (slow, enantiomer B)

Step A: N-(3-chloro-2-methylphenyl)acetamide

To a solution of 3-chloro-2-methylaniline (10.00 g, 70.6 mmol) in EtOH (84 mL) was added acetic anhydride (8 mL, 84.8 mmol) at room temperature. The reaction mixture was stirred for 2 h and concentrated to afford the title compound. LC/MS [M+1]$^+$=184.

Step B: N-(4-bromo-3-chloro-2-methylphenyl)acetamide

To a solution of N-(3-chloro-2-methylphenyl)acetamide (13.00 g, 70.8 mmol) in AcOH (100 mL) was added Br$_2$ (10.9 mL, 0.212 mol) at 15° C. dropwise over 30 min. The solution was then stirred at room temperature for 2 h. The mixture was poured into ice water and stirred, filtered and dried to afford the title compound. LC/MS [M+1]$^+$=262; 264. $^1$H NMR (400 MHz, MeOD) δ 7.54-7.52 (d, J=8.8 Hz, 1H), 7.22-7.19 (d, J=8.4 Hz, 1H), 2.35 (s, 3H), 2.16 (s, 3H).

Step C: 4-bromo-3-chloro-2-methylaniline

To a solution of N-(4-bromo-3-chloro-2-methylphenyl)acetamide (18.50 g, 70.5 mmol) in EtOH (70 mL) was added conc. HCl (70 mL) at room temperature, and the soluation was heated at reflux overnight. The mixture was adjusted to pH7 with solid Na$_2$CO$_3$, and then extracted by EtOAc, dried and concentrated to afford the title compound. LC/MS [M+1]$^+$=220; 222. $^1$H NMR (400 MHz, CDCl$_3$) δ 7.24-7.22 (d, J=8.4 Hz, 1H), 6.48-6.46 (d, J=8.4 Hz, 1H), 2.26 (s, 3H).

Step D: 4-bromo-3-chloro-2-methylbenzonitrile

To a mixture of 4-bromo-3-chloro-2-methylaniline (6.60 g, 30 mmol) in 200 mL of CH$_3$CN was added BF$_3$Et$_2$O (6 mL, 43.5 mmol). The solution was cooled to 0° C. and t-butyl nitrite (4.75 g, 46.1 mmol) was added. After being stirred for 1 h, the solution was transferred to a mixture of CuCN (8.04 g, 89.8 mmol) and NaCN (14.70 g, 300 mmol) in 200 mL of water at 0° C. The resulting mixture was then heated at 70° C. for 3 h. The mixture was concentrated, extracted with EtOAc, purified with a silica gel column using 0 to 3.2% EtOAc/petroleum ether as the eluting solvents to afford the title compound. LC/MS [M+1]$^+$=230; 232. $^1$H NMR (400 MHz, CDCl$_3$) δ 7.61-7.59 (d, J=8.4 Hz, 1H), 7.39-7.37 (d, J=8.4 Hz, 1H), 2.68 (s, 3H).

Step E: 4-bromo-2-(bromomethyl)-3-chlorobenzonitrile

To a mixture of 4-bromo-3-chloro-2-methylbenzonitrile (5.00 g, 21.7 mmol) in CCl$_4$ (85 mL) was added NBS (4.17 g, 23.4 mmol) and BPO (526 mg, 2.17 mmol). The mixture was heated to reflux and stirred for 16 h under N$_2$ protection. The mixture was concentrated in vacuo, and the residue was purified by silica gel chromatography using 0 to 3.2% EtOAc/petroleum ether as the eluting solvents to afford the title compound. LC/MS [M+1]$^+$=308; 310; 312. $^1$H NMR (400 MHz, CDCl$_3$) δ 7.67-7.65 (d, J=7.2 Hz, 1H), 7.46-7.44 (d, J=8.4 Hz, 1H), 4.79 (s, 3H).

Step F: 2-(azidomethyl)-4-bromo-3-chlorobenzonitrile

To a solution of 4-bromo-2-(bromomethyl)-3-chlorobenzonitrile (5.60 g, 18.1 mmol) in DMF (30 mL) was added NaN$_3$ (1.41 g, 21.7 mmol). The mixture was stirred at room temperature for 16 h. The mixture was then extracted by MTBE and concentrated to afford the title compound. LC/MS [M+1]$^+$=271; 273.

Step G: 7-bromo-6-chloro-5H-tetrazolo[5,1-α]isoindole

A solution of 2-(azidomethyl)-4-bromo-3-chlorobenzonitrile (300 mg, 1.1 mmol) in 10 mL of toluene was heated at 140° C. for 0.5 hour by microwave radiation. The mixture was concentrated and purified on silica gel using 11% to 50% EtOAc/petroleum ether as the eluting solvents to afford the title compound. LC/MS [M+1]$^+$=271; 273. $^1$H NMR (400 MHz, DMSO-d$_6$) δ 8.08-7.99 (m, 2H), 5.72 (s, 2H).

Step H: 6-chloro-7-vinyl-5H-tetrazolo[5,1-α]isoindole

To a solution of 7-bromo-6-chloro-5H-tetrazolo[5,1-a]isoindole (500 mg, 1.84 mmol), potassium vinyltrifluoroborate (493 mg, 3.68 mmol) and Pd(dppf)Cl$_2$ (54 mg) in EtOH (10 mL) was added TEA (559 mg, 5.52 mmol) at room temperature. The resulting mixture was heated to 80° C. and stirred for 16 hours under N$_2$ protection. The mixture was filtered, and the cake was washed with EtOH. The combined filtrate was concentrated and the residue was purified by silica gel chromatography using 25% to 40% EtOAc/petroleum ether as the eluting solvents to afford the title compound. LC/MS [M+1]$^+$=219. $^1$H NMR (400 MHz, DMSO-d$_6$) δ 8.06-8.01 (m, 2H), 7.16-7.09 (m, 1H), 6.15-6.11 (m, 1H), 5.68-5.64 (m, 3H).

Step I: (R) 6-chloro-7-(oxiran-2-yl)-5H-tetrazolo[5,1-α]isoindole and (S) 6-chloro-7-(oxiran-2-yl)-5H-tetrazolo[5,1-α]isoindole and (S)-6-chloro-7-(oxiran-2-yl)-5H-tetrazolo[5,1-α]isoindole A mixture of 6-chloro-7-vinyl-5H-tetrazolo[5,1-α]isoindole (140 mg, 0.639 mmol) and m-CPBA (332 mg, 50%, 0.960 mmol) in DCM (10 mL) was stirred at room temperature for 16 h. The mixture was then heated to reflux and stirred for another 10 h. The mixture was concentrated and purified on a silica gel column using 16.6% to 25% EtOAc/petroleum ether as the eluting solvents. The resultant product was then separated by chiral SFC eluting with 40% EtOH (0.05% DEA)/CO$_2$ on CHIRALCEL OJ-3 column] to afford the title compounds.

(R)-6-chloro-7-(oxiran-2-yl)-5H-tetrazolo[5,1-α]isoindole: fast-eluting fraction. LC/MS [M+1]$^+$=235.

(S)-6-chloro-7-(oxiran-2-yl)-5H-tetrazolo[5,1-α]isoindole: slow-eluting fraction. LC/MS [M+1]$^+$=235.

Intermediate 14

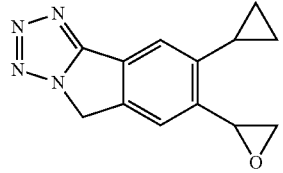 [SMILES: c1c2c(cc(C3CO3)c1C1CC1)Cn1nnnc1-2]

8-cyclopropyl-7-(oxiran-2-yl)-5H-tetrazolo[5,1-α]isoindole

Step A: 7-bromo-8-iodo-5H-tetrazolo[5,1-α] isoindole

To a flask was added 7-bromo-5H-tetrazolo[5,1-α]isoindole (Int. 11, step C; 2.00 g, 8.44 mmol) and TfOH (12.16 g, 81.0 mmol) at 0° C. Then NIS (3.80 g, 16.9 mmol) was added at 0° C. in portions. The mixture was stirred for at 0° C. for 0.5 h and then stirred at room temperature for 1 h. The mixture was concentrated, and purified by flash chromatography on a silica gel column using 0 to 40% EtOAc/petroleum ether as the eluting solvents to afford the title compound. LC/MS [M+1]$^+$=363; 364.

Step B: 7-bromo-8-cyclopropyl-5H-tetrazolo[5,1-α]isoindole

To a solution of 7-bromo-8-iodo-5H-tetrazolo[5,1-α]isoindole (2.50 g, 6.9 mmol) in 30 mL toluene and 10 mL H$_2$O was added cyclopropylboronic acid (237 mg, 2.76 mmol), Pd(dppf)Cl$_2$ (100 mg, 0.14 mmol) and K$_3$PO$_4$ (1.17 g, 5.51 mmol) at room temperature under N$_2$ protection. The resulting mixture was stirred at 80° C. for 18 h. The mixture was filtered, and the filtrate was concentrated. The resultant product was then purified by flash chromatography on a silica gel column using 0 to 40% EtOAc/petroleum ether as the eluting solvents to afford the title compound. LC/MS [M+1]$^+$=277; 279.

Step C: 8-cyclopropyl-7-vinyl-5H-tetrazolo[5,1-α]isoindole

To a solution of 7-bromo-8-cyclopropyl-5H-tetrazolo[5,1-α]isoindole (1.20 g, 4.3 mmol) in 30 mL of EtOH was added potassium vinyltrifluoroborate (697 mg, 5.2 mmol), Pd(dppf)Cl$_2$ (618 mg, 0.86 mmol) and Et$_3$N (651 mg, 6.5 mmol) at room temperature. The resulting mixture was stirred at 80° C. for 18 h under N₂ protection. The mixture was filtered, and the filtrate was concentrated. The resultant product was purified by flash chromatography on a silica gel column using 0 to 40% EtOAc/petroleum ether as the eluting solvents to give the title compound. LC/MS [M+1]⁺=225.

Step D: 8-cyclopropyl-7-(oxiran-2-yl)-5H-tetrazolo[5,1-α]isoindole

To a solution of 8-cyclopropyl-7-vinyl-5H-tetrazolo[5,1-]isoindole (600 mg, 2.68 mmol) in 10 mL of DCM was added m-CPBA (696 mg, 4.02 mmol) at room temperature. The resulting mixture was stirred at room temperature for 4 h. The mixture was then quenched by Na₂S₂O₃, extracted by DCM, dried over Na₂SO₄, filtered and concentrated. The residue was purified by flash chromatography on a silica gel column using 0 to 40% EtOAc/petroleum ether as the eluting solvents to afford the title compound. LC/MS [M+1]⁺=241.

Intermediate 15

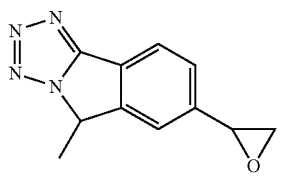 [SMILES: CC1c2cc(C3CO3)ccc2-c2nnnn21]

5-methyl-7-(oxiran-2-yl)-5H-tetrazolo[5,1-α]isoindole

Step A: 4-bromo-2-ethylbenzonitrile

A solution of 4-bromo-2-methylbenzonitrile (4.00 g, 20.4 mmol) in THF (40 mL) was added dropwise to a solution of lithium diisopropylamide (2.0 Min THF, 16 mL, 32.0 mmol) in THF (10 mL) over a period of 20 min at −78° C. under nitrogen atmosphere. After 2 h, iodomethane (3.48 g, 24.5 mmol) was added dropwise over a period of 20 min at the same temperature. The reaction mixture was allowed to warm to room temperature and stirred for 3 h. The mixture was re-cooled to 0° C. and acidified with 1 M hydrochloric acid to pH1. The aqueous layer was extracted with ethyl acetate several times. The combined organic layer was washed with brine, dried over anhydrous sodium sulfate, filtered and concentrated. The residue was then purified by flash chromatography on a silica gel column using 0-10% ethyl acetate/petroleum ether as the eluting solvents to give the title compound. ¹H NMR (400 MHz, CDCl₃) δ 7.46 (s, 1H), 7.44-7.35 (m, 2H), 2.81 (q, J=7.7 Hz, 2H), 1.26 (t, J=7.6 Hz, 3H).

Step B: 4-bromo-2-(1-bromoethyl)benzonitrile

A mixture of 4-bromo-2-ethylbenzonitrile (3.50 g, 16.7 mmol) and benzoic peroxyanhydride (0.81 g, 3.33 mmol) in CCl₄ (60 mL) was stirred in air for 5 minutes. NBS (3.56 g, 20.0 mmol) was then added and the mixture was stirred at 60° C. for 16 h. The mixture was then cooled to room temperature, and concentrated. The residue was purified by flash chromatography on a silica gel column using 0 to 50% ethyl acetate/petroleum ether as the eluting solvents to afford the title compound. ¹H NMR (400 MHz, CDCl₃) δ 7.87 (s, 1H), 7.58-7.47 (m, 2H), 5.45 (q, J=7.0 Hz, 1H), 2.07 (d, J=7.0 Hz, 3H).

Step C: 2-(1-azidoethyl)-4-bromobenzonitrile

To a solution of 4-bromo-2-(1-bromoethyl)benzonitrile (3.20 g, 11.1 mmol) in 10 mL of DMF was added NaN₃ (1.44 g, 22.2 mmol). The resulting mixture was stirred at room temperature for 12 h. The mixture was poured into water and extracted with EtOAc, dried and concentrated to afford the title compound. LC/MS [M+1]⁺=251; 253.

Step D: 7-bromo-5-methyl-5H-tetrazolo[5,1-a]isoindole

A solution of 2-(1-azidoethyl)-4-bromobenzonitrile (2.60 g, 10.36 mmol) in 15 mL of TFA was stirred at room temperature for 2 h. The solution was then poured into water and extracted with DCM. The residue was then dried, concentrated, and purified by flash chromatography on a silica gel column using 0-60% ethyl acetate/petroleum ether as the eluting solvents to afford the title compound. LC/MS [M+1]⁺=251; 253. ¹H NMR (400 MHz, CDCl₃) δ 7.91 (d, J=7.8 Hz, 1H), 7.81-7.69 (m, 2H), 5.54-5.44 (m, 1H), 1.89 (d, J=6.7 Hz, 3H).

Step E: 5-methyl-7-vinyl-5H-tetrazolo[5,1 -α] isoindole

To a mixture of 7-bromo-5-methyl-5H-tetrazolo[5,1-α] isoindole (1.40 g, 5.58 mmol) and potassium vinyltrifluoroborate (896 mg, 6.69 mmol) in 30 mL of EtOH was added TEA (846 mg, 8.36 mmol) and PdCl₂(dppf) (620 mg, 0.6 mmol) under N₂ atmosphere. The resulting mixture was heated under reflux overnight with N₂ protection. The mixture was cooled to room temperature, filtered and concentrated. The residue was then purified by flash chromatography on a silica gel column using 0-10% MeOH/DCM as the eluting solvents to afford the title compound. LC/MS [M+1]⁺=199. ¹H NMR (400 MHz, CDCl₃) δ 7.99 (d, J=8.2 Hz, 1H), 7.63-7.56 (m, 2H), 6.82 (dd, J=18 Hz, 11 Hz, 1H), 5.92 (d, J=18 Hz, 1H), 5.50-5.44 (m, 2H), 1.90 (d, J=6.7 Hz, 3H).

Step F: 5-methyl-7-(oxiran-2-yl)-5H-tetrazolo[5,1 -α]isoindole

To a solution of 5-methyl-7-vinyl-5H-tetrazolo[5,1-α] isoindole (720 mg, 3.63 mmol) in 40 mL of CH₂Cl₂ was added m-CPBA (940 mg, 5.45 mmol). The resulting mixture was stirred at room temperature for 12 h and then concentrated. The residue was purified by preparative TLC using 50% EtOAc/petroleum ether as the developing solvents to afford the title compound. LC/MS[M+1]⁺=215. ¹H NMR (400 MHz, CDCl₃) δ 8.01 (d, J=7.8 Hz, 1H), 7.60-7.51 (m, 1H), 7.46 (s, 1H), 5.47 (q, J=6.4 Hz, 1H), 4.01 (s, 1H), 3.25 (t, J=4.7 Hz, 1H), 2.82 (dt, J=5.7 Hz, 2.3 Hz, 1H), 1.88 (d, J=7.0 Hz, 3H).

Example 1

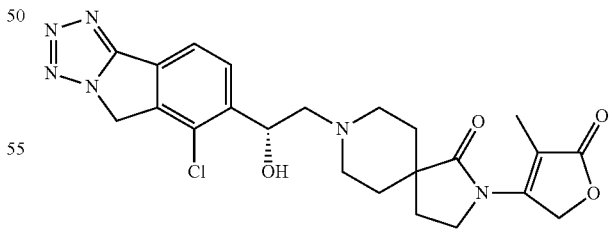

(R)-8-(2-(6-chloro-5H-tetrazolo[5,1-a]isoindol-7-yl)-2-hydroxyethyl)-2-(4-methyl-5-oxo-2,5-dihydrofuran-3-yl)-2,8-diazaspiro[4.5]decan-1-one A mixture of (R)-6-chloro-7-(oxiran-2-yl)-5H-tetrazolo[5,1-α]isoindole (Int. 13A, 50 mg, 0.21 mmol, first eluting in SFC) and 2-(4-methyl-5-oxo-2,5-dihydrofuran-3-yl)-2,8- diazaspiro[4.5]decan-1-one (Int. 2; 48 mg, 0.19 mmol) in EtOH (5 mL) was stirred at 80° C. for 2 h. The mixture was concentrated and the residue was purified by preparative TLC (EtOAc: MeOH=4:1) to afford the title compound.

$^1$H NMR (400 MHz, CDCl$_3$) δ 8.00-7.95 (m, 2H), 5.33-5.23 (m, 5H), 4.04-4.01 (m, 2H), 3.20-3.17 (m, 1H), 2.86-2.81 (m, 2H), 2.60-2.55 (m, 1H), 2.35-2.31 (m, 2H), 2.17-1.98 (m, 7H), 1.65-1.58 (m, 2H); LC/MS: [(M+1)]$^+$=485.0.

TABLE 1

Examples 2-6 were synthesized followed a similar procedure to that described in Example 1.

| EXAMPLES | INTERMEDIATES | STRUCTURES | Characterization |
|---|---|---|---|
| 2 | 13B, 2 | (S)-8-(2-(6-chloro-5H-tetrazolo[5,1-a]isoindol-7-yl)-2-hydroxyethyl)-2-(4-methyl-5-oxo-2,5-dihydrofuran-3-yl)-2,8-diazaspiro[4.5]decan-1-one | LC/MS [M + 1]$^+$ = 485.1 |
| 3 | 11A, 6B | (5S,6R)-6-fluoro-8-((R)-2-hydroxy-2-(5H-tetrazolo[5,1-a]isoindol-7-yl)ethyl)-2-(4-methyl-5-oxo-2,5-dihydrofuran-3-yl)-2,8-diazaspiro[4.5]decan-1-one | LC/MS [M + 1]$^+$ = 469.1 |
| 4 | 11A, 6A | (5R,6S)-6-fluoro-8-((R)-2-hydroxy-2-(5H-tetrazolo[5,1-a]isoindol-7-yl)ethyl)-2-(4-methyl-5-oxo-2,5-dihydrofuran-3-yl)-2,8-diazaspiro[4.5]decan-1-one | LC/MS [M + 1]$^+$ = 469.2 |
| 5 | 11B, 6B | (5S,6R)-6-fluoro-8-((S)-2-hydroxy-2-(5H-tetrazolo[5,1-a]isoindol-7-yl)ethyl)-2-(4-methyl-5-oxo-2,5-dihydrofuran-3-yl)-2,8-diazaspiro[4.5]decan-1-one | LC/MS [M + 1]$^+$ = 469.2 |

TABLE 1-continued

Examples 2-6 were synthesized followed a similar procedure to that described in Example 1.

| EXAMPLES | INTERMEDIATES | STRUCTURES | Characterization |
|---|---|---|---|
| 6 | 11B, 6A | 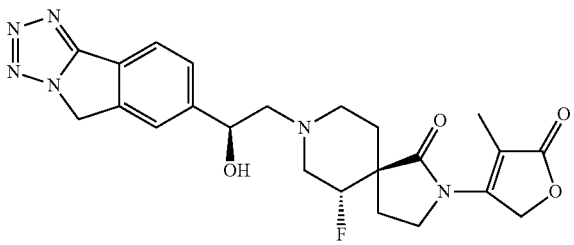 [SMILES: CC1=C(N2CC[C@]3(CCN(C[C@@H](O)c4ccc5c(c4)Cn4nnnc4-5)C[C@H]3F)C2=O)COC1=O] (5R,6S)-6-fluoro-8-((S)-2-hydroxy-2-(5H-tetrazolo[5,1-a]isoindol-7-yl)ethyl)-2-(4-methyl-5-oxo-2,5-dihydrofuran-3-yl)-2,8-diazaspiro[4.5]decan-1-one | LC/MS [M + 1]$^+$ = 469.2 |

Example 7A

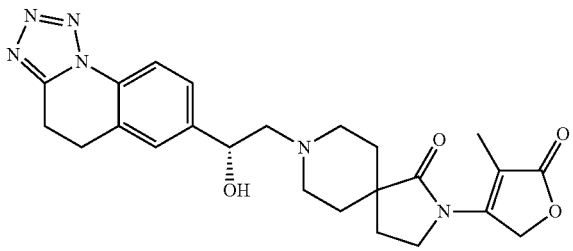

(R)-8-(2-(4,5-dihydrotetrazolo[1,5-a]quinolin-7-yl)-2-hydroxyethyl)-2-(4-methyl-5-oxo-2,5-dihydrofuran-3-yl)-2,8-diazaspiro[4.5]decan-1-one

Example 7B

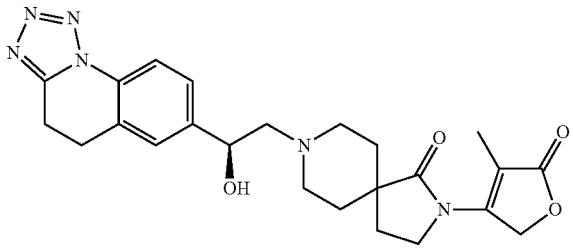 [SMILES: CC1=C(N2CCC3(CCN(C[C@@H](O)c4ccc5c(c4)CCc4nnnn4-5)CC3)C2=O)COC1=O]

(S)-8-(2-(4,5-dihydrotetrazolo[1,5-a]quinolin-7-yl)-2-hydroxyethyl)-2-(4-methyl-5-oxo-2,5-dihydrofuran-3-yl)-2,8-diazaspiro[4.5]decan-1-one The mixture of 7-(oxiran-2-yl)-4,5-dihydrotetrazolo[1,5-α]quinoline (Int. 8; 150 mg, 0.71 mmol) and TEA (107 mg, 1.06 mmol), 2-(4-methyl-5-oxo-2,5-dihydrofuran-3-yl)-2,8-diazaspiro[4.5]decan-1-one (Int. 2; 212 mg, 0.85 mmol) in EtOH (5 mL) was stirred at 90° C. for 1 h. The mixture was concentrated and the residue was purified by TLC using DCM/MeOH=10/1 as the developing solvents. This was followed by chiral SFC on a CHIRALPAK AD column using 40% EtOH (0.2% NH$_4$OH)/CO$_2$ as the eluting solvents to give the title compounds:

(R)-8-(2-(4,5-dihydrotetrazolo[1,5-α]quinolin-7-yl)-2-hydroxyethyl)-2-(4-methyl-5-oxo-2,5-dihydrofuran-3-yl)-2,8-diazaspiro[4.5]decan-1-one: 16 mg, fast eluting product.

LC/MS[M+1]$^+$=465.2. $^1$H NMR (400 MHz, CDCl$_3$) δ 7.96 (d, J=8.0 Hz, 1H), 7.47 (s, 1H), 7.41 (d, J=8.0 Hz, 1H), 5.25 (s, 2H), 4.85 (dd, J=9.6 Hz, 3.2 Hz, 1H), 4.03 (t, J=6.8 Hz, 2H), 3.35 (t, J=8.0 Hz, 2H), 3.14-3.21 (m, 3H), 2.90-2.94 (m, 1H), 2.66-2.68 (m, 2H), 2.43-2.61 (m, 5H), 2.15 (t, J=7.2 Hz, 2H), 2.08 (s, 3H), 1.68 (m, 2H).

(S)-8-(2-(4,5-dihydrotetrazolo[1,5 -α]quinolin-7-yl)-2-hydroxyethyl)-2-(4-methyl-5-oxo-2,5-dihydrofuran-3-yl)-2,8-diazaspiro[4.5]decan-1-one: 13 mg, slow eluting product.

LC/MS[M+1]$^+$=465.2. $^1$H NMR (400 MHz, CDCl$_3$) δ 7.95 (d, J=8.4 Hz, 1H), 7.47 (s, 1H), 7.40 (d, J=8.0 Hz, 1H), 5.24 (s, 2H), 4.83 (dd, J=10 Hz, 4.0 Hz, 1H), 4.03 (t, J=7.2 Hz, 2H), 3.34 (t, J=7.2 Hz, 2H), 2.90-3.15 (m, 7H), 2.45-2.65 (m, 4H), 2.15 (t, J=7.2 Hz, 2H), 2.03 (s, 3H), 1.73 (m, 2H).

TABLE 2

Examples 8-26 were synthesized followed the procedure as described in Example 7.

| EXAMPLES | INTERMEDIATES | STRUCTURES | Characterization | Chiral assignment |
|---|---|---|---|---|
| 8 | 11, 2 | (R)-8-(2-hydroxy-2-(5H-tetrazolo[5,1-a]isoindol-7-yl)ethyl)-2-(4-methyl-5-oxo-2,5-dihydrofuran-3-yl)-2,8-diazaspiro[4.5]decan-1-one | LC/MS [M + 1]⁺ = 451.1 | Fast 60% MeOH (0.05% DEA)/CO$_2$ on Chiralpal AD column |
| 9 | 11, 2 | (S)-8-(2-hydroxy-2-(5H-tetrazolo[5,1-a]isoindol-7-yl)ethyl)-2-(4-methyl-5-oxo-2,5-dihydrofuran-3-yl)-2,8-diazaspiro[4.5]decan-1-one | LC/MS [M + 1]⁺ = 451.1 | Slow 60% MeOH (0.05% DEA)/CO$_2$ on Chiralpal AD column |
| 10 | 9, 2 | (R)-8-(2-hydroxy-2-(6-methyl-4,5-dihydrotetrazolo[1,5-a]quinolin-7-yl)ethyl)-2-(4-methyl-5-oxo-2,5-dihydrofuran-3-yl)-2,8-diazaspiro[4.5]decan-1-one | LC/MS [M + 1]⁺ = 479.2 | Fast 40% MeOH (0.2% NH4OH)/CO2 on CHIRALPAK AD column |
| 11 | 9, 2 | (S)-8-(2-hydroxy-2-(6-methyl-4,5-dihydrotetrazolo[1,5-a]quinolin-7-yl)ethyl)-2-(4-methyl-5-oxo-2,5-dihydrofuran-3-yl)-2,8-diazaspiro[4.5]decan-1-one | LC/MS [M + 1]⁺ = 479.2 | Slow 40% MeOH (0.2% NH4OH)/CO2 on CHIRALPAK AD column |

TABLE 2-continued

Examples 8-26 were synthesized followed the procedure as described in Example 7.

| EXAMPLES | INTERMEDIATES | STRUCTURES | Characterization | Chiral assignment |
|---|---|---|---|---|
| 12 | 8, 4B | 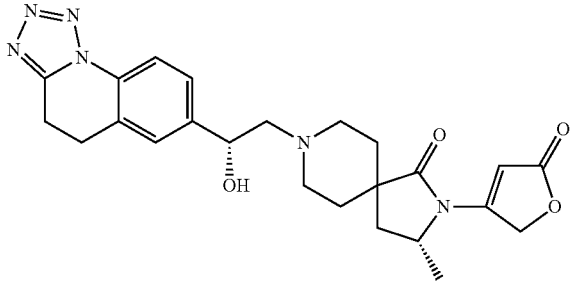 [SMILES: C[C@@H]1CC2(CCN(C[C@H](O)c3ccc4c(c3)CCc3nnnn3-4)CC2)C(=O)N1C1=CC(=O)OC1]<br>(R)-8-((R)-2-(4,5-dihydrotetrazolo[1,5-a]quinolin-7-yl)-2-hydroxyethyl)-3-methyl-2-(5-oxo-2,5-dihydrofuran-3-yl)-2,8-diazaspiro[4.5]decan-1-one | LC/MS [M + 1]$^+$ = 465.2 | Fast 60% EtOH (0.05% DEA)/ CO2 on CHIRALPAK AD column |
| 13 | 8, 4A | 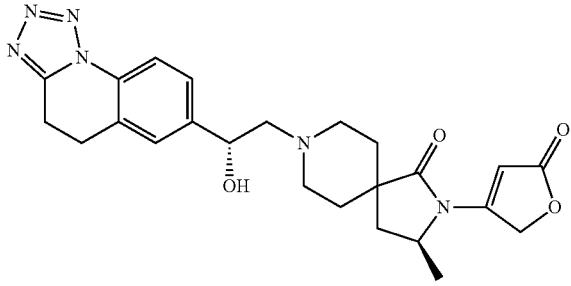 [SMILES: C[C@H]1CC2(CCN(C[C@H](O)c3ccc4c(c3)CCc3nnnn3-4)CC2)C(=O)N1C1=CC(=O)OC1]<br>(S)-8-((R)-2-(4,5-dihydrotetrazolo[1,5-a]quinolin-7-yl)-2-hydroxyethyl)-3-methyl-2-(5-oxo-2,5-dihydrofuran-3-yl)-2,8-diazaspiro[4.5]decan-1-one | LC/MS [M + 1]$^+$ = 465.2 | Fast 60% EtOH (0.05% DEA)/ CO2 on CHIRALPAK AD column |
| 14 | 8, 4B | 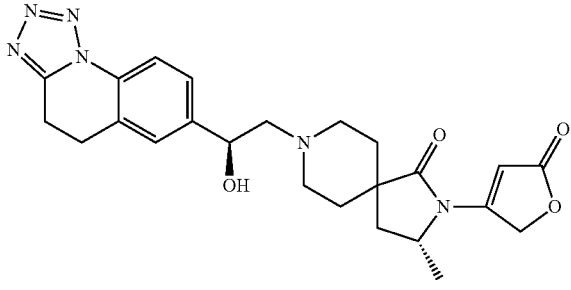 [SMILES: C[C@@H]1CC2(CCN(C[C@@H](O)c3ccc4c(c3)CCc3nnnn3-4)CC2)C(=O)N1C1=CC(=O)OC1]<br>(R)-8-((S)-2-(4,5-dihydrotetrazolo[1,5-a]quinolin-7-yl)-2-hydroxyethyl)-3-methyl-2-(5-oxo-2,5-dihydrofuran-3-yl)-2,8-diazaspiro[4.5]decan-1-one | LC/MS [M + 1]$^+$ = 465.2 | Slow 60% EtOH (0.05% DEA)/ CO2 on CHIRALPAK AD column |

TABLE 2-continued

Examples 8-26 were synthesized followed the procedure as described in Example 7.

| EXAMPLES | INTERMEDIATES | STRUCTURES | Characterization | Chiral assignment |
|---|---|---|---|---|
| 15 | 8, 4A | (S)-8-((S)-2-(4,5-dihydrotetrazolo[1,5-a]quinolin-7-yl)-2-hydroxyethyl)-3-methyl-2-(5-oxo-2,5-dihydrofuran-3-yl)-2,8-diazaspiro[4.5]decan-1-one | LC/MS [M + 1]$^+$ = 465.2 | Slow 60% EtOH (0.05% DEA)/ CO2 on CHIRALPAK AD column |
| 16 | 7, 4B | (R)-8-((R)-2-hydroxy-2-(tetrazolo[1,5-a]quinolin-7-yl)ethyl)-3-methyl-2-(5-oxo-2,5-dihydrofuran-3-yl)-2,8-diazaspiro[4.5]decan-1-one | LC/MS [M + 1]$^+$ = 463.2 | Fast 60% iPrOH (0.05% DEA)/ CO2 on CHIRALPAK AD column |
| 17 | 7, 4A | (S)-8-((R)-2-hydroxy-2-(tetrazolo[1,5-a]quinolin-7-yl)ethyl)-3-methyl-2-(5-oxo-2,5-dihydrofuran-3-yl)-2,8-diazaspiro[4.5]decan-1-one | LC/MS [M + 1]$^+$ = 463.2 | Fast 60% EtOH (0.05% DEA)/ CO2 on CHIRALPAK AD column |

TABLE 2-continued

Examples 8-26 were synthesized followed the procedure as described in Example 7.

| EXAMPLES | INTERMEDIATES | STRUCTURES | Characterization | Chiral assignment |
|---|---|---|---|---|
| 18 | 7, 4B | (R)-8-((S)-2-hydroxy-2-(tetrazolo[1,5-a]quinolin-7-yl)ethyl)-3-methyl-2-(5-oxo-2,5-dihydrofuran-3-yl)-2,8-diazaspiro[4.5]decan-1-one | LC/MS [M + 1]$^+$ = 463.2 | Slow 60% EtOH (0.05% DEA)/ $CO_2$ on CHIRALPAK AD column |
| 19 | 7, 4A | (S)-8-((S)-2-hydroxy-2-(tetrazolo[1,5-a]quinolin-7-yl)ethyl)-3-methyl-2-(5-oxo-2,5-dihydrofuran-3-yl)-2,8-diazaspiro[4.5]decan-1-one | LC/MS [M + 1]$^+$ = 463.2 | Slow 60% EtOH (0.05% DEA)/ $CO_2$ on CHIRALPAK AD column |
| 20 | 7, 2 | (R)-8-(2-hydroxy-2-(tetrazolo[1,5-a]quinolin-7-yl)ethyl)-2-(4-methyl-5-oxo-2,5-dihydrofuran-3-yl)-2,8-diazaspiro[4.5]decan-1-one | LC/MS [M + 1]$^+$ = 463.2 | Fast 40% MeOH (0.2% NH4OH)/ $CO_2$ on CHIRALPAK AD column |
| 21 | 7, 2 | (S)-8-(2-hydroxy-2-(tetrazolo[1,5-a]quinolin-7-yl)ethyl)-2-(4-methyl-5-oxo-2,5-dihydrofuran-3-yl)-2,8-diazaspiro[4.5]decan-1-one | LC/MS [M + 1]$^+$ = 463.2 | Slow 40% MeOH (0.2% NH4OH)/ $CO_2$ on CHIRALPAK AD column |

TABLE 2-continued

Examples 8-26 were synthesized followed the procedure as described in Example 7.

| EXAMPLES | INTERMEDIATES | STRUCTURES | Characterization | Chiral assignment |
|---|---|---|---|---|
| 22 | 10, 2 | (R)-8-(2-hydroxy-2-(tetrazolo[1,5-a][1,5]naphthyridin-7-yl)ethyl)-2-(4-methyl-5-oxo-2,5-dihydrofuran-3-yl)-2,8-diazaspiro[4.5]decan-1-one | LC/MS [M + 1]$^+$ = 464.2 | Slow 40% MeOH (0.2% NH4OH)/ CO2 on CHIRALPAK AD column |
| 23 | 12, 2 | (R)-8-(2-hydroxy-2-(6-methyl-5H-tetrazolo[5,1-a]isoindol-7-yl)ethyl)-2-(4-methyl-5-oxo-2,5-dihydrofuran-3-yl)-2,8-diazaspiro[4.5]decan-1-one | LC/MS [M + 1]$^+$ = 465.2 | Fast 60% EtOH (0.05% DEA)/ CO2 on CHIRALPAK AD column |
| 24 | 12, 2 | (S)-8-(2-hydroxy-2-(6-methyl-5H-tetrazolo[5,1-a]isoindol-7-yl)ethyl)-2-(4-methyl-5-oxo-2,5-dihydrofuran-3-yl)-2,8-diazaspiro[4.5]decan-1-one | LC/MS [M + 1]$^+$ = 465.2 | Slow 60% EtOH (0.05% DEA)/ CO2 on CHIRALPAK AD column |
| 25 | 14, 2 | (R)-8-(2-(8-cyclopropyl-5H-tetrazolo[5,1-a]isoindol-7-yl)-2-hydroxyethyl)-2-(4-methyl-5-oxo-2,5-dihydrofuran-3-yl)-2,8-diazaspiro[4.5]decan-1-one | LC/MS [M + 1]$^+$ = 491.2 | Fast 60% EtOH (0.05% DEA)/ CO2 on CHIRALPAK AD column |

TABLE 2-continued

Examples 8-26 were synthesized followed the procedure as described in Example 7.

| EXAMPLES | INTERMEDIATES | STRUCTURES | Characterization | Chiral assignment |
|---|---|---|---|---|
| 26 | 14, 2 | (S)-8-(2-(8-cyclopropyl-5H-tetrazolo[5,1-a]isoindol-7-yl)-2-hydroxyethyl)-2-(4-methyl-5-oxo-2,5-dihydrofuran-3-yl)-2,8-diazaspiro[4.5]decan-1-one | LC/MS [M + 1]⁺ 491.2 | Slow 60% EtOH (0.05% DEA)/CO2 on CHIRALPAK AD column |

Example 27A

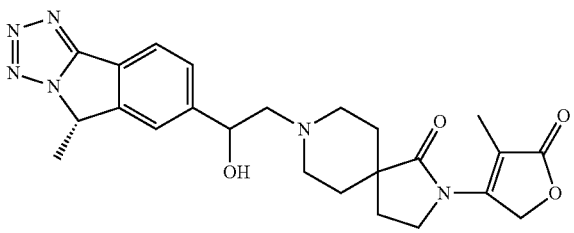 [SMILES: CC1=C(N2CCC3(CCN(CC(O)c4ccc5c(c4)[C@H](C)n4nnnc4-5)CC3)C2=O)COC1=O]

8-(2-hydroxy-2-((S)-5-methyl-5H-tetrazolo[5,1-α]isoindol-7-yl)ethyl)-2-(4-methyl-5-oxo-2,5-dihydrofuran-3-yl)-2,8-diazaspiro[4.5]decan-1-one

Example 27B

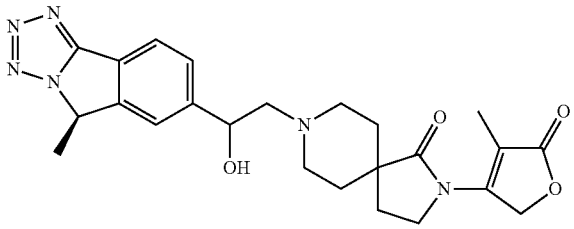 [SMILES: CC1=C(N2CCC3(CCN(CC(O)c4ccc5c(c4)[C@@H](C)n4nnnc4-5)CC3)C2=O)COC1=O]

8-(2-hydroxy-2-((R)-5-methyl-5H-tetrazolo[5,1-α]isoindol-7-yl)ethyl)-2-(4-methyl-5-oxo-2,5-dihydrofuran-3-yl)-2,8-diazaspiro[4.5]decan-1-one 8-(2-hydroxy-2-(5-methyl-5H-tetrazolo[5,1-α]isoindol-7-yl)ethyl)-2-(4-methyl-5-oxo-2,5-dihydrofuran-3-yl)-2,8-diazaspiro[4.5]decan-1-one: To a solution of 5-methyl-7-(oxiran-2-yl)-5H-tetrazolo[5,1-α]isoindole (Int. 15; 200 mg, 0.93 mmol) in 20 mL of EtOH was added 2-(4-methyl-5-oxo-2,5-dihydrofuran-3-yl)-2,8-diazaspiro[4.5]decan-1-one (Int. 2; 233 mg, 0.93 mmol). The resulting mixture was stirred at 60° C. for 12 h, cooled and concentrated. The residue was purified by preparative TLC using 20% MeOH/EtOAc as the developing solvents to afford the title compound. The title compound was then further separated by SFC on CHIRALPAK OJ column using 40% EtOH (0.05% DEA)/CO₂ as the eluting solvents to afford a pair of enantiomers.

8-(2-hydroxy-2-((S)-5-methyl-5H-tetrazolo[5,1-α]isoindol-7-yl)ethyl)-2-(4-methyl-5-oxo-2,5-dihydrofuran-3-yl)-2,8-diazaspiro[4.5]decan-1-one: (FAST).

LC/MS[M+1]⁺=465.2. ¹H NMR (400 MHz, CDCl₃) δ 7.99 (d, J=7.8 Hz, 1H), 7.68 (s, 1H), 7.52 (d, J=7.8 Hz, 1H), 5.46 (q, J=6.7 Hz, 1H), 5.27 (s, 2H), 4.87 (dd, J=11 Hz, 2.7 Hz, 1H), 4.04 (t, J=6.8 Hz, 2H), 3.12-3.22 (m, 1H), 2.85 (d, J=12 Hz, 1H), 2.67 (dd, J=12 Hz, 2.9 Hz, 1H), 2.43-2.60 (m, 2H), 2.31 (t, J=10 Hz, 1H), 2.16 (t, J=7.0 Hz, 2H), 2.00-2.11 (m, 4H), 1.89 (d, J=6.7 Hz, 3H), 1.52-1.75 (m, 3H).

8-(2-hydroxy-2-((R)-5-methyl-5H-tetrazolo[5,1-α]isoindol-7-yl)ethyl)-2-(4-methyl-5-oxo-2,5-dihydrofuran-3-yl)-2,8-diazaspiro[4.5]decan-1-one: 40 mg, (SLOW). LC/MS [M+1]⁺=465.2.

¹H NMR (400 MHz, CDCl₃) δ 7.98 (d, J=7.8 Hz, 1H), 7.69 (s, 1H), 7.51 (d, J=7.8 Hz, 1H), 5.47 (q, J=6.7 Hz, 1H), 5.26 (s, 2H), 4.81-4.93 (m, 1H), 4.04 (t, J=6.8 Hz, 2H), 3.16 (d, J=11 Hz, 1H), 2.80-2.88 (m, 1H), 2.63-2.70 (m, 1H), 2.43-2.58 (m, 2H), 2.31 (t, J=10 Hz, 1H), 2.16 (t, J=6.8 Hz, 2H), 1.96-2.11 (m, 5H), 1.88 (d, J=7.0 Hz, 3H), 1.60 (t, J=16 Hz, 2H).

Example 27C

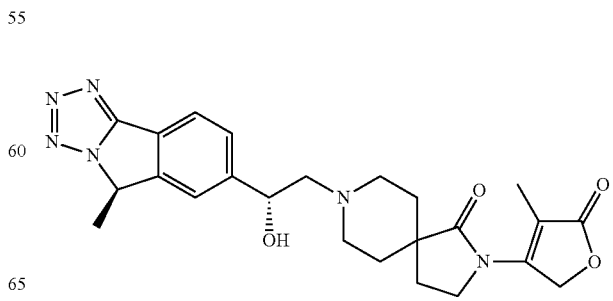

8-((R)-2-hydroxy-2-((R)-5-methyl-5H-tetrazolo[5,1-a]isoindol-7-yl)ethyl)-2-(4-methyl-5-oxo-2,5-dihydrofuran-3-yl)-2,8-diazaspiro[4.5]decan-1-one Example 27D

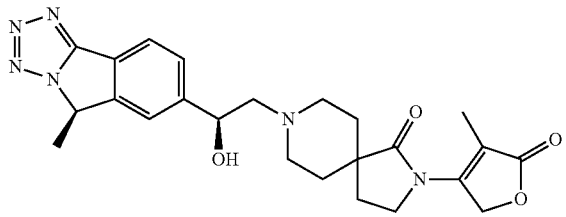 [SMILES: CC1=C(N2CCC3(CCN(C[C@@H](O)c4ccc5c(c4)[C@@H](C)n4nnnc4-5)CC3)C2=O)COC1=O]

8-((S)-2-hydroxy-2-((R)-5-methyl-5H-tetrazolo[5,1-a]isoindol-7-yl)ethyl)-2-(4-methyl-5-oxo-2,5-dihydrofuran-3-yl)-2,8-diazaspiro[4.5]decan-1-one 8-(2-hydroxy-2-((R)-5-methyl-5H-tetrazolo[5,1-a]isoindol-7-yl)ethyl)-2-(4-methyl-5-oxo-2,5-dihydrofuran-3-yl)-2,8-diazaspiro[4.5]decan-1-one (mixture of two diastereomers) (Int. 27B; 24.5 mg, 0.053 mmol) was separated on a chiral AS column eluted with 40% MeOH (0.05NH$_4$OH)/CO$_2$, at 10 MPa to give 8-((R)-2-hydroxy-2-((R)-5-methyl-5H-tetrazolo[5,1-a]isoindol-7-yl)ethyl)-2-(4-methyl-5-oxo-2,5-dihydrofuran-3-yl)-2,8-diazaspiro[4.5]decan-1-one (FAST, enantiomer A), LC/MS[M+1]$^+$=464.99, $^1$H NMR (500 MHz, CD$_3$Cl) δ 8.023-8.007 (d, J=7.9 Hz, 1H), 7.708-7.699(d, J=4.7 Hz, 1H), 7.551-7.535 (d, J=8 Hz, 1H), 5.490-5.476 (m, 1H), 5.288 (s, 2H), 4.908-4.880 (m, 1H), 4.071-4.043 (t, J=7.1 Hz, 2H), 3.188-3.156 (m, 1H), 2.878-2.838 (m, 1H), 2.705-2.680(m, 1H), 2.601-2.560(t, J=9.2 Hz, 1H), 2.518-2.493 (m, 1H), 3.344-2.300 (t, J=9.2 Hz, 1H), 2.190-2.164 (m, 2H), 2.069 (s, 3H), 2.091-2.010 (m, 2H), 1.915-1.901 (d, J=67.0 Hz, 3H), 1.664-1.619(m, 2H), and 8-((S)-2-hydroxy-2-((R)-5-methyl-5H-tetrazolo[5,1-a]isoindol-7-yl)ethyl)-2-(4-methyl-5-oxo-2,5-dihydrofuran-3-yl)-2,8-diazaspiro[4.5]decan-1-one (SLOW, enantiomer B), LC/MS[M+1]$^+$=464.97, $^1$H NMR (500 MHz, CD$_3$Cl) δ 8.023-8.007 (d, J=7.9 Hz, 1H), 7.708-7.699(d, J=4.7 Hz, 1H), 7.551-7.535 (d, J=8 Hz, 1H), 5.490-5.476 (m, 1H), 5.288 (s, 2H), 4.908-4.880 (m, 1H), 4.071-4.043 (t, J=7.1 Hz, 2H), 3.188-3.156 (m, 1H), 2.878-2.838 (m, 1H), 2.705-2.680 (m, 1H), 2.601-2.560(t, J=9.2 Hz, 1H), 2.518-2.493 (m, 1H), 3.344-2.300 (t, J=9.2 Hz, 1H), 2.190-2.164 (m, 2H), 2.069 (s, 3H), 2.091-2.010 (m, 2H), 1.908-2.894 (d, J=6.9 Hz, 3H), 1.657-1.590 (m, 2H).

Example 28

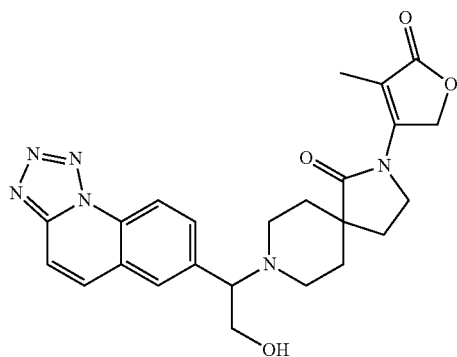 [SMILES: CC1=C(N2CCC3(CCN(C(CO)c4ccc5c(ccc6nnnn65)c4)CC3)C2=O)COC1=O]

8-(2-hydroxy-1-(tetrazolo[1,5-a]quinolin-7-yl)ethyl)-2-(4-methyl-5-oxo-2,5-dihydrofuran-3-yl)-2,8-diazaspiro[4.5]decan-1-one Example 28A

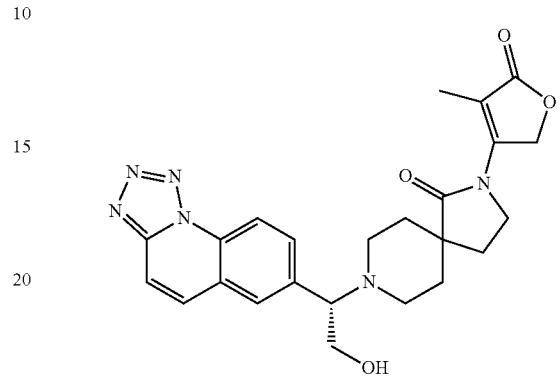

(S)-8-(2-hydroxy-1-(tetrazolo[1,5-a]quinolin-7-yl)ethyl)-2-(4-methyl-5-oxo-2,5-dihydrofuran-3-yl)-2,8-diazaspiro[4.5]decan-1-one 8-(2-hydroxy-1-(tetrazolo[1,5-a]quinolin-7-yl)ethyl)-2-(4-methyl-5-oxo-2,5-dihydrofuran-3-yl)-2,8-diazaspiro[4.5]decan-1-one: The mixture of 7-(oxiran-2-yl)tetrazolo[1,5-a]quinoline (Int. 7; 150 mg, 0.71 mmol), 2-(4-methyl-5-oxo-2,5-dihydrofuran-3-yl)-2,8-diazaspiro[4.5]decan-1-one (Int. 2; 193 mg, 0.77 mmol) and Et$_3$N (107 mg, 1.06 mmol) in EtOH (6 mL) was heated under reflux for 4 hours. The mixture was concentrated and then purified by TLC using 10% MeOH/DCM to give the racemate 8-(2-hydroxy-1-(tetrazolo[1,5-a]quinolin-7-yl)ethyl)-2-(4-methyl-5-oxo-2,5 dihydrofuran-3-yl)-2,8-diazaspiro[4.5]decan-1-one. LC/MS [M+1]$^+$=463.2, $^1$H NMR (400 MHz, CD$_3$OD) δ 8.70 (d, J=8.4 Hz, 1H), 8.28 (s, 1H), 8.23 (d, J=9.2 Hz, 1H), 8.09 (d, J=8.4 Hz, 1H), 7.97 (d, J=9.6 Hz, 1H), 5.47 (m, 1H), 5.25 (d, J=8.8 Hz, 2H), 4.16 (d, J=6.4 Hz, 2H), 3.92-3.44 (m, 6H), 2.25-2.20 (m, 4H), 2.11-1.95 (m, 5H).

(S)-8-(2-hydroxy-1-(tetrazolo[1,5-a]quinolin-7-yl)ethyl)-2-(4-methyl-5-oxo-2,5-dihydrofuran-3-yl)-2,8-diazaspiro[4.5]decan-1-one:

The racemate 8-(2-hydroxy-1-(tetrazolo[1,5-a]quinolin-7-yl)ethyl)-2-(4-methyl-5-oxo-2,5 dihydrofuran-3-yl)-2,8-diazaspiro[4.5]decan-1-one was further separated via chiral SFC on a CHIRALPAK AD-H column eluting with 60% MeOH (0.05% DEA)/CO$_2$ to afford the title compound. LC/MS [M+1]$^+$=463.2. $^1$H NMR (400 MHz, CD$_3$OD) δ 8.68 (d, J=8.4 Hz, 1H), 8.22 (s, 1H), 8.19 (s, 1H), 8.03 (dd, J=8.4 Hz, 1.6 Hz, 1H), 7.94 (d, J=9.6 Hz, 1H), 5.32 (m, 1H), 5.23 (s, 2H), 4.13 (t, J=7.2 Hz, 2H), 3.66 (s, 1H), 3.55 (m, 2H), 3.30-3.08 (m, 3H), 2.28-2.10 (m, 4H), 1.97 (s, 3H).

Example 29

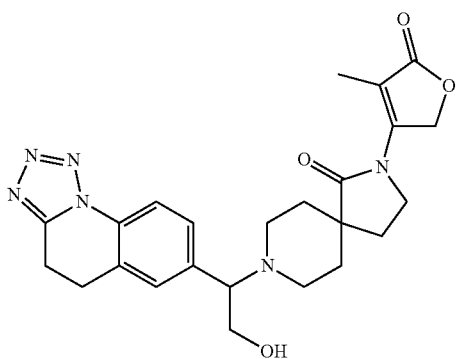 [SMILES: CC1=C(N2CCC3(CCN(C(CO)c4ccc5c(c4)CCc4nnnn4-5)CC3)C2=O)COC1=O]

8-(1-(4,5-dihydrotetrazolo[1,5-a]quinolin-7-yl)-2-hydroxyethyl)-2-(4-methyl-5-oxo-2,5-dihydrofuran-3-yl)-2,8-diazaspiro[4.5]decan-1-one A mixture of 7-(oxiran-2-yl)-4,5-dihydrotetrazolo[1,5-α]quinoline (Int. 8; 150 mg, 0.71 mmol), TEA (107 mg, 1.06 mmol), and 2-(4-methyl-5-oxo-2,5-dihydrofuran-3-yl)-2,8-diazaspiro[4.5]decan-1-one (Int. 2; 212 mg, 0.85 mmol) in EtOH (5 mL) was stirred at 90° C. for 1 hour. The mixture was then concentrated, and purified on TLC using 10% MeOH/DCM as the developing solvents to afford the title compound. LCMS[M+1]$^+$=465.2. $^1$H NMR (400 MHz, CD$_3$OD) δ 8.07 (d, J=8.4 Hz, 1H), 7.72 (s, 1H), 7.70 (d, J=8.4 Hz, 1H), 5.19 (s, 2H), 4.48 (s, 1H), 4.20 (m, 1H), 4.08 (m, 3H), 3.38 (m, 3H), 3.30-3.00 (m, 6H), 2.20 (m, 4H), 1.98 (s, 3H).

Example 30

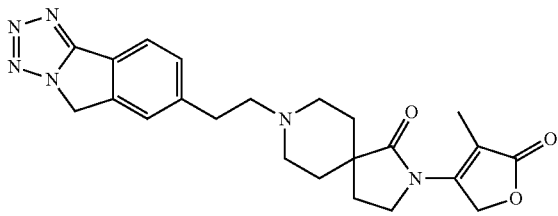 [SMILES: CC1=C(N2CCC3(CCN(CCc4ccc5c(c4)Cn4nnnc4-5)CC3)C2=O)COC1=O]

8-(2-(5H-tetrazolo[5,1-a]isoindol-7-yl)ethyl)-2-(4-methyl-5-oxo-2,5-dihydrofuran-3-yl)-2,8-diazaspiro[4.5]decan-1-one Step A: 7-allyl-5H-tetrazolo[5,1-α]isoindole A mixture of 7-bromo-5H-tetrazolo[5,1-α]isoindole (Int. 11, step C; 1.60 g, 6.8 mmol), allyltributylstannane (4.02 g, 12.2 mmol), Pd (PPh$_3$)$_4$ (780 mg, 0.04 mmol) and Pd (PPh$_3$)$_2$Cl$_2$ (300 mg) in 80 mL of dioxane was heated at 100° C. for 2 h under N$_2$ atmosphere. The mixture was filtered and concentrated. The residue was then purified by flash chromatography on a silica gel column using 0 to 25% EtOAc/petroleum ether as the eluting solvents to afford the title compound. LCMS[M+1]$^+$=199. $^1$H NMR (400 MHz, CDCl$_3$) δ 7.97 (d, J=7.8 Hz, 1H), 7.38-7.49 (m, 2H), 5.90-6.04 (m, 1H), 5.30 (s, 2H), 5.10-5.21 (m, 2H), 3.52 (d, J=6.7 Hz, 2H).

Step B: 3-(5H-tetrazolo[5,1-α]isoindol-7-yl)propane-1,2-diol

To a solution of 7-allyl-5H-tetrazolo[5,1-α]isoindole (400 mg, 2.0 mmol) in 10 mL of CH$_3$CN and 2 ml of H$_2$O was added NMO (585 mg, 5.04 mmol) and K$_2$OsO$_5$.2H$_2$O (40 mg, 0.1 mmol) under N$_2$ atmosphere. The resulting mixture was stirred at room temperature overnight. Excess Na$_2$SO$_3$ was added to the mixture. The mixture was stirred for 2 h, and the extracted with EtOAc (5×10 mL). The combined organic fraction was dried, filtered and concentrated. The residue was then washed with DCM and filtered to afford the title compound. LCMS[M+1]$^+$=233. $^1$H NMR (400 MHz, DMSO-d$_6$) δ 7.89 (d, J=7.8 Hz, 1H), 7.58 (s, 1H), 7.43 (d, J=7.8 Hz, 1H), 5.53 (s, 2H), 4.70-4.60 (m, 2H), 3.71-3.58 (m, 1H), 2.90 (dd, J=14 Hz, 3.9 Hz, 1H), 2.62 (dd, J=13 Hz, 8.2 Hz, 1H).

Step C: 2-(5H-tetrazolo[5,1-α]isoindol-7-yl)acetaldehyde

To a solution of 3-(5H-tetrazolo[5,1-α]isoindol-7-yl)propane-1,2-diol (40 mg, 0.17 mmol) in 3 mL of acetone and 1 mL of H$_2$O was added sodium periodate (36 mg, 0.17 mmol). The resulting mixture was stirred at room temperature for 40 min. 5 mL of H$_2$O was added and the mixture was extracted with ethyl acetate (20 mL). The combined organic fractions were washed with brine, dried over Na$_2$SO$_4$, and filtered. The solvent was evaporated under reduced pressure. The residue was then purified by preparative TLC using 50% EtOAc/DCM as the developing solvents to afford the title compound. LC/MS[(M+1)]$^+$=201.

Step D: 8-(2-(5H-tetrazolo[5,1-α]isoindol-7-yl) ethyl)-2-(4-methyl-5-oxo-2,5-dihydrofuran-3-yl)-2,8-diazaspiro[4.5]decan-1-one To a solution of 2-(5H-tetrazolo[5,1-α]isoindol-7-yl)acetaldehyde (40 mg, 0.2 mmol) and 2-(4-methyl-5-oxo-2,5-dihydrofuran-3-yl)-2,8-diazaspiro[4.5]decan-1-one (Int. 2; 58 mg, 0.2 mmol) in 4 mL of DCM was added NaBH(OAc)$_3$ (126 mg, 0.6 mmol), followed by 2 drops of AcOH. The resulting mixture was stirred at room temperature overnight, and then heated to reflux for 6 h. The mixture was concentrated, and the residue was purified by preparative TLC using 20% MeOH/EtOAc as the developing solvents to afford the title compound. LCMS [M+1]$^+$=435.2.

$^1$H NMR (400 MHz, CDCl$_3$) δ 7.98 (d, J=7.8 Hz, 1H), 7.49 (s, 1H), 7.45 (d, J=7.8 Hz, 1H), 5.32 (s, 2H), 5.26 (s, 2H), 4.02 (t, J=7.0 Hz, 2H), 3.00-2.90 (m, 4H), 2.74-2.64 (m, 2H), 2.33-2.21 (m, 2H), 2.14 (t, J=6.8 Hz, 2H), 2.08-1.95 (m, 5H), 1.58-1.50 (m, 2H).

Example 31

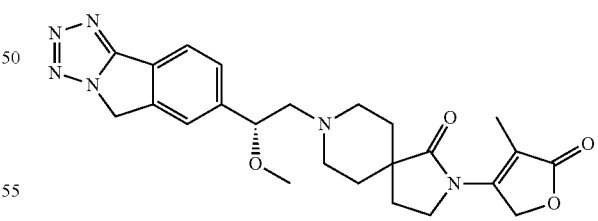

(R)-8-(2-methoxy-2-(5H-tetrazolo[5,1-a]isoindol-7-yl)ethyl)-2-(4-methyl-5-oxo-2,5-dihydrofuran-3-yl)-2,8-diazaspiro[4.5]decan-1-one Step A: (R)-2-methoxy-2-(5H-tetrazolo[5,1-α]isoindol-7-yl)ethanol To a solution of (S)-7-(oxiran-2-yl)-5H-tetrazolo[5,1-α]isoindole (Int. 11B; 80 mg, 0.4 mmol) in 5 mL of MeOH was added TsOH (8 mg, 0.04 mmol). The resulting mixture was stirred at 70° C. for 16 h, and concentrated to afford the title compound. LCMS[M+1]⁺=233.

Step B: (R)-2-methoxy-2-(5H-tetrazolo[5,1-α]isoindol-7-yl)acetaldehyde DMP (200 mg, 0.48 mmol) was added to a solution of (R)-2-methoxy-2-(5H-tetrazolo[5,1-α]isoindol-7-yl)ethanol (110 mg, 0.47 mmol) in DCM (5 mL) at room temperature. The mixture was stirred at room temperature for 16 h. The mixture was poured into water and extracted with DCM. The organic layer was separated and concentrated to afford the title compound. LCMS[M+1]⁺=231.

Step C: (R)-8-(2-methoxy-2-(5H-tetrazolo[5,1-α]isoindol-7-yl)ethyl)-2-(4-methyl-5-oxo-2,5-dihydrofuran-3-yl)-2,8-diazaspiro[4.5]decan-1-one To a solution of (R)-2-methoxy-2-(5H-tetrazolo[5,1-α] isoindol-7-yl)acetaldehyde (20 mg, 0.09 mmol) in DCM (3 mL) was added 2-(4-methyl-5-oxo-2,5-dihydrofuran-3-yl)-2,8-diazaspiro[4.5]decan-1-one (Int. 2; 20 mg, 0.08 mmol), NaBH(OAc)₃ (56 mg, 0.26 mmol) and AcOH (0.05 mL). The mixture was stirred at room temperature for 0.5 h. The mixture was partitioned between water and DCM. The organic layer was separated and concentrated. The crude product was purified by preparative TLC using MeOH/DCM as the developing solvents to afford the title compound. LCMS [M+1]⁺=465.2. ¹H NMR (400 MHz, CD₃OD) δ 8.05-8.00 (m, 1H), 7.78 (s, 1H), 7.64 (d, J=7.8 Hz, 1H), 5.25 (s, 1H), 4.67-4.59 (m, 2H), 4.08 (t, J=7.0 Hz, 2H), 3.12 (s, 2H), 2.91-2.86 (m, 1H), 2.56-2.44 (m, 3H), 2.18-2.14 (m, 1H), 2.01 (s, 2H), 1.91 (s, 2H), 1.63 (d, J=14 Hz, 2H), 1.36-.28 (m, 6H).

The following Thallium Flux Assay was performed on each of the final product compounds in the Examples.

Thallium Flux Assay

A Thallium Flux Assay was performed on the compounds of the Examples. This assay has been described previously; see, e.g., PCT Published Application WO 2013/062900.

Data collected for compounds in the Examples of the present invention using the Thallium Flux Assay are shown in Table 3 below. All of the tested final product compounds in the Examples (diastereomeric mixtures and individual diastereomers) had IC₅₀ potencies less than 1 μM in the Thallium Flux Assay.

TABLE 3

| Example No. | Thallium Flux IC₅₀ (μM) |
|---|---|
| 1 | 0.031 |
| 2 | 0.009 |
| 3 | 0.035 |
| 4 | 0.043 |
| 5 | 0.111 |
| 6 | 0.040 |
| 7A | 0.034 |
| 7B | 0.038 |
| 8 | 0.013 |
| 9 | 0.019 |
| 10 | 0.046 |
| 11 | 0.047 |
| 12 | 0.188 |
| 13 | 0.023 |
| 14 | 0.284 |
| 15 | 0.014 |
| 16 | 0.032 |
| 17 | 0.020 |
| 18 | 0.007 |
| 19 | 0.010 |
| 20 | 0.011 |
| 21 | 0.019 |

TABLE 3-continued

| Example No. | Thallium Flux IC₅₀ (μM) |
|---|---|
| 22 | 0.185 |
| 23 | 0.017 |
| 24 | 0.016 |
| 25 | 0.128 |
| 26 | 0.082 |
| 27A | 0.087 |
| 27B | 0.027 |
| 27C | 0.036 |
| 27D | 0.029 |
| 28 | 0.018 |
| 28A | 0.044 |
| 29 | 0.421 |
| 30 | 0.006 |
| 31 | 0.239 |

While the invention has been described with reference to certain particular embodiments thereof, numerous alternative embodiments will be apparent to those skilled in the art from the teachings described herein. The scope of the claims should not be limited by the preferred embodiments set forth in the examples, but should be given the broadest interpretation consistent with the description as a whole. Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. All patents, patent applications and publications cited herein are incorporated by reference in their entirety.

What is claimed is:

1. A compound having structural Formula I:

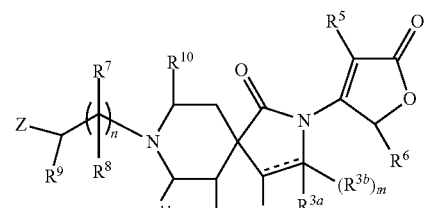

or a pharmaceutically acceptable salt thereof wherein:

Z is

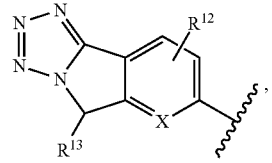

X is C(R⁴);
R¹ is —H, halo, —OH, or —OC₁₋₃alkyl;
R² is —H, =O, —OH, —C₁₋₃alkyl or —OC₁₋₃alkyl;
R³ᵃ is —H, —C₃₋₄cycloalkyl or —C₁₋₃alkyl optionally substituted with —OCH₃ or 1 to 3 of —F;
R³ᵇ is —H or —C₁₋₃alkyl, or R³ᵇ is absent when the dashed bond is a double bond;

or R³ᵃ and R³ᵇ are joined together with the carbon to which they are both attached to form cyclopropyl or cyclobutyl;

R⁴ is —H, halo, —CN, —C₃₋₆cycloalkyl, —C(O)OC₁₋₄alkyl, —OC₁₋₄alkyl, or —C₁₋₄alkyl optionally substituted with OH or 1-3 of —F;

R⁵ is —H, halo, or —C₁₋₃alkyl optionally substituted with —O—C₁₋₃alkyl;

R⁶ is —H or —C₁₋₃alkyl;

R⁷ is —H or —C₁₋₃alkyl optionally substituted with —OH, —OCH₃ or 1 to 3 of —F, or R⁷ is absent when n is zero;

R⁸ is —H or —C₁₋₃alkyl, or R⁸ is absent when n is zero;

or R⁷ and R⁸ are joined together with the carbon to which they are both attached to form cyclopropyl or cyclobutyl;

R⁹ is —H, halo, —OH, —C₁₋₃alkyl, —OC₁₋₃alkyl or —CH₂OH;

R¹⁰ is —H, or —C₁₋₃alkyl optionally substituted with —OH, —OCH₃, or 1 to 3 of —F;

R¹¹ is —H, or —C₁₋₃alkyl optionally substituted with —OH, —OCH₃, or 1 to 3 of —F;

R¹² and R¹³ are each independently —H, halo, —CN, —C₃₋₆cycloalkyl, —C(O)OC₁₋₄alkyl, —OC₁₋₄alkyl, or C₁₋₄alkyl optionally substituted with —OH or 1-3 of —F;

m is zero where R³ᵇ is absent, or one where R³ᵇ is present;

the partially dashed double bond ("---") represents a single or double bond wherein:
 (i) when m is one, then the dashed bond is a single bond; and
 (ii) when m is zero and R² is not =O, then the dashed bond is a double bond; and n is zero or one.

2. The compound having structural Formula Ia

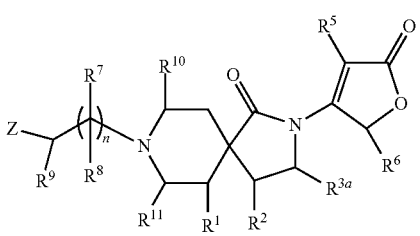

or a pharmaceutically acceptable salt thereof wherein:
Z is

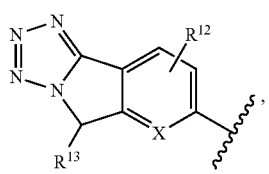

X is C(R⁴);
R¹ is —H, halo, —OH, or —OC₁₋₃alkyl;
R² is —H, =O, —OH, —C₁₋₃alkyl or —OC₁₋₃alkyl;
R³ᵃ is —H, —C₃₋₄cycloalkyl or —C₁₋₃alkyl optionally substituted with —OCH₃ or 1 to 3 of —F;
R⁴ is —H, halo, —CN, —C₃₋₆cycloalkyl, —C(O)OC₁₋₄alkyl, —OC₁₋₄alkyl, or —C₁₋₄alkyl optionally substituted with OH or 1-3 of —F;

R⁵ is —H, halo, or —C₁₋₃alkyl optionally substituted with —O—C₁₋₃alkyl;
R⁶ is —H or —C₁₋₃alkyl;
R⁷ is —H or —C₁₋₃alkyl optionally substituted with —OH, —OCH₃ or 1 to 3 of —F, or R⁷ is absent when n is zero;
R⁸ is —H or —C₁₋₃alkyl, or R⁸ is absent when n is zero;
R⁹ is —H, halo, —OH, —C₁₋₃alkyl, —OC₁₋₃alkyl or —CH₂OH;
R¹⁰ is —H, or —C₁₋₃alkyl optionally substituted with —OH, —OCH₃, or 1 to 3 of —F;
R¹¹ is —H, or —C₁₋₃alkyl optionally substituted with —OH, —OCH₃, or 1 to 3 of —F;
R¹² and R¹³ are each independently —H, halo, —CN, —C₃₋₆cycloalkyl, —C(O)OC₁₋₄alkyl, —OC₁₋₄alkyl, or C₁₋₄alkyl optionally substituted with —OH or 1-3 of —F; and
n is zero or one.

3. The compound of claim 1 wherein:
Z is

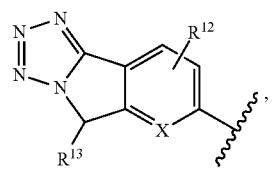

X is C(R⁴);
R¹ is —H, halo, —OH, or —OC₁₋₃alkyl;
R² is —H, =O, —OH, —C₁₋₃alkyl or —OC₁₋₃alkyl;
R3a is —H, —C₃₋₄cycloalkyl or —C₁₋₃alkyl optionally substituted with —OCH₃ or 1 to 3 of —F;
R⁴ is —H, halo or —C₁₋₄alkyl optionally substituted with OH or 1-3 of —F;
R⁵ is —H, halo, or —C₁₋₃alkyl optionally substituted with —O—C₁₋₃alkyl;
R⁶ is —H or —C₁₋₃alkyl;
R⁷ is —H or —C₁₋₃alkyl, or R⁷ is absent when n is zero;
R⁸ is —H, or R⁸ is absent when n is zero;
R⁹ is —H, —F, —OH, —C₁₋₃alkyl, —OC₁₋₃alkyl or —CH₂OH;
R¹⁰ is —H or —C₁₋₃alkyl;
R¹¹ is —H, or —C₁₋₃alkyl;
R¹² and R¹³ are each independently —H, halo, —C₃₋₆cycloalkyl, or C₁₋₄alkyl optionally substituted with —OH or 1-3 of —F; and
n is zero or one;
or a pharmaceutically acceptable salt thereof.

4. The compound of claim 1 wherein:
R¹ is —H or halo;
R² is —H;
R³ᵃ is —H or —C₁₋₃alkyl optionally substituted with —OCH₃ or 1 to 3 of —F;
R⁴ is —H, halo, or —C₁₋₄alkyl;
R⁵ is —H or —C₁₋₃alkyl;
R⁶ is —H;
R⁷ is —H, or R⁷ is absent when n is zero;
R⁸ is —H, or R⁸ is absent when n is zero;
R⁹ is —H, —F, —OH, —C₁₋₃alkyl, —OC₁₋₃alkyl or —CH₂OH;
R¹⁰ is —H;
R¹¹ is —H;
R¹² is —H, cyclopropyl, or —C₁₋₄alkyl optionally substituted with 1-3 of —F;

R¹³ is —H, or —C₁₋₄alkyl optionally substituted with 1-3 of —F; and n is zero or one;

or a pharmaceutically acceptable salt thereof.

5. The compound of claim 1 wherein R⁹ is —OH; or a pharmaceutically acceptable salt thereof.

6. The compound of claim 1 wherein n is one; or a pharmaceutically acceptable salt thereof.

7. The compound of claim 1 wherein Z is:

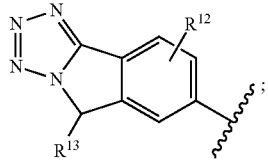

R¹² is —H, cyclopropyl, or —C₁₋₄alkyl optionally substituted with 1-3 of —F; and R¹³ is —H, or —C₁₋₄alkyl optionally substituted with 1-3 of —F.

8. A compound which is:
8-(2-hydroxy-2-(5H-tetrazolo[5,1-a]isoindol-7-yl)ethyl)-2-(4-methyl-5-oxo-2,5-dihydrofuran-3-yl)-2,8-diazaspiro[4.5]decan-1-one;
8-(2-(6-chloro-5H-tetrazolo[5,1-a]isoindol-7-yl)-2-hydroxyethyl)-2-(4-methyl-5-oxo-2,5-dihydrofuran-3-yl)-2,8-diazaspiro[4.5]decan-1-one;
6-fluoro-8-(2-hydroxy-2-(5H-tetrazolo[5,1-a]isoindol-7-yl)ethyl)-2-(4-methyl-5-oxo-2,5-dihydrofuran-3-yl)-2,8-diazaspiro[4.5]decan-1-one;
8-(2-hydroxy-2-(6-methyl-5H-tetrazolo[5,1-a]isoindol-7-yl)ethyl)-2-(4-methyl-5-oxo-2,5-dihydrofuran-3-yl)-2,8-diazaspiro[4.5]decan-1-one;
8-(2-(8-cyclopropyl-5H-tetrazolo[5,1-a]isoindol-7-yl)-2-hydroxyethyl)-2-(4-methyl-5-oxo-2,5-dihydrofuran-3-yl)-2,8-diazaspiro[4.5]decan-1-one;
8-(2-hydroxy-2-(5-methyl-5H-tetrazolo[5,1-a]isoindol-7-yl)ethyl)-2-(4-methyl-5-oxo-2,5-dihydrofuran-3-yl)-2,8-diazaspiro[4.5]decan-1-one;
8-(2-(5H-tetrazolo[5,1-a]isoindol-7-yl)ethyl)-2-(4-methyl-5-oxo-2,5-dihydrofuran-3-yl)-2,8-diazaspiro[4.5]decan-1-one;
8-(2-methoxy-2-(5H-tetrazolo[5,1-a]isoindol-7-yl)ethyl)-2-(4-methyl-5-oxo-2,5-dihydrofuran-3-yl)-2,8-diazaspiro[4.5]decan-1-one;
or a pharmaceutically acceptable salt thereof.

9. A pharmaceutical composition comprising a compound of claim 1 or a pharmaceutically acceptable salt thereof and a pharmaceutically acceptable carrier.

* * * * *